(12) United States Patent
Xu

(10) Patent No.: US 9,499,561 B2
(45) Date of Patent: Nov. 22, 2016

(54) FUSED PYRIMIDINE COMPOUND, AND PREPARATION METHOD, INTERMEDIATE, COMPOSITION, AND USES THEREOF

(71) Applicants: Shanghai Yingli Science and Technology Co., Ltd., Shanghai (CN); Shanghai Chemexplorer Co., Ltd., Shanghai (CN)

(72) Inventor: Zusheng Xu, Shanghai (CN)

(73) Assignee: Shanghai Yingli Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 14/391,386

(22) PCT Filed: Apr. 9, 2013

(86) PCT No.: PCT/CN2013/073974
§ 371 (c)(1),
(2) Date: Oct. 8, 2014

(87) PCT Pub. No.: WO2013/152717
PCT Pub. Date: Oct. 17, 2013

(65) Prior Publication Data
US 2015/0246929 A1    Sep. 3, 2015

(30) Foreign Application Priority Data

Apr. 10, 2012  (CN) .......................... 2012 1 0103541

(51) Int. Cl.
*C07D 495/04*  (2006.01)
*C07D 491/048*  (2006.01)
*C07D 519/00*  (2006.01)

(52) U.S. Cl.
CPC ......... *C07D 495/04* (2013.01); *C07D 491/048* (2013.01); *C07D 519/00* (2013.01)

(58) Field of Classification Search
CPC .......................... C07D 495/04; C07D 491/048
See application file for complete search history.

(56) References Cited

U.S. PATENT DOCUMENTS

| 3,475,429 A * | 10/1969 | Woitun | C07D 495/04 514/822 |
|---|---|---|---|
| 2004/0266780 A1 | 12/2004 | Sadhu et al. | |
| 2008/0269210 A1 | 10/2008 | Castanedo et al. | |
| 2009/0098086 A1 | 4/2009 | Zask et al. | |
| 2009/0181963 A1 | 7/2009 | Dehnhardt et al. | |

FOREIGN PATENT DOCUMENTS

| CN | 101883774 A | 4/2009 |
|---|---|---|
| CN | 102014914 A | 7/2009 |
| CN | 101675053 A | 3/2010 |
| CN | 103467482 A | 12/2013 |
| JP | 2011/500702 A | 1/2011 |
| WO | WO-2007/023382 A2 | 3/2007 |
| WO | WO-2007/044729 A2 | 4/2007 |
| WO | WO-2007/072163 A2 | 6/2007 |
| WO | WO-2007/127183 A1 | 11/2007 |
| WO | WO-2007/129161 A2 | 11/2007 |
| WO | WO-2007/132171 A1 | 11/2007 |
| WO | WO-2008/064093 A2 | 5/2008 |
| WO | WO-2008/088881 A1 | 7/2008 |
| WO | WO-2008/127594 A2 | 10/2008 |
| WO | WO-2009/147187 A1 | 12/2009 |
| WO | WO-2009/147190 A1 | 12/2009 |
| WO | WO 2010/005558 | 1/2010 |
| WO | WO-2010/091808 A1 | 8/2010 |
| WO | WO 2010/105008 | 9/2010 |
| WO | WO-2010/120987 A1 | 10/2010 |
| WO | WO-2010/120994 A2 | 10/2010 |
| WO | WO 2011/079230 | 6/2011 |

OTHER PUBLICATIONS

International Search Report issued in International Patent Application No. PCT/CN2013/073974 dated Jul. 18, 2013 (with English translation).
Written Opinion of the International Searching Authority issued in International Patent Application No. PCT/CN2013/073974 dated Jul. 18, 2013 (with English translation).
Bart Vanhaesebroeck et al., "Phosphoinositide 3-kinases: a conserved family of signal transducers", *Trends Biochem. Sci.*, (1997), 22:267-272.

(Continued)

*Primary Examiner* — Rebecca Anderson
(74) *Attorney, Agent, or Firm* — Sheppard Mullin Richter & Hampton LLP

(57) ABSTRACT

Disclosed are a fused pyrimidine compound as represented by formula I, pharmaceutically acceptable salt, hydrate and solvate thereof, an optical isomer or a prodrug thereof, as well as a preparation method, an intermediate, a composition and uses thereof. The fused pyrimidine compound according to the present invention can inhibit activity of PI3 kinase, and can be used to treat diseases such as cancer caused by abnormal activity of the PI3 kinase, or can be used to prepare medicine for treating these diseases.

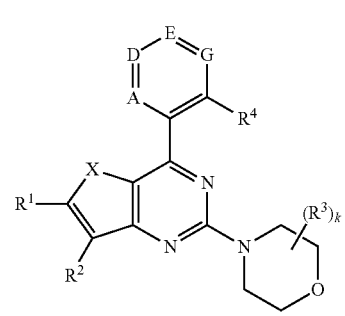

18 Claims, No Drawings

(56) References Cited

OTHER PUBLICATIONS

Igor Vivanco et al., "The Phosphatidylinositol 3-Kinase—Akt Pathway in Human Cancer", *Nat.Rev.Cancer*, (2002), 2:489-501.
Stephen G Ward et al., "Isoform-specific phosphoinositide 3-kinase inhibitors as therapeutic agents", *Curr. Opin.Pharmacol.*, (2003), 3:426-434.
David B. Solit et al., "Inhibition of Heat Shock Protein 90 Function Down-Regulates Akt Kinase and Sensitizes Tumors to Taxol", *Cancer.Res.*, (2003),63:2139-2144.
Roy Katso et al., "Cellular Function of Phosphoinositide 3-Kinases: Implications for Development, Immunity, Homeostasis, and Cancer", *Annu.Rev.Cell Dev.Biol.*, (2001), 17:615-675.
F Chang et al., "Involvement of PI3K/Akt pathway in cell cycle progression, apoptosis, and neoplastic transformation: a target for cancer chemotherapy", *Leukemia*, (2003), 17:590-603.
Hwai Wen Chang et al., "Transformation of Chicken Cells by the Gene Encoding the Catalytic Subunit of PI 3-Kinase", *Science*, (1997), 276:1848-1850.
Qi-Wen Fan et al., "A Dual Phosphoinositide-3-Kinase A/mTOR Inhibitor Cooperates with Blockade of Epidermal Growth Factor Receptor in PTEN-Mutant Glioma", *Cancer Res.*, (2007), 67:7960-7965.
Gary A. Molander et al., "Synthesis of Functionalized Organotrifluoroborates via Halomethyltrifluoroborates", *Org. Lett.*, (2006), 8(10):2031-2034.
Jessica Raushel et al., "Reinvestigation of Aminomethyltrifluoroborates and Their Application in Suzuki-Miyaura Cross-Coupling Reactions", *J. Org. Chem.*, (2011), 76:2762-2769.
Hélio A. Stefani et al., "Recent advances in organotrifluoroborates chemistry", *Tetrahedron*, (2007) 63 :3623-3658.
Sylvain Darses et al., "Potassium Organotrifluoroborates: New Perspectives in Organic Synthesis", *Chem. Rev.*, (2008), 108:288-325.
Norio Miyaura et al., "Palladium-Catalyzed Cross-Coupling Reactions of Organoboron Compounds", *Chem. Rev.*, (1995), 95:2457-2483.
Roger J. Gillespie et al., "Antagonists of the human adenosine A2A receptor. Part 2: Design and synthesis of 4-arylthieno[3,2-d]pyrimidine derivatives", *Bioorganic & Medicinal Chemistry Letters*, (2008), 18: 2920-2923.
Roger J. Gillespie et al., "Antagonists of the human adenosine A2A receptor. Part 3: Design and synthesis of pyrazolo[3,4-d]pyrimidines, pyrrolo[2,3-d]pyrimidines and 6-arylpurines", *Bioorganic & Medicinal Chemistry Letters*, (2008), 18:2924-2929.
Jelena Dodonova et al., "Synthesis of 4-aryl-, 2,4-diaryl- and 2,4,7-triarylpyrrolo[2,3-d]pyrimidines by a combination of the Suzuki cross-coupling and N-arylation reactions", *Tetrahedron*, (2012), 68:329-339.
Yitzhak Tor et al., "Designing new isomorphic fluorescent nucleobase analogues: the thieno[3,2-d]pyrimidine core", *Tetrahedron*, (2007), 63:3608-3614.
Matthew T. Burger et al., "Identification of NVP-BKM120 as a Potent, Selective, Orally Bioavailable Class I PI3 Kinase Inhibitor for Treating Cancer", *ACS Med. Chem. Lett.*, (2011), 2:774-779.
Supplementary European Search Report for European Patent Application No. EP 13775600.3 dated Oct. 19, 2015.
Office Action in Chinese Application No. 201310122260.1 dated Dec. 2, 2015. English translation included.
English translation of Second Office Action in Chinese Application No. 201310122260.1 dated Jun. 29, 2016.
Link et al., "Chemical Interrogation of FOXO3a Nuclear Translocation Identifies Potent and Selective Inhibitors of Phosphoinositide 3-Kinases", Journal of Biological Chemistry, vol. 284, No. 41, Oct. 9, 2009.
English translation of Office Action in Japanese Application No. 2015-504855 dated Aug. 16, 2016.

* cited by examiner

FUSED PYRIMIDINE COMPOUND, AND PREPARATION METHOD, INTERMEDIATE, COMPOSITION, AND USES THEREOF

CROSS REFERENCE TO RELATED APPLICATIONS

The present application is the U.S. national stage application of International Application PCT/CN2013/073974, filed Apr. 9, 2013, which international application was published on Oct. 17, 2013, as International Publication WO 2013/152717 and the International Application claims priority to Chinese Patent Application 201210103541.8, filed Apr. 10, 2012.

FIELD OF INVENTION

The present invention relates to a fused pyrimidine compound, and preparation method, intermediate, composition, and uses thereof.

PRIOR ART

Phosphoinositide 3-kinase (PI3K) is a type of intracellular phosphatidylinositol kinase that can catalyze the phosphorylation of the 3-hydroxy of phosphatidylinositol. The PI3K family can be divided into three classes (I, II, and III), and the most extensively investigated one is the class I PI3Ks that can be activated by cell surface receptors. Class I PI3Ks in mammalian cells are further divided into two groups based on their structures and receptors, class Ia and class Ib, which transmits signals from tyrosine kinase-coupled receptors and G protein-coupled receptors, respectively. Class Ia PI3Ks are further divided into PI3Kα, PI3Kβ and PI3Kδ (*Trends Biochem. Sci.*, 1997, 22, 267-272). Class Ia PI3Ks are dimers of a catalytic subunit, p110, and a regulatory subunit, p85, having dual activity of lipid kinases and protein kinases (*Nat. Rev. Cancer* 2002, 2, 489-501). PI3K can be activated in two ways, one is through the interaction with growth factor receptors or coupled proteins having phosphorylated tyrosine residues, inducing a conformational change of the dimer; the other is through the direct binding of Ras to p110, thereby inducing the activity of PI3K (*Curr. Opin. Pharmacol.*, 2003, 3, 426-434). The activation of PI3K generates a second messenger PIP3 at the plasma membrane. The binding of PIP3 to intracellular signaling proteins containing a PH domain, Akt and PDK1 (phosphoinositide-dependent kinase-1), causes the phosphorylation of Ser308 of Akt protein by PDK1, which is responsible for activating Akt. Akt can also be activated by phosphorylating its Thr473 by PDK2 (such as integrin-linked kinase, ILK) (*Cancer. Res.*, 2003, 63, 2139-2144). Activated Akt activates or inhibits its downstream target proteins such as mTor, Bad, Caspase9, NF-kB, GSK-3, FKHR and MDM2, etc. by phosphorylation, thereby regulates cell proliferation, differentiation, apoptosis and migration (*Annu. Rev. Cell Dev. Biol.*, 2011, 17, 615-675). Studies have shown that overactivation of PI3K is closely related to human malignancies such as breast cancer, lung cancer, melanoma and lymphoma, etc. (*Leukemia*, 2003, 17, 590-603).

Further, since the mammalian target of rapamycin (mTOR) is the main effector of PI3K signal pathway, it can partially mediate and phosphorylate proto-oncogene Akt/PKB. Recent studies show that the inhibition of PI3Kα is essential to the inhibition of the growth of malignant cells (*Science*, 1997, 276, 1848-1850). PI3K is an upstream molecular of Akt/mTOR pathway, its abnormal activation may cause a series of reactions including the growth, proliferation and motility of cells, the change from epithelial cells to mesenchymal cells, and angiogenesis. Thus, PI3K inhibitors can inhibit tumor cell proliferation, induce tumor cell apoptosis and reverse drug resistance of tumor cells. There is evidence that inhibiting both PI3K and mTOR may have synergistic inhibition for tumor growth (*Cancer Res.*, 67, 7960-7965). Thus, PI3K/mTOR dual inhibitors may be the future direction of development of tumor targeted therapy.

Existing technologies have disclosed a number of compounds as PI3K inhibitors, such as: WO2008064093, WO2007044729, WO2008127594, WO2007127183, WO2007129161, US20040266780, WO2007072163, WO2009147187, WO2009147190, WO2010120987, WO2010120994, WO2010091808, etc.

So far there is no small molecular PI3K inhibitor in market. The object of the present invention is to provide an efficient, low toxicity medicine of PI3K inhibitor for the treatment of cell proliferation diseases such as cancer, infections, inflammation and autoimmune diseases.

Content of the Present Invention

The technical problem to be solved in the present invention is to provide a fused pyrimidine compound which is completely different from prior arts, and preparation method, intermediate, composition, and uses thereof. The fused pyrimidine compound I in the present invention is an efficient, low toxicity PI3 kinase inhibitor which can be used for preventing or treating cell proliferation diseases such as cancer, infections, inflammation and autoimmune diseases.

The present invention provides a fused pyrimidine compound represented by formula I, a pharmaceutically acceptable salt, hydrate, or solvate thereof, an optical isomer or a prodrug thereof,

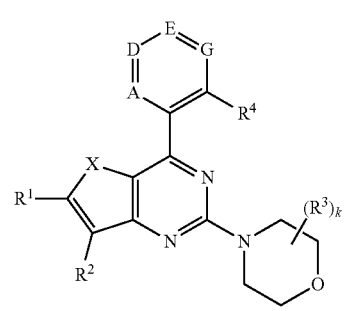

I wherein:

X is S or O;

$R^1$ is hydrogen, deuterium, halogen, an alkyl (such as a $C_{1-6}$ alkyl, preferably a $C_{1-3}$ alkyl), an alkoxy, an alkenyl, an alkynyl, a cycloalkyl, a heterocycloalkyl, an aryl or a heteroaryl;

$R^2$ is hydrogen, deuterium, halogen, CN, —$(CR^8R^9)_m$NR$^5$R$^6$, —$(CR^8R^9)_m$NR$^7$C(=Y)R$^5$, —$(CR^8R^9)_m$NR$^7$S(O)$_2$R$^5$, —$(CR^8R^9)_m$OR$^5$, —$(CR^8R^9)_m$S(O)$_2$R$^5$, —$(CR^8R^9)_m$S(O)$_2$NR$^5$R$^6$, —C(OR$^5$)R$^6$R$^8$, —C(=Y)R$^5$, —C(=Y)OR$^5$, —C(=Y)NR$^5$R$^6$, —C(=Y)NR$^7$OR$^5$, —C(=O)NR$^7$S(O)$_2$R$^5$, —C(=O)NR$^7$(CR$^8$R$^9$)$_m$NR$^5$R$^6$, —NR$^7$C(=Y)R$^6$, —NR$^7$C(=Y)OR$^6$, —NR$^7$C(=Y)NR$^5$R$^6$, —NR$^7$S(O)$_2$R$^5$, —NR$^7$S(O)$_2$NR$^5$R$^6$, —SR$^5$, —S(O)$_2$R$^5$, —S(O)$_2$NR$^5$R$^6$, —SC(=Y)R$^5$, —SC(=Y)OR$^5$, a $C_{1-12}$ alkyl, a $C_{2-8}$ alkenyl, a $C_{2-8}$ alkynyl, a $C_{3-12}$ carbocyclyl, a $C_{2-20}$ heterocyclyl, a $C_{6-20}$ aryl or a $C_{1-20}$ heteroaryl;

$(R^3)_k$ represents that the hydrogens attached to the morpholine ring are substituted by 0-k occurrences of $R^3$, at each occurrence the $R^3$ is the same or different from each other, and independently selected from the group consisting of hydrogen, deuterium, halogen, $C_{1-6}$ alkyl, or any two of the $R^3$ may be linked by a single bond, $C_{1-6}$ alkylene or $C_{1-6}$ alkylene substituted by one or more heteroatoms, the heteroatom is O, N, or S;

A is N or $CR^{4a}$;

D is N or $CR^{4b}$;

E is N or $CR^{4d}$;

G is N or $CR^{4e}$;

A, D, E and G are not N at the same time;

Each of $R^4$, $R^{4a}$, $R^{4b}$, $R^{4d}$ and $R^{4e}$ is independently hydrogen, halogen (such as F, Cl, Br or I), —CN, an alkyl (such as a $C_{1-6}$ alkyl, preferably a $C_{1-3}$ alkyl), an alkoxy (such as a $C_{1-6}$ alkoxy, preferably a $C_{1-3}$ alkoxy), an alkenyl, an alkynyl, a cycloalkyl, a heterocycloalkyl, —$NR^5R^6$, —$OR^5$, —$SR^5$, —$C(O)R^5$, —$NR^5C(O)R^6$, —$N(C(O)R^6)_2$, —$NR^5C(O)NR^5R^6$, —$NR^5S(O)_2R^5$, —$C(=O)OR^5$ or —$C(=O)NR^5R^6$, or $R^4$ or $R^{4d}$, with $R^{4e}$, and the atoms to which they are attached form a saturated, unsaturated or partially unsaturated 5-membered or 6-membered heterocycle, the 5-membered or 6-membered heterocycle contains at least two heteroatoms selected from O, N, or S, the 5-membered or 6-membered heterocycle is fused to the 6-membered ring containing A, D, E and G;

Each of $R^5$, $R^{5'}$, $R^6$, $R^7$ and $R^{7'}$ is independently hydrogen, a $C_{1-12}$ alkyl (such as a substituted or unsubstituted $C_{1-6}$ alkyl, preferably a substituted or unsubstituted $C_{1-4}$ alkyl, such as a substituted or unsubstituted tert-butyl, or a substituted or unsubstituted methyl, whose substituent may be a hydroxyl, e.g., together with the alkyl form (S)-α-hydroxyethyl, (R)-α-hydroxyethyl, hydroxymethyl, or α-hydroxy isopropyl), a $C_{2-8}$ alkenyl, a $C_{2-8}$ alkynyl, a $C_{3-12}$ carbocyclyl, a $C_{2-20}$ heterocyclyl, a $C_{6-20}$ aryl (preferably a substituted or unsubstituted $C_{6-20}$ aryl, e.g., a substituted or unsubstituted phenyl) or a $C_{1-20}$ heteroaryl, or $R^5$, $R^6$ together with the nitrogen to which they are attached form an heterocycle optionally substituted by a substituent selected from the group consisting of: oxo, —$(CH_2)_mOR^7$, —$NR^7R^{7'}$, —$CF_3$, halogen, —$SO_2R^7$, —$C(=O)R^7$, —$NR^7C(=Y)R^{7'}$, —$NR^7S(O)_2R^{7'}$, —$C(=Y)NR^7R^{7'}$, $C_{1-12}$ alkyl, $C_{2-8}$ alkenyl, $C_{2-8}$ alkynyl, $C_{3-12}$ carbocyclyl, $C_{2-20}$ heterocyclyl, $C_{6-20}$ aryl and $C_{1-20}$ heteroaryl;

$R^8$ is hydrogen, deuterium, halogen, —CN, a hydroxy, an alkoxy, a cycloalkoxy, a $C_{1-12}$ alkyl, a $C_{2-12}$ alkenyl, a $C_{2-12}$ alkynyl, a $C_{3-12}$ cycloalkyl, a $C_{6-12}$ aryl, a 3-12 membered heterocycloalkyl or a 5-12 membered heteroaryl;

$(CR^8R^9)_m$ represents that 0-m $(CR^8R^9)$ is connected, wherein each of $R^8$ and $R^9$ is the same or different from each other, and independently selected from hydrogen, deuterium, halogen, —CN, a hydroxy, an alkoxy, a $C_{1-12}$ alkyl, a $C_{2-12}$ alkenyl, a $C_{2-12}$ alkynyl, a $C_{3-12}$ cycloalkyl, a $C_{6-12}$ aryl, a 3-12 membered heterocycloalkyl or a 5-12 membered heteroaryl; or $R^8$, $R^9$ together with the atoms to which they are attached form a saturated or partially unsaturated $C_{3-12}$ carbocyclic ring or $C_{2-20}$ heterocyclic ring;

Wherein the alkyl, alkenyl, alkynyl, cycloalkyl, carbocycle, heterocycle, heterocycloalkyl, aryl, or heteroaryl is optionally substituted by a substituent selected from the group consisting of: halogen, —CN, —$CF_3$, —$NO_2$, oxo, $R^5$, —$C(=Y)R^5$, —$C(=Y)OR^5$, —$C(=Y)NR^5R^6$, —$(CR^8R^9)_mNR^5R^6$, —$(CR^8R^9)_mOR^5$, —$NR^5R^6$, —$NR^7C(=Y)R^5$, —$NR^7C(=Y)OR^6$, —$NR^7C(=Y)NR^5R^6$, —$(CR^8R^9)_mNR^7SO_2R^5$, =$NR^7$, $OR^5$, —$OC(=Y)R^5$, —$OC(=Y)OR^5$, —$OC(=Y)NR^5R^6$, —$OS(O)_2(OR^5)$, —$OP(=Y)(OR^5)(OR^6)$, —$OP(OR^5)(OR^6)$, —$SR^5$, —$S(O)R^5$, —$S(O)_2R^5$, —$S(O)_2NR^5R^6$, —$S(O)(OR^5)$, —$S(O)_2(OR^5)$, —$SC(=Y)R^5$, —$SC(=Y)OR^5$, —$SC(=Y)NR^5R^6$, $C_{1-12}$ alkyl, $C_{2-8}$ alkenyl, $C_{2-8}$ alkynyl, $C_{3-12}$ carbocyclyl, $C_{2-20}$ heterocyclyl, $C_{6-20}$ aryl or $C_{1-20}$ heteroaryl;

Y is O, S, or $NR^7$;

m and k are independently 0, 1, 2, 3, 4, 5 or 6.

Wherein, when $R^2$ is the $C_{1-12}$ alkyl, the $C_{1-12}$ alkyl is preferably a substituted or unsubstituted $C_{1-6}$ alkyl, more preferably a substituted or unsubstituted $C_{1-3}$ alkyl; whose substituent is a $C_{2-20}$ heterocyclyl or —$NR^7C(=Y)R^5$; the $C_{2-20}$ heterocyclyl is optionally substituted by a substituent selected from the group consisting of: halogen, —CN, —$CF_3$, —$NO_2$, oxo, $R^5$, —$C(=Y)R^5$, —$C(=Y)OR^5$, —$C(=Y)NR^5R^6$, —$(CR^8R^9)_nNR^5R^6$, —$(CR^8R^9)_nOR^5$, —$NR^5R^6$, —$NR^7C(=Y)R^5$, —$NR^7C(=Y)OR^6$, —$NR^7C(=Y)NR^5R^6$, —$(CR^8R^9)_mNR^7SO_2R^5$, =$NR^7$, $OR^5$, —$OC(=Y)R^5$, —$OC(=Y)OR^5$, —$OC(=Y)NR^5R^6$, —$OS(O)_2(OR^5)$, —$OP(=Y)(OR^5)(OR^6)$, —$OP(OR^5)(OR^6)$, —$SR^5$, —$S(O)R^5$, —$S(O)_2R^5$, —$S(O)_2NR^5R^6$, —$S(O)(OR^5)$, —$S(O)_2(OR^5)$, —$SC(=Y)R^5$, —$SC(=Y)OR^5$, —$SC(=Y)NR^5R^6$, $C_{1-12}$ alkyl (such as substituted or unsubstituted $C_{1-6}$ alkyl, preferably substituted or unsubstituted $C_{1-3}$ alkyl, whose substituent is preferably a hydroxyl, e.g., together with the alkyl form hydroxyethyl, or α-hydroxy isopropyl), $C_{2-8}$ alkenyl, $C_{2-8}$ alkynyl, $C_{3-12}$ carbocyclyl, $C_{2-20}$ heterocyclyl, $C_{6-20}$ aryl or $C_{1-20}$ heteroaryl; other groups and letters have the meanings given above. The $C_{2-20}$ heterocyclyl is preferably a $C_{2-8}$ saturated heterocyclyl, more preferably a $C_{4-5}$ saturated heterocyclyl, whose heteroatom is N, O or S, more preferably a $C_{4-5}$ saturated heterocyclyl containing two heteroatoms, such as piperazinyl or piperidinyl. Where the $C_{2-20}$ heterocyclyl has one heteroatom, the substituted position of which is preferably on its carbon atom or heteroatom; where the $C_{2-20}$ heterocyclyl has two or more heteroatoms, the substituted position of which is preferably on heteroatoms.

Where $R^2$ is the $C_{2-20}$ heterocyclyl, the $C_{2-20}$ heterocyclyl is optionally substituted by a substituent selected from the group consisting of: halogen, —CN, —$CF_3$, —$NO_2$, oxo, $R^5$, —$C(=Y)R^5$, —$C(=Y)OR^5$, —$C(=Y)NR^5R^6$, —$(CR^8R^9)_nNR^5R^6$, —$(CR^8R^9)_nOR^5$, —$NR^5R^6$, —$NR^7C(=Y)R^5$, —$NR^7C(=Y)OR^6$, —$NR^7C(=Y)NR^5R^6$, —$(CR^8R^9)_mNR^7SO_2R^5$, =$NR^7$, $OR^5$, —$OC(=Y)R^5$, —$OC(=Y)OR^5$, —$OC(=Y)NR^5R^6$, —$OS(O)_2(OR^5)$, —$OP(=Y)(OR^5)(OR^6)$, —$OP(OR^5)(OR^6)$, —$SR^5$, —$S(O)R^5$, —$S(O)_2R^5$, —$S(O)_2NR^5R^6$, —$S(O)(OR^5)$, —$S(O)_2(OR^5)$, —$SC(=Y)R^5$, —$SC(=Y)OR^5$, —$SC(=Y)NR^5R^6$, $C_{1-12}$ alkyl (such as substituted or unsubstituted $C_{1-6}$ alkyl, preferably substituted or unsubstituted $C_{1-3}$ alkyl, whose substituent is preferably a hydroxyl, e.g., together with alkyl form hydroxyethyl, or α-hydroxy isopropyl), a $C_{2-8}$ alkenyl, a $C_{2-8}$ alkynyl, a $C_{3-12}$ carbocyclyl, a $C_{2-20}$ heterocyclyl, a $C_{6-20}$ aryl or a $C_{1-20}$ heteroaryl; other groups and letters have the meanings given above. The $C_{2-20}$ heterocyclyl is preferably a $C_{2-8}$ saturated heterocyclyl or unsaturated heterocyclyl, more preferably a $C_{4-5}$ partially unsaturated heterocyclyl, whose heteroatom is N, O or S, more preferably a $C_{4-5}$ saturated heterocyclyl containing one heteroatom and only one double bond. Where the $C_{2-20}$ heterocyclyl has one heteroatom, the substituted position of which is preferably on its carbon atom or heteroatom; where the $C_{2-20}$ heterocyclyl has two or more heteroatoms, the substituted position of which is preferably on heteroatoms.

In the present invention, the solvate is preferably a hydrate.

In the present invention, the compound I is preferably having the following structure IA:

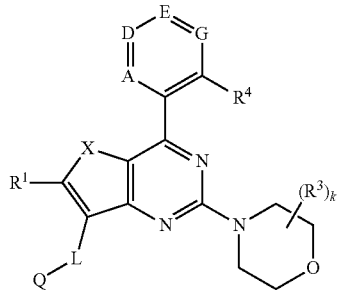

IA wherein Q is a $C_{2-20}$ heterocyclyl, and is optionally substituted by a substituent selected from the group consisting of: halogen, —CN, —CF$_3$, —NO$_2$, oxo, R$^5$, —C(=Y)R$^5$, —C(=Y)OR$^5$, —C(=Y)NR$^5$R$^6$, —(CR$^8$R$^9$)$_n$NR$^5$R$^6$, —(CR$^8$R$^9$)$_n$OR$^5$, —NR$^5$R$^6$, —NR$^7$C(=Y)R$^5$, —NR$^7$C(=Y)OR$^6$, —NR$^7$C(=Y)NR$^5$R$^6$, —(CR$^8$R$^9$)$_m$NR$^7$SO$_2$R$^5$, =NR$^7$, OR$^5$, —OC(=Y)R$^5$, —OC(=Y)OR$^5$, —OC(=Y)NR$^5$R$^6$, —OS(O)$_2$(OR$^5$), —OP(=Y)(OR$^5$)(OR$^6$), —OP(OR$^5$)(OR$^6$), —SR$^5$, —S(O)R$^5$, —S(O)$_2$R$^5$, —S(O)$_2$NR$^5$R$^6$, —S(O)(OR$^5$), —S(O)$_2$(OR$^5$), —SC(=Y)R$^5$, —SC(=Y)OR$^5$, —SC(=Y)NR$^5$R$^6$, a C$_{1-12}$ alkyl (such as a substituted or unsubstituted C$_{1-6}$ alkyl, preferably a substituted or unsubstituted C$_{1-3}$ alkyl, whose substituent is preferably a hydroxyl, e.g., together with the alkyl form hydroxyethyl, or α-hydroxy isopropyl), a C$_{2-8}$ alkenyl, a C$_{2-8}$ alkynyl, a C$_{3-12}$ carbocyclyl, a C$_{2-20}$ heterocyclyl, a C$_{6-20}$ aryl or a C$_{1-20}$ heteroaryl; L is a C$_{1-3}$ alkylene or absent;

or Q is —NR$^7$C(=Y)R$^5$, other groups and letters have the meanings given above.

In the present invention, the compound IA is preferably having a structure represented by a formula selected from the group consisting of:

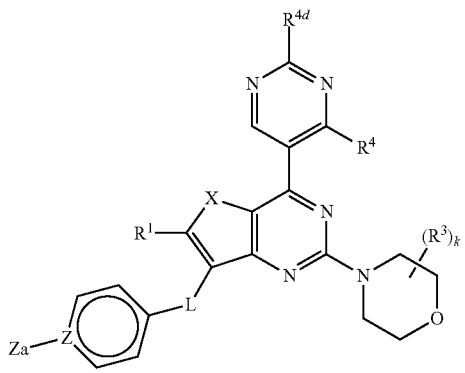

IIA

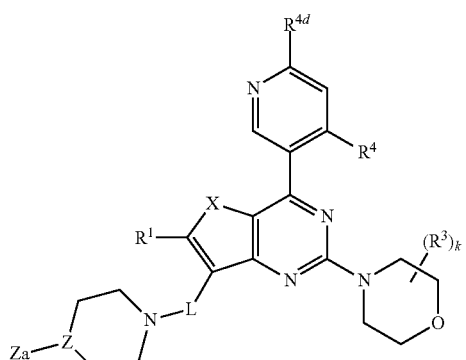

IIB

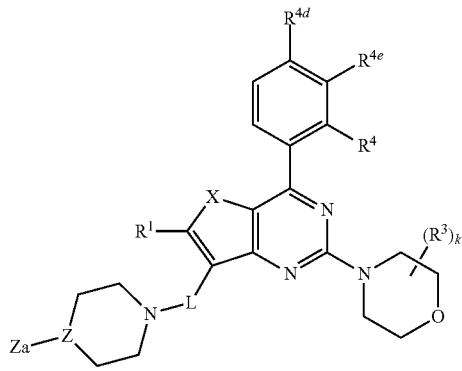

IIC

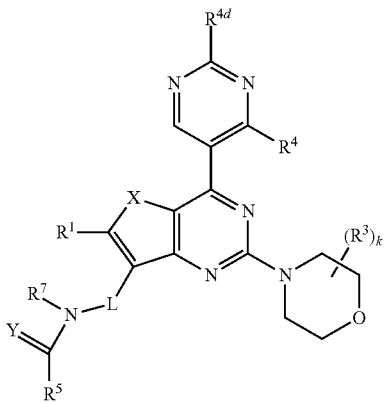

IID

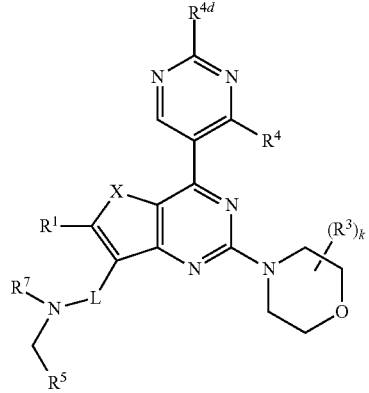

IIE

Wherein, Z is N or CH, Za is —C(=Y)R$^5$, —C(=Y)NR$^5$R$^6$, —S(O)R$^5$, —S(O)$_2$R$^5$, or a C$_{1-12}$ alkyl (such as a substituted or unsubstituted C$_{1-6}$ alkyl, preferably a substituted or unsubstituted C$_{1-3}$ alkyl, whose substituent is preferably a hydroxyl, e.g., together with the alkyl form hydroxyethyl, or α-hydroxy isopropyl); other groups and letters have the meanings given above;

is a saturated, or unsaturated heterocycle (as the partially unsaturated heterocycle, may have only one double bond).

In the present invention, the compound IIC is preferably having a structure represented by a formula selected from the group consisting of:

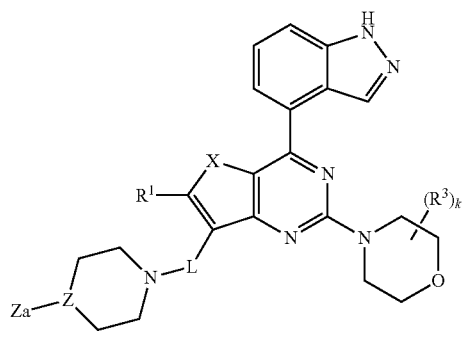

IICa

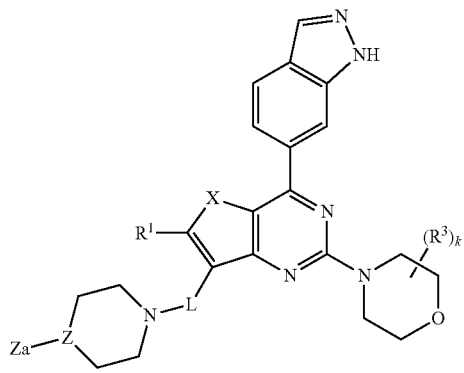

IICb

In the present invention, the

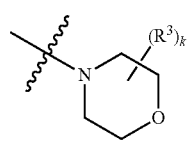

is preferably having a structure represented by a formula selected from the group consisting of:

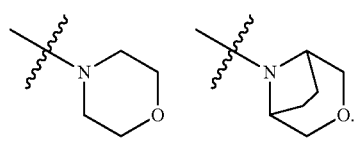 [SMILES: *N1CCOCC1 ; *N1C2CCC1COC2]

In the present invention, the compound I is preferably having a structure represented by a formula selected from the group consisting of:

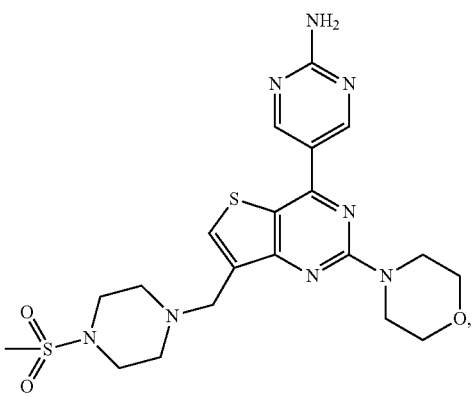

1

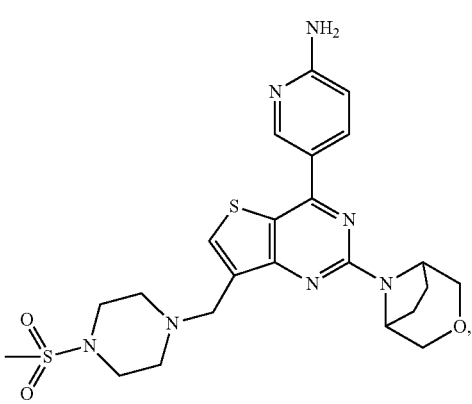

2

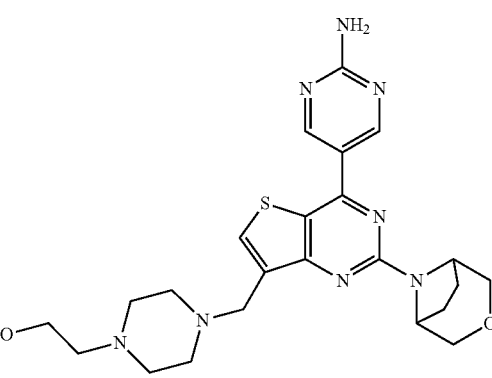

3

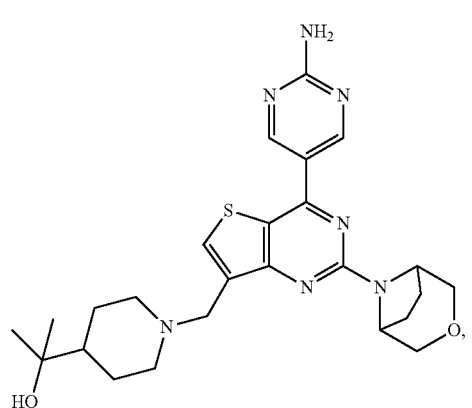

4

US 9,499,561 B2
9
-continued
5
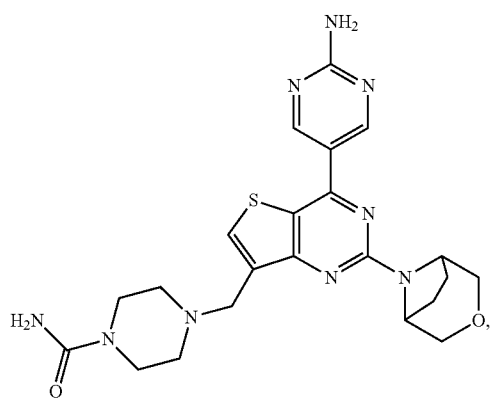
6
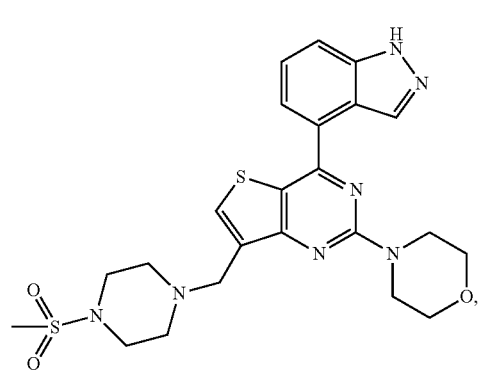
7
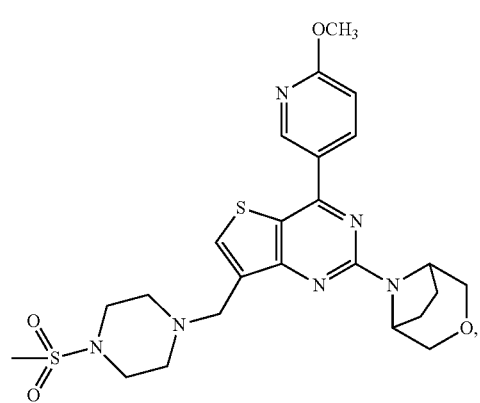
8
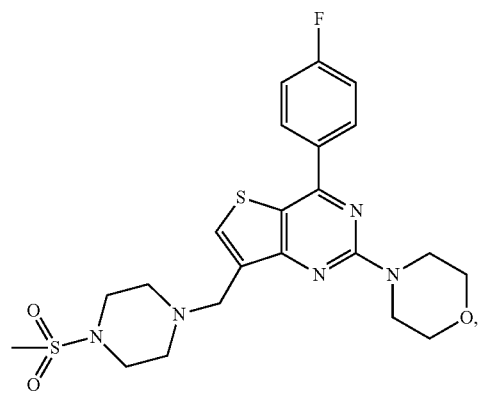
10
-continued
9
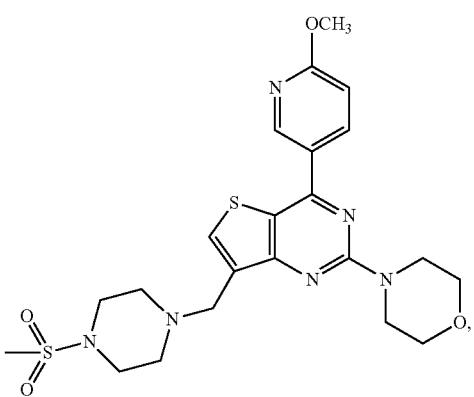
10
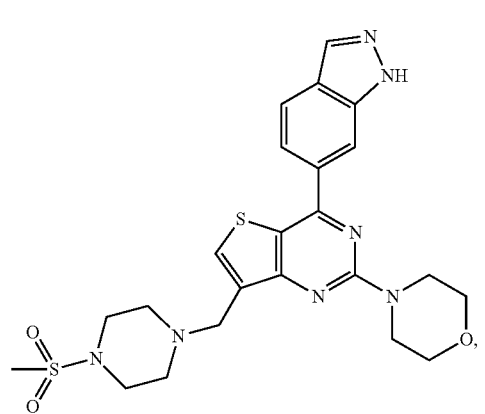
11
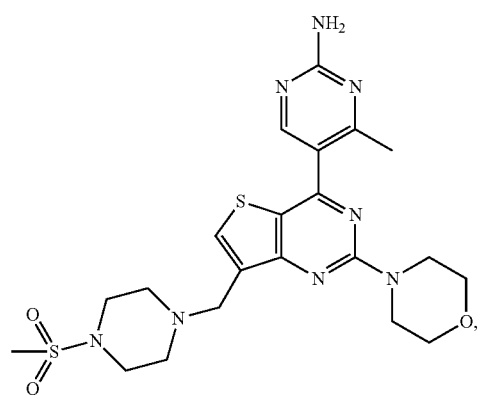
12
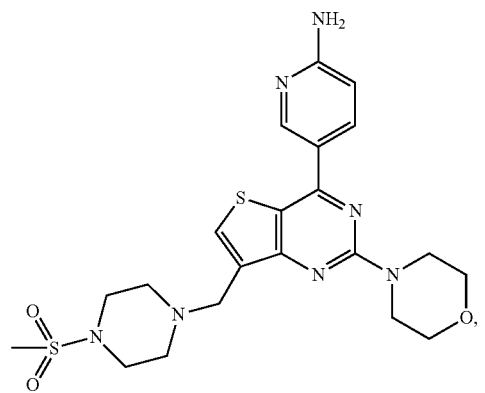

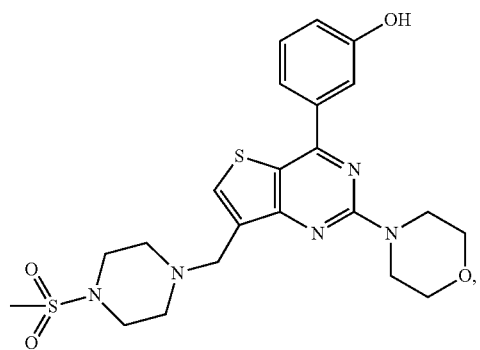
13
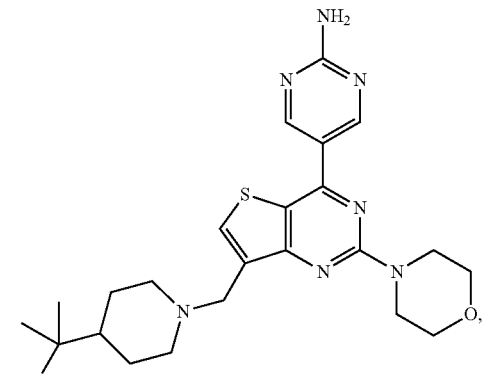
17
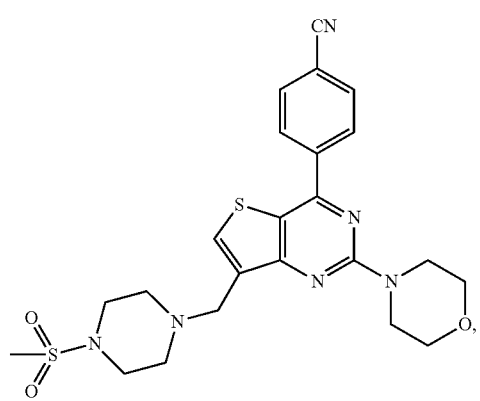
14
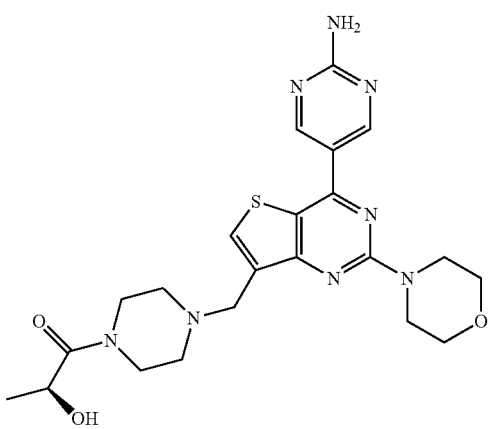
18
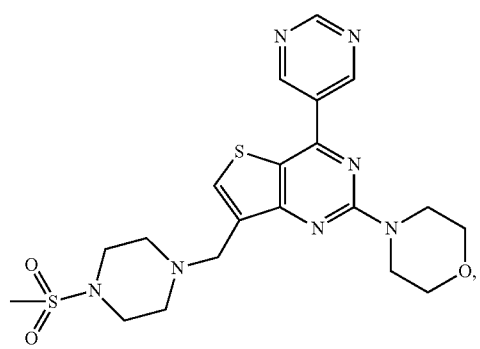
15
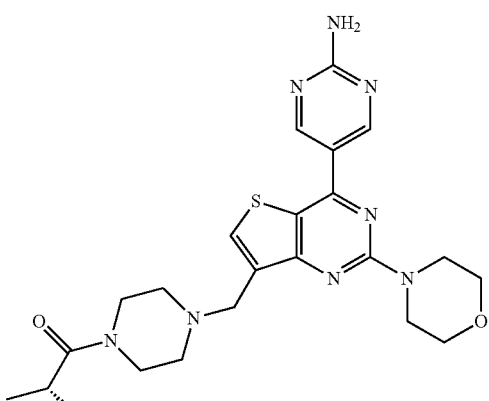
19
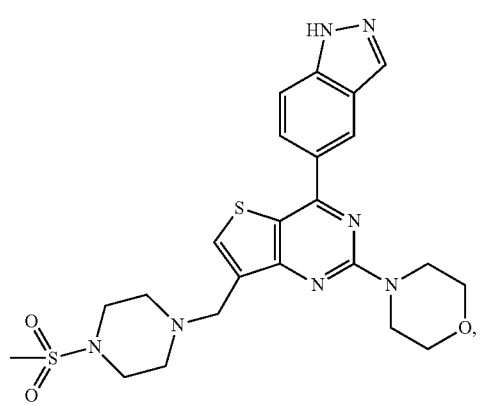
16
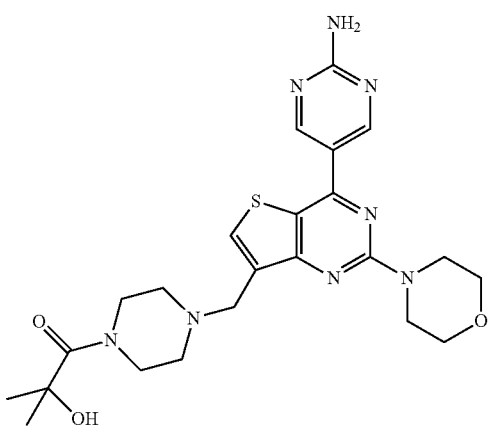
20

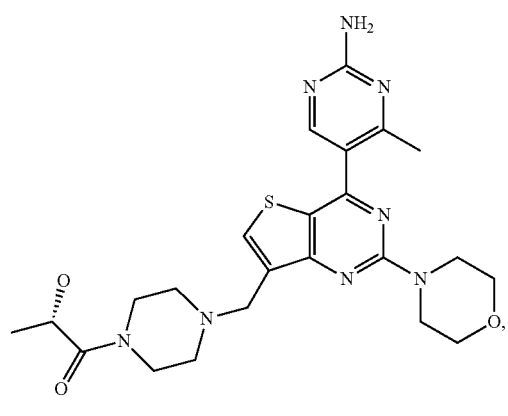
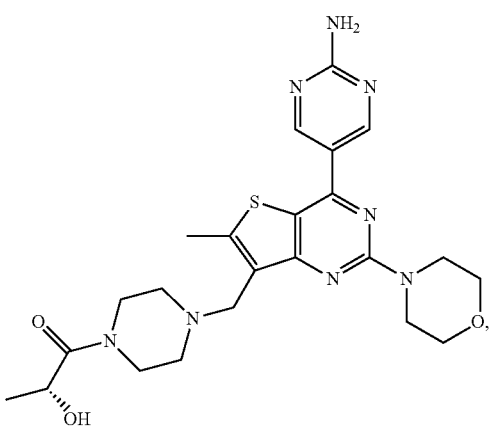
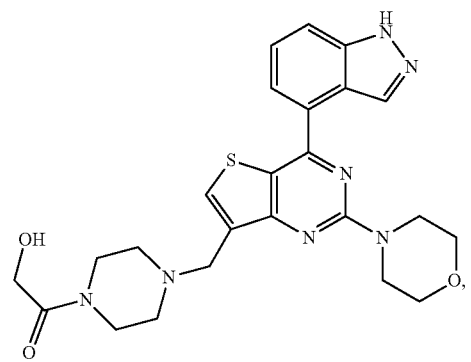
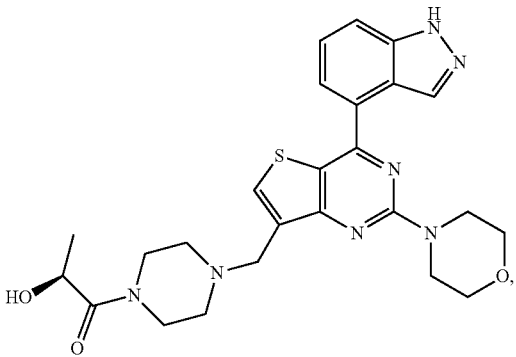
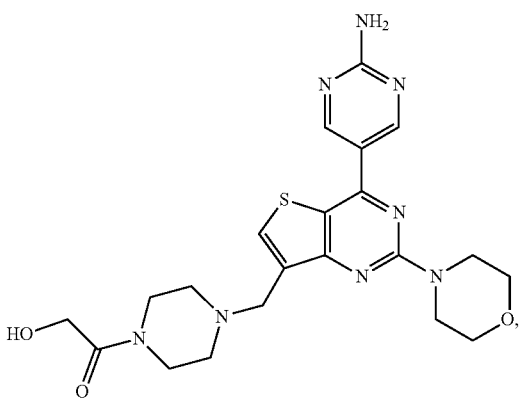

-continued
29
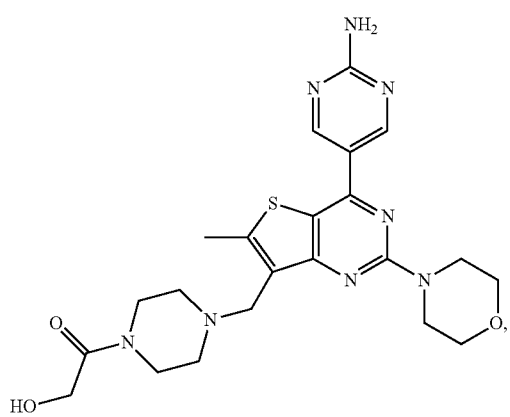
30
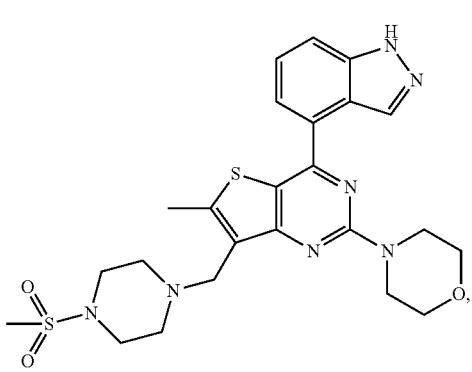
31
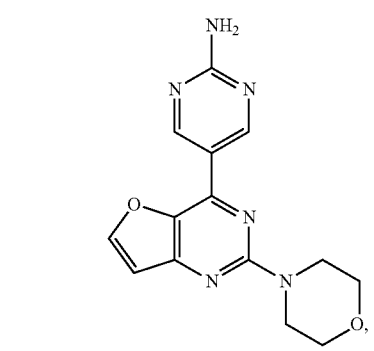
32
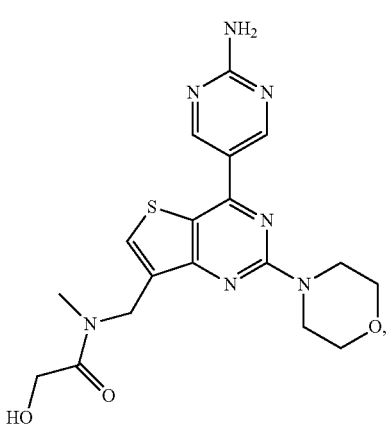
-continued
33
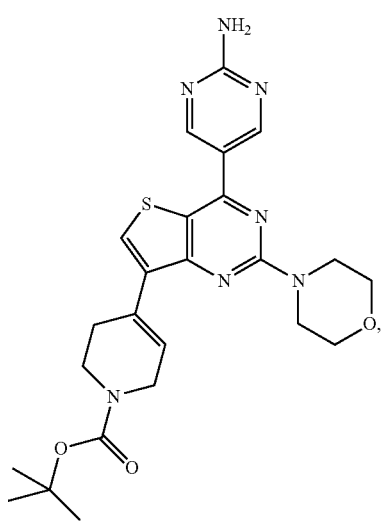
34
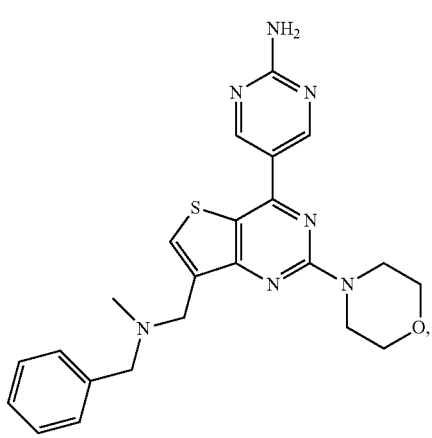
35
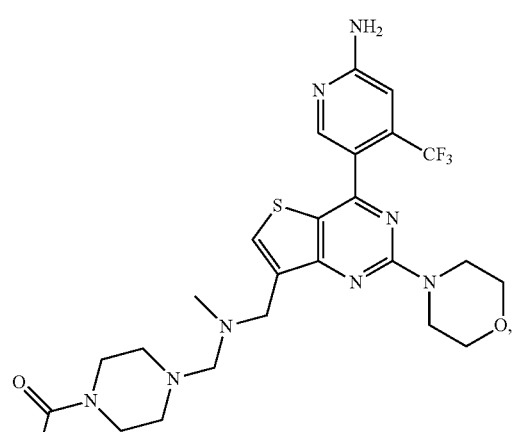

36

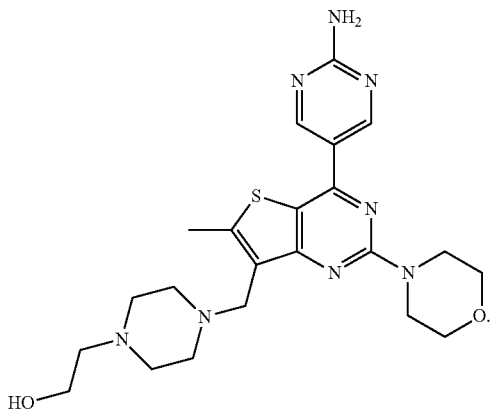

The present invention also provides a process for preparing the compound I, which is any one of the following methods:

Method 1: performing the following coupling reaction between a compound I-a and R²BF₃K or R²B(OR¹⁰)₂;

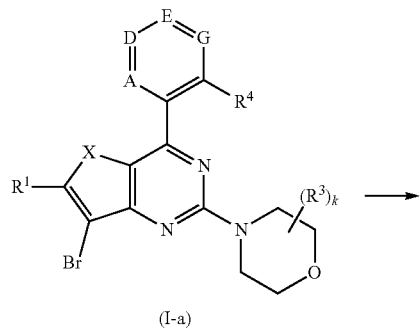

wherein, R¹⁰ is hydrogen, a $C_1$-$C_6$ alkyl, or two OR¹⁰ groups together with the boron atom to which they are attached form a pinacol borate group (as shown below); other groups and letters have the meanings given above.

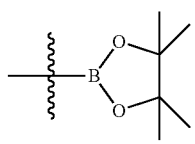

Wherein, the coupling reaction is an organic chemistry reaction type known to those skilled in the art, therefore, the reaction can be carried out according to the coupling reaction methods in references: *Org. Lett.,* 2006, 8 (10), 2031-2034; or *J. Org. Chem.* 2011, 76, 2762-2769; or *Tetrahedron* 63 (2007) 3623-3658; or *Chem. Rev.* 2008, 108, 288-325; or *Chem. Rev.* 1995, 95, 2457-2483.

Method 2: further modifying the compound I (wherein R² is the group as shown below), i.e., deprotecting —CO₂t-Bu

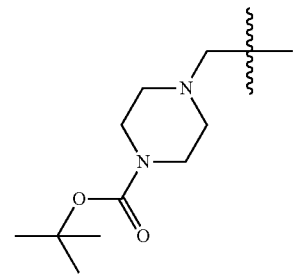 [SMILES: *CN1CCN(C(=O)OC(C)(C)C)CC1]

followed by a N-alkylation, a reductive amination, or a N-acylation reaction known to those skilled in the art, to obtain the target compound I (R² is the group as shown below); other groups have the meanings given above.

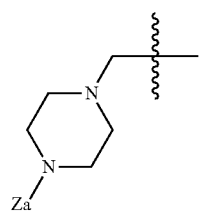

General fomula of the compound I is shown as below:

I

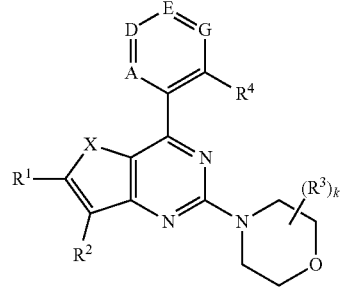

In the present invention, the compound I-a can be prepared by the following method: performing a nucleophilic substitution reaction between a compound I-c and a compound I-b;

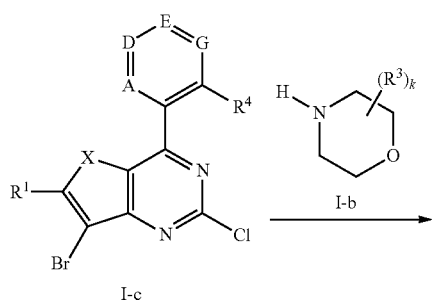

-continued

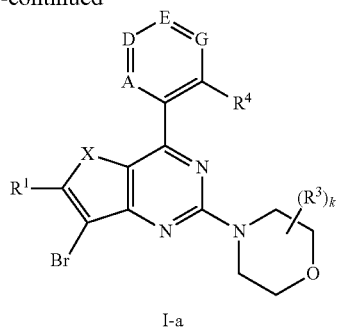

I-a

Wherein, each of the group and the letter has the meaning given above.

Wherein, the nucleophilic substitution reaction is an organic chemistry reaction type known to those skilled in the art, therefore, the reaction can be carried out according to the nucleophilic substitution reaction methods in references: *Bioorganic & Medicinal Chemistry Letters* 18 (2008) 2920-2923; or *Bioorganic & Medicinal Chemistry Letters* 18 (2008) 2924-2929.

In the present invention, the compound I-c can be prepared by the following method: performing a coupling reaction between a compound I-e and a compound I-d;

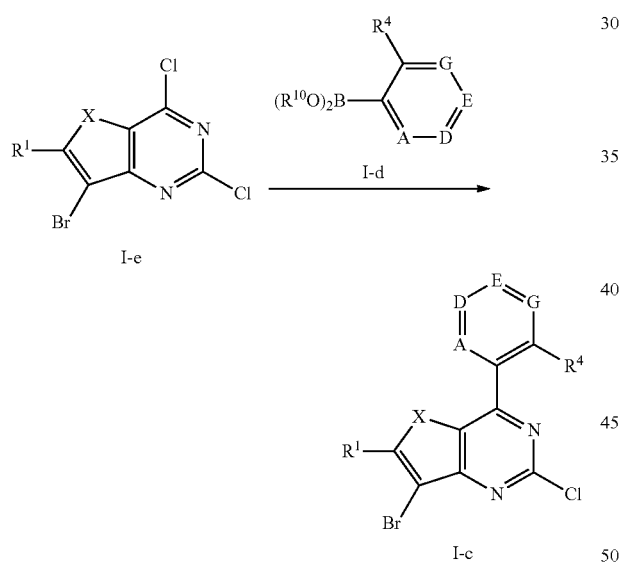

Wherein, $R^{10}$ is hydrogen or a $C_1$-$C_6$ alkyl, or two $OR^{10}$ groups together with the boron atom to which they are attached form a pinacol borate group (as shown below); other groups and letters have the meanings given above.

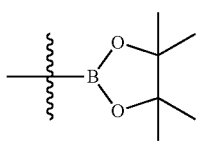

Wherein, the coupling reaction is an organic chemistry reaction type known to those skilled in the art, therefore, the reaction can be carried out according to the coupling reaction methods in references: *Chem. Rev.* 1995, 95, 2457-2483; or *Tetrahedron* 68 (2012) 329-339; or *Bioorganic & Medicinal Chemistry Letters* 18 (2008) 2920-2923; or *Bioorganic & Medicinal Chemistry Letters* 18 (2008) 2924-2929.

Therefore, in the present invention, the preferred reaction route for preparing the compound I is shown below:

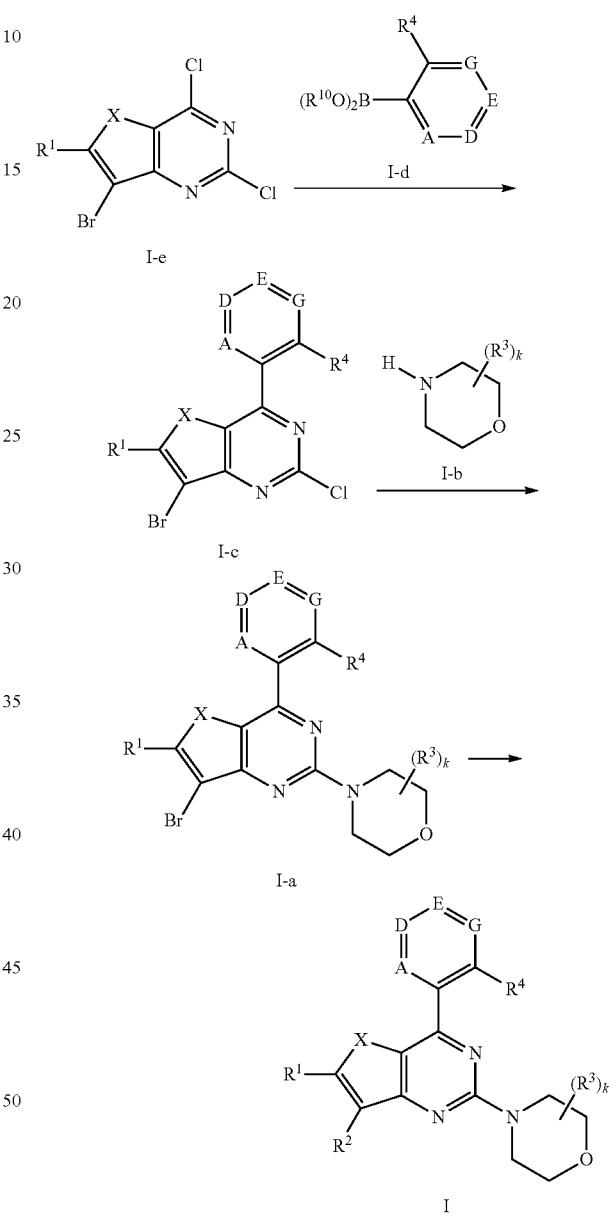

The route uses the compound I-e as a starting material, performing the coupling reaction between the compound I-e and the compound I-d and providing the compound I-c; then performing the nucleophilic substitution reaction between the compound I-b and the compound I-c and providing the compound I-a, coupling the compound I-a and providing the compound represented by the general formula I.

Wherein, the coupling reaction and nucleophilic substitution reaction are organic reactions known to those skilled in the art.

Wherein, the process for preparing the starting material compound I-e ($R^1$=H) can refer to a reference (*Tetrahedron*

2007, 63, 3608-3614); the compound I-e (R¹≠H) can be prepared by the following method: performing a bromination reaction of a compound I-f as follows;

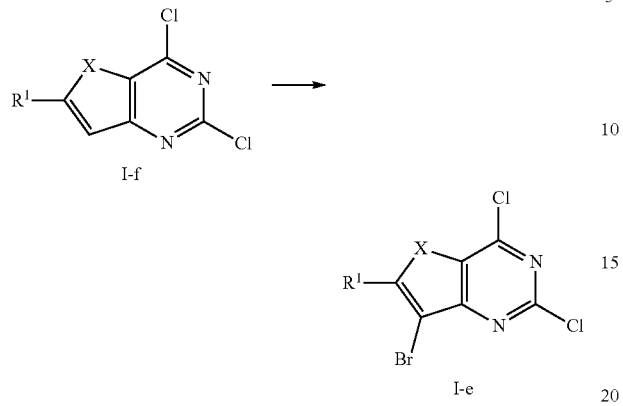

wherein, R¹ has the meaning given above, except for hydrogen.

Wherein, the methods and conditions used for the bromination reaction can be that commonly used for this kind of reactions in this field, while the present invention prefers the following methods and conditions: in a solvent, in the presence of a lewis acid, preforming the reaction between the compound I-f and bromine. Wherein, the solvent is preferably acetic acid or propionic acid, more preferably acetic acid. The amount of the solvent is in the range preferably from 2 to 20 mL/g relative to the mass of the compound I-f. The lewis acid is preferably selected from the group consisting of aluminum trichloride, titanium tetrachloride and/or tin chloride, more preferably aluminum trichloride. The molar ratio of the bromine to the compound I-f is in the range preferably from 1 to 6, more preferably from 2 to 4. The temperature of the reaction is in the range preferably from 0 to 120° C., more preferably from 20 to 100° C. The reaction is terminated preferably when completion is detected, which generally costs 3 to 20 hours.

Wherein, the compound I-f can be prepared by using the methods known in the organic chemistry field, such as referring to the method described in reference (WO2007/023382; CN101675053).

According to the above preparation methods disclosed in the present invention, the person skilled in the art may use the same principles and methods to prepare the particular compound represented by general formula I in the present invention.

The present invention further provides an intermediate compound used for preparing the compound I mentioned above, having a structure represented by a formula selected from the group consisting of:

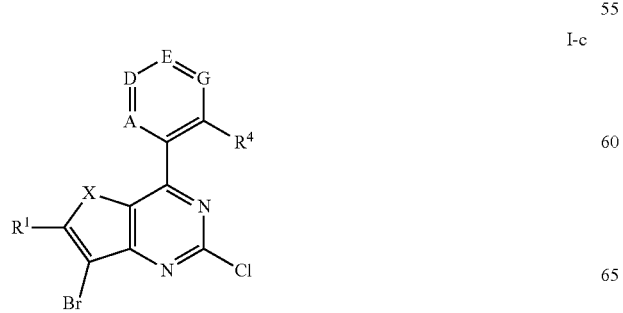

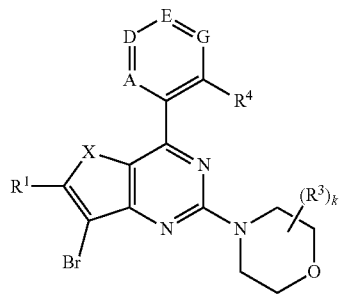

Wherein, each of the group and the letter has the meaning given above.

In the present invention, the intermediate compound I-c is preferably having a structure represented by a formula selected from the group consisting of:

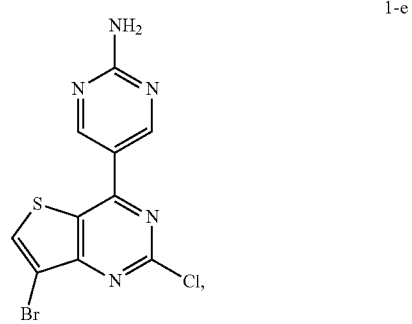

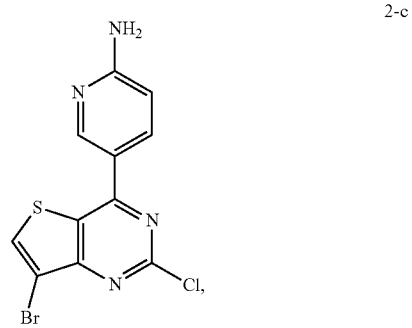

-continued
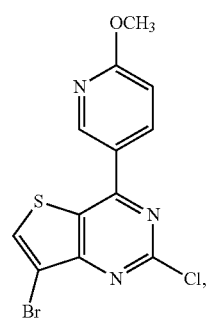
7-b
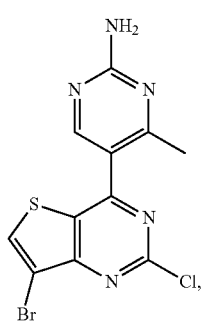
11-b
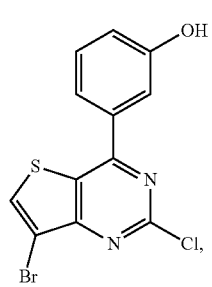
13-b
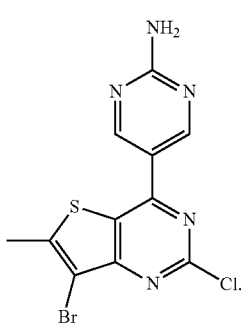
24-d
In the present invention, the intermediate compound I-a is preferably having a structure represented by a formula selected from the group consisting of:
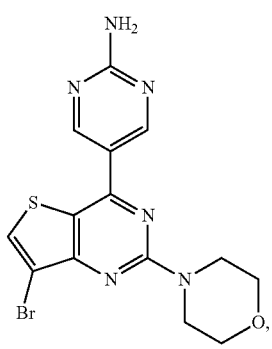
1-d
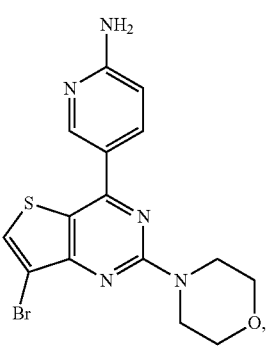
12-a
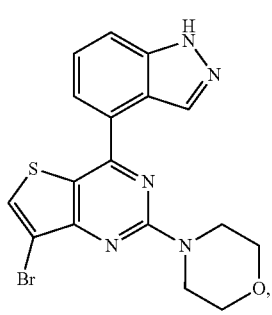
6-a
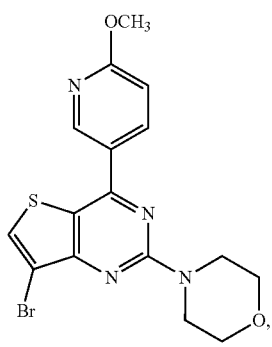
9-a
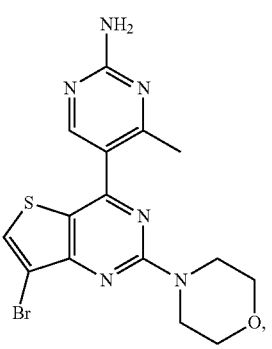
11-a

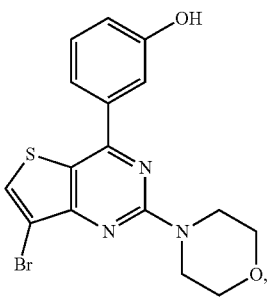

13-a

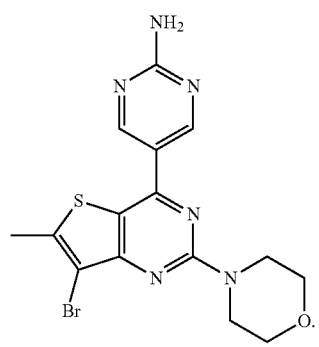

24-c

The present invention further provides a use of the compound represented by general formula I, a pharmaceutically acceptable salt, and a solvate thereof, an optical isomer or a prodrug thereof in preparing a kinase inhibitor, or an agent used for treating and/or preventing diseases associated with kinases, wherein, the kinase is preferably a PI3 kinase (PI3K), more preferably class Ia subtype of PI3K.

The chemical formula involved in the present invention may exhibit tautomerism, structural isomers and stereoisomers. The present invention includes any tautomeric or structural isomeric or stereoisomeric forms, or mixtures thereof, and they have an ability in modulating kinase activity, and this ability is not limited to any form of isomers or mixtures thereof.

Another aspect of the present invention is to provide a method for treating or preventing organisms' diseases associated with kinases, comprising administering to an organism, such as a mammal, particularly a human a medicament comprising a therapeutically effective amount of the compound I according to the present invention.

Another aspect of the present invention is that the disease associated with kinases is a disease associated with PI3 kinase.

Another aspect of the present invention is to provide a pharmaceutical composition, comprising a therapeutically effective amount of the compound of general formula I, or the pharmaceutically acceptable salt thereof, or the pharmaceutically acceptable solvate thereof, or the prodrug thereof, and the pharmaceutically acceptable carrier. The present invention further provides a use of the pharmaceutical composition in preparing a kinase inhibitor, or an agent used for treating or preventing diseases associated with kinases, especially in preparing a PI3 kinase inhibitor, or an agent used for treating or preventing diseases or disorders associated with PI3 kinase.

Herein the term "therapeutically effective amount" means (i) the amount of the compound of the present invention, the pharmaceutically acceptable salt, and the solvate thereof, the optical isomer or the prodrug thereof required for preventing or treating the specific disease or disorder described in the application; (ii) the amount of the compound of the present invention, the pharmaceutically acceptable salt, and the solvate thereof, the optical isomer or the prodrug thereof required for attenuating, ameliorating, or eliminating one or more symptoms of the specific disease or disorder described in the application; or (iii) the amount of the compound of the present invention, the pharmaceutically acceptable salt, and the solvate thereof, the optical isomer or the prodrug thereof required for preventing or delaying the onset of one or more symptoms of the specific disease or disorder described in the application. An amount for treating human patients may range from 0.0001 mg/kg to 50 mg/kg, a typical amount may range from 0.001 mg/kg body weight to 10 mg/kg body weight, e.g. within the range from 0.01 mg/kg to 1 mg/kg. Such amount may be given, for example 1-5 times a day.

The diseases or disorders described in the present application include, but are not limited to: cancer, immune disorder, metabolism/endocrine disorder, cardiovascular disease, viral infection, inflammation or neurological disorder, and any combination of these diseases or disorders, preferably the disease is cancer.

The cancer described in the present invention include, but are not limited to: lung cancer, bone cancer, pancreatic cancer, skin cancer, head and neck cancer, melanoma, uterine cancer, ovarian cancer, colorectal cancer, cancer of the anal region, stomach cancer, liver cancer, colon cancer, breast cancer, cervical cancer, vaginal cancer, vulva cancer, Hodgkin's disease, esophageal cancer, small intestine cancer, thyroid cancer, parathyroid cancer, adrenal cancer, soft tissue sarcoma, urethral cancer, penile cancer, prostate cancer, chronic or acute leukemia, childhood solid tumors, lymphocytic lymphoma, bladder cancer, kidney cancer, ureter cancer, pediatric malignancy, primary CNS lymphoma, spinal axis tumors, brain stem glioma, pituitary adenoma, acute myeloid leukemia, chronic myeloid leukemia, and any combination of these cancers. Preferably, the cancer is lung cancer, pancreatic cancer, prostate cancer, gastric cancer or breast cancer.

Another aspect of the present invention is that the compound (I) of the present invention, or the pharmaceutically acceptable salt thereof, or the pharmaceutically acceptable solvate thereof, or the prodrug thereof may be administered alone or in combination with other pharmaceutically acceptable therapeutic agents, particularly in combination with other anticancer drugs. The therapeutic agents include, but are not limited to: mitotic inhibitors, alkylating agents (such as fluorouracil (5-FU), leucovorin, capecitabine, gemcitabine, UFT and cytarabine), alkyl sulfonates (such as busulfan, improsulfan and piposulfan), aziridines (such as benzodepa, carboquone, meturedepa and uredepa), ethylene imines and methyl melamines (such as altretamine, tretamine, triethylenephosphoramide, triethylenethiophosphoramide and trihydroxylmethylmelamine), nitrogen mustards (such as chlorambucil, cyclophosphamide, estramustine, ifosfamide, novoembichin and prednimustine), triazines (such as dacarbazine), anti-metabolite (such as methotrexate, pteropterin, mercaptopurine and thioguanine), cell cycle inhibitors, topoisomerase inhibitors, biological response modifiers, antibodies, cytomycin, microtubule-acting agents (such as paclitaxel, docetaxel, and epothilones, etc.), platinum complexes (such as carboplatin, cisplatin, etc.), antibiotics (such as bleomycin, dactinomycin, etc.), hormones (such as mitotane, aminoglutethimide, prednisone, hydroxyprogesterone caproate, stilbestrol, tamoxifen, testosterone propionate), aromatase inhibitors (such as anastrozole, etc.), plants (such as vinblastine, vincristine, vindesine, colchicine and camptothecin, etc.), protein kinase inhibitors (such as gleevec, erlotinib, acrivastine, iressa, icotinib, herceptin, erbitux, sutent, sorafenib, sprycel and lapatinib, etc.), histone deacetylase inhibitors (such as vorinostat, etc.), anti-inflammatory drugs (such as ibuprofen, naproxen, celecoxib, valdecoxib, parecoxib and imrecoxib, etc.), and any combination of these drugs.

The pharmaceutical composition of the present invention may be in a form suitable for oral administration, may also be in the form of a sterile injectable aqueous solution. The oral administration or injectable aqueous solution may be prepared according to any known methods for preparing a pharmaceutical composition in the art.

Unless otherwise indicated, the following terms when used in the descriptions and the claims of the present invention have the following meanings:

As used herein, the term "alkyl" (used alone or as a part of other groups) refers to a saturated linear or branched-chain aliphatic hydrocarbyl containing 1 to 20 carbon atoms, preferably 1 to 12 carbon atoms, more preferably 1 to 6 carbon atoms, such as methyl, ethyl, n-propyl, isopropyl, n-butyl, tert-butyl, isobutyl, pentyl, hexyl, heptyl, octyl, nonyl, decyl, 4,4-dimethylpentyl, 2,2,4-trimethylpentyl, undecyl, dodecyl, and the various isomers thereof etc.; as well as the alkyl groups containing 1 to 4 substituents selected from the group consisting of: deuterium, halogen (preferred F, Br, Cl or I), alkyl, alkoxy, aryl, aryloxy, aryl or diaryl substituted by aryl, arylalkyl, arylalkoxy, alkenyl, alkynyl, cycloalkyl, cycloalkenyl, cycloalkylalkyl, cycloalkylalkoxy, optionally substituted amino (such as amino substituted by one to two $C_1$-$C_3$ alkyl groups, or —NR$^7$C(=Y)R$^5$ mentioned above), hydroxyl, hydroxyalkyl, acyl, aldehyde group, heteroaryl, heteroaryloxy, heterocycloalkyl, heterocycloalkoxy, arylheteroaryl, arylalkoxycarbonyl, heteroarylalkyl, heteroarylalkoxy, aryloxyalkyl, aryloxyaryl, alkylamino, acylamino, arylcarbonylamino, $C_{2-20}$ heterocyclyl, nitro, cyano, thiol, haloalkyl, trihaloalkyl (such as trifluoromethyl) and/or alkylthio. "$C_{x1}$-$C_{y1}$" alkyl (x1 and y1 are integer) described in the present invention with the range of the number of carbon atoms specified, such as "$C_1$-$C_{12}$ alkyl", except that the range of the number of carbon atoms differs from the range of the number of carbon atoms of "alkyl" defined in this paragraph, has the same definition as term "alkyl".

As used herein, the term "alkylene" (used alone or as a part of other groups) refers to a subsaturated linear or branched-chain aliphatic hydrocarbyl containing 1 to 20 carbon atoms, preferably 1 to 12 carbon atoms, more preferably 1 to 6 carbon atoms, such as methylene, ethylene, n-propylene, isopropylene, n-butylene, tert-butylene, isobutylene, pentylene, hexylene, heptylene, octylene, nonylene, decylene, 4,4-dimethylpentylene, 2,2,4-trimethylpentylene, undecylene, dodecylene, and the various isomers thereof etc.; as well as the alkylene containing 1 to 4 substituents selected from the group consisting of: deuterium, halogen (preferred F, Br, Cl or I), alkyl, alkoxy, aryl, aryloxy, aryl or diaryl substituted by aryl, arylalkyl, arylalkoxy, alkenyl, alkynyl, cycloalkyl, cycloalkenyl, cycloalkylalkyl, cycloalkylalkoxy, optionally substituted amino (such as amino substituted by one to two $C_1$-$C_3$ alkyl groups), hydroxyl, hydroxyalkyl, acyl, aldehyde group, heteroaryl, heteroaryloxy, heterocycloalkyl, heterocycloalkoxy, arylheteroaryl, arylalkoxycarbonyl, heteroarylalkyl, heteroarylalkoxy, aryloxyalkyl, aryloxyaryl, alkylamino, acylamino, arylcarbonylamino, nitro, cyano, thiol, haloalkyl, trihaloalkyl (such as trifluoromethyl), and/or alkylthio; the substituents selected from the group mentioned above may also form a ring together with the alkylene group, thereby forming a spiro ring or a fused ring.

The term "alicyclyl", "carbocyclyl", or "cycloalkyl" (used alone or as a part of other groups) includes saturated or partially unsaturated (containing 1 or 2 double bonds) cyclic hydrocarbon groups containing 1 to 3 rings, including monocyclic alkyl, bicyclic alkyl and tricyclic alkyl, containing a total of 3 to 20 carbon atoms when forming the rings, preferably 3 to 12 carbon atoms, for example: cyclopropyl, cyclobutyl, cyclopentyl, cyclohexyl, cycloheptyl, cyclooctyl, cyclodecyl and cyclododecyl, cyclohexenyl; the cycloalkyl may be optionally substituted by 1 to 4 substituents selected from the group consisting of: deuterium, halogen, alkyl, alkoxy, hydroxyl, aryl, aryloxy, arylalkyl, cycloalkyl, alkylamino, acylamino, oxo, acyl, arylcarbonylamino, amino, nitro, cyano, thiol and/or alkylthio and/or any alkyl substituents. In addition, any cycloalkyl ring may be fused to a cycloalkyl, aryl, heteroaryl or heterocycloalkyl ring, and to form a fused ring or a spiro ring.

The term "alkoxy" refers to a cyclic or non-cyclic alkyl group containing the indicated number of carbon atoms and having a connection through an oxygen bridge. Thus, "alkoxy" includes the definition of "alkyl" and "cycloalkyl" mentioned above.

The term "alkenyl" refers to a straight-chain, branched-chain or cyclic non-aromatic hydrocarbyl having the indicated number of carbon atoms and at least one carbon-carbon double bond. Preferably there is one carbon-carbon double bond, and may have up to four non-aromatic carbon-carbon double bonds. Thus, "$C_2$-$C_{12}$ alkenyl" refers to an alkenyl group having 2 to 12 carbon atoms. "$C_2$-$C_6$ alkenyl" refers to an alkenyl group having 2 to 6 carbon atoms, including vinyl, propenyl, butenyl, 2-methyl-butenyl and cyclohexenyl. A double bond may locate at the straight-chain, branched or cyclic portion of the alkenyl group and, where specified, the alkenyl group may be substituted.

The term "alkynyl" refers to a straight-chain, branched-chain or cyclic hydrocarbyl having the indicated number of carbon atoms and at least one carbon-carbon triple bond. It may have up to three carbon-carbon triple bonds. Thus, "$C_2$-$C_{12}$ alkynyl" refers to an alkynyl group having 2 to 12 carbon atoms. "$C_2$-$C_6$ alkynyl" refers to an alkynyl group having 2 to 6 carbon atoms, including ethynyl, propynyl, butynyl and 3-methyl-1-butynyl and the like.

As used herein, the term "aryl" refers to any stable monocyclic or bicyclic carbocyclic ring containing up to 7 atoms in each ring, wherein at least one ring is an aromatic ring. Examples of the above-mentioned aryl group include phenyl, naphthyl, tetrahydronaphthyl, 2,3-indanyl, biphenyl, phenanthryl, anthryl or acenaphthyl. It can be understood that if an aryl substituent is a bicyclic ring having one non-aromatic ring, then the connection is through the aromatic ring. It also includes the aryl optionally substituted by 1 to 4 substituents selected from the group consisting of: deuterium, halogen (preferred F, Br, Cl or I), alkyl, alkoxy, aryl, aryloxy, aryl or diaryl substituted by aryl, arylalkyl, arylalkoxy, alkenyl, alkynyl, cycloalkyl, cycloalkenyl, cycloalkylalkyl, cycloalkylalkoxy, optionally substituted amino, hydroxyl, hydroxyalkyl, acyl, aldehyde group, heteroaryl, heteroaryloxy, heterocycloalkyl, heterocycloalkyloxy, arylheteroaryl, arylalkoxycarbonyl, heteroarylalkyl, heteroarylalkoxy, aryloxyalkyl, aryloxyaryl, alkylamino, acylamino, arylcarbonylamino, nitro, cyano, thiol, haloalkyl, trihaloalkyl, and/or alkylthio.

The term "alkylthio" refers to a cyclic or non-cyclic alkyl group containing the indicated number of carbon atoms and having a connection through a sulfur atom. Thus, "alkylthio" includes the definition of "alkyl" and "cycloalkyl".

The term "halogen" refers to fluorine, chlorine, bromine, iodine, or astatine.

The term "haloalkyl" refers to an alkyl group substituted by halogen at optionally position. Thus, "haloalkyl" includes the definition of "halogen" and "alkyl".

The term "haloalkoxy" refers to an alkoxy group substituted by halogen at optionally position. Thus, the "haloalkoxy" includes the definition of "halogen" and "alkoxy".

The term "aryloxy" refers to an aryl group containing the indicated number of carbon atoms and having a connection through an oxygen bridge. Thus, "aryloxy" includes the definition of "aryl".

As used herein, the term "arylhetero" or "heteroaryl" refers to any stable monocyclic or bicyclic ring containing up to 7 atoms in each ring, wherein at least one ring is an aromatic ring containing 1 to 4 heteroatoms selected from the group consisting of O, N, and S. Heteroaryl groups within the scope of this definition include, but are not limited to, acridinyl, carbazolyl, cinnolinyl, quinoxalinyl, pyrazolyl, indolyl, benzotriazolyl, furyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinolinyl. As the heterocycle defined below, "heteroaryl" should also be understood to include the N-oxide derivative of any nitrogen-containing heteroaromatic group. It can be understood that if a heteroaryl substituent is a bicyclic ring having one non-aromatic ring or one ring without heteroatom, then the connection is through the aromatic ring or the heteroatom containing in the ring. Heteroaryl groups are optionally substituted by 1 to 4 substituents selected from the group consisting of deuterium, halogen, alkyl, alkoxy, hydroxyl, aryl, aryloxy, arylalkyl, cycloalkyl, alkylamino, acylamino, acyl, arylcarbonylamino, amino, nitro, cyano, thiol and/or alkylthio and/or any alkyl substituents.

As used herein, the term "heterocycle" or "heterocyclyl" refers to 5 to 10 membered aromatic or non-aromatic heterocyclic ring having 1 to 4 heteroatoms selected from the group consisting of O, N, and S, bicyclic groups are also included. Therefore, the "heterocyclyl" includes the heteroaryl groups, as well as their dihydro or tetrahydro analogs. Other examples of "heterocyclyl" include, but are not limited to, benzimidazolyl, benzofuranyl, benzofurazanyl, benzopyrazolyl, benzotriazolyl, benzothienyl, benzoxazolyl, carbazolyl, carbolinyl, cinnolinyl, furyl, imidazolyl, dihydroindolyl, indolyl, indazolyl, isobenzofuranyl, pseudoindolyl, isoquinoline, isothiazolyl, isoxazolyl, naphthalene pyrimidinyl, oxadiazolyl, oxazolyl, oxazolinyl, isoxazolinyl, oxetanyl, pyranyl, pyrazinyl, pyrazolyl, pyridazinyl, pyridopyridyl pyridazinyl, pyridinyl, pyrimidinyl, pyrrolyl, quinazolinyl, quinolyl, quinoxalinyl, tetrahydropyranyl, tetrazolyl, tetrazopyridyl, thiadiazolyl, thiazolyl, thienyl, triazolyl, azetidinyl, 1,4-dioxanyl, hexahydrodiazepinyl, piperazinyl, piperidinyl, pyrrolidinyl, morpholinyl, thiomorpholinyl, dihydro-benzimidazolyl, dihydro-benzofuranyl, dihydro-benzothienyl, dihydro-benzoxazolyl, dihydrofuryl, dihydro-imidazolyl dihydro-indolyl, dihydro-isoxazolyl, dihydro-isothiazolyl, dihydro-oxadiazolyl, dihydro-oxazolyl, dihydro-pyrazinyl, dihydro-pyrazolyl, dihydropyridyl, dihydro-pyrimidinyl, dihydro-pyrrolyl, dihydro-quinolyl, dihydro-tetrazolyl, dihydro-thiadiazolyl, dihydro-thiazolyl, dihydro-thienyl, dihydro-triazolyl, dihydro-azetidinyl, methylenedioxybenzoyl, tetrahydrofuranyl and tetrahydrothienyl and N-oxides thereof. A heterocyclic group can be linked with other groups through a carbon atom or a heteroatom. As the heterocyclyl is a $C_{2-20}$ heterocyclyl, it is optionally substituted by substituents selected from the group consisting of: halogen, —CN, —CF$_3$, —NO$_2$, oxo, R$^5$, —C(=Y)R$^5$, —C(=Y)OR$^5$, —C(=Y)NR$^5$R$^6$, —(CR$^8$R$^9$)NR$^5$R$^6$, —(CR$^8$R$^9$)$_n$OR$^5$, —NR$^5$R$^6$, —NR$^7$C(=Y)R$^5$, —NR$^7$C(=Y)OR$^6$, —NR$^7$C(=Y)NR$^5$R$^6$, —(CR$^8$R$^9$)$_m$NR$^7$SO$_2$R$^5$, =NR$^7$, OR$^5$, —OC(=Y)R$^5$, —OC(=Y)OR$^5$, —OC(=Y)NR$^5$R$^6$, —OS(O)$_2$(OR$^5$), —OP(=Y)(OR$^5$)(OR$^6$), —OP(OR$^5$)(OR$^6$), —SR$^5$, —S(O)R$^5$, —S(O)$_2$R$^5$, —S(O)$_2$NR$^5$R$^6$, —S(O)(OR$^5$), —S(O)$_2$(OR$^5$), —SC(=Y)R$^5$, —SC(=Y)OR$^5$, —SC(=Y)NR$^5$R$^6$, C$_{1-12}$ alkyl (such as substituted or unsubstituted C$_{1-6}$ alkyl, preferably substituted or unsubstituted C$_{1-3}$ alkyl, whose substituent is preferably a hydroxyl, e.g., together with alkyl form hydroxyethyl, or α-hydroxy isopropyl), C$_{2-8}$ alkenyl, C$_{2-8}$ alkynyl, C$_{3-12}$ carbocyclyl, C$_{2-20}$ heterocyclyl, C$_{6-20}$ aryl or C$_{1-20}$ heteroaryl; other groups and letters have the meanings given above. The C$_{2-20}$ heterocyclyl is preferably a C$_{2-8}$ saturated heterocyclyl, further preferably a C$_{4-5}$ saturated heterocyclyl, wherein the heteroatom is N, O or S, further preferably a C$_{4-5}$ saturated heterocyclyl containing two heteroatoms, such as piperazinyl or piperidinyl. Where the C$_{2-20}$ heterocyclyl has one heteroatom, the substituted position of which is preferably on a carbon atom or a heteroatom; where the C$_{2-20}$ heterocyclyl has two or more heteroatoms, the substituted position of which is preferably on a heteroatom.

The term "heteroalicyclyl" or "heterocycloalkyl" used herein alone or as a part of other groups refers to a 4 to 12 membered saturated or partially unsaturated ring containing 1 to 4 heteroatoms (such as nitrogen, oxygen and/or sulphur). The heterocycloalkyl groups may include 1 to 4 substituents, such as alkyl, halogen, oxo and/or any alkyl substituents set out above. In addition, any heterocycloalkyl rings can be fused to a cycloalkyl, aryl, heteroaryl or heterocycloalkyl ring, and to form a fused ring or a spiro ring. A heterocycloalkyl substituent can be linked with other groups through a carbon atom or a heteroatom.

In the present invention, same substituent labels (such as R$^5$, R$^6$) appeared in the definition of different groups (such as R$^2$ can be —(CR$^8$R$^9$)$_m$NR$^5$R$^6$, R$^4$ also can be —NR$^5$R$^6$) does not mean that they must also be the same specific group, as long as they are all within the scope of their own definition. For example: R$^5$ may be hydrogen, a C$_{1-12}$ alkyl, a C$_{2-8}$ alkenyl, a C$_{2-8}$ alkynyl, a C$_{3-12}$ carbocyclyl, a C$_{2-20}$ heterocyclyl, a C$_{6-20}$ aryl or a C$_{1-20}$ heteroaryl. When R$^2$ is —(CR$^8$R$^9$)$_m$NR$^5$R$^6$, R$^4$ is —NR$^5$R$^6$ and the R$^5$ in R$^2$ is —CF$_3$ or halogen (within the scope of the definition of R$^5$), the R$^5$ in R$^4$ can be —CF$_3$ or halogen, and can also be a C$_{1-12}$ alkyl (all within the scope of the definition of R$^5$).

On the basis of not to violate common sense of the field, all above preferred conditions can be combined in any way to provide the preferred embodiments of the present invention.

The materials and reagents used in the present invention are all commercial available.

The positive effect of the present invention is that: The fused pyrimidine compound I in the present invention is a kind of efficient, low toxicity PI3 kinase inhibitor which can be used for preventing or treating cell proliferation diseases such as cancer, infections, inflammation and autoimmune diseases.

DETAILED DESCRIPTION OF THE PREFERRED EMBODIMENT

Below in conjunction with specific embodiments, the present invention is further elaborated. But the present invention is not therefore limited within the scope of the embodiments. The following embodiment does not indicate the specific conditions of the experiment, usually in accordance with conventional methods and conditions, or product manual.

Synthetic Route of Compound 1

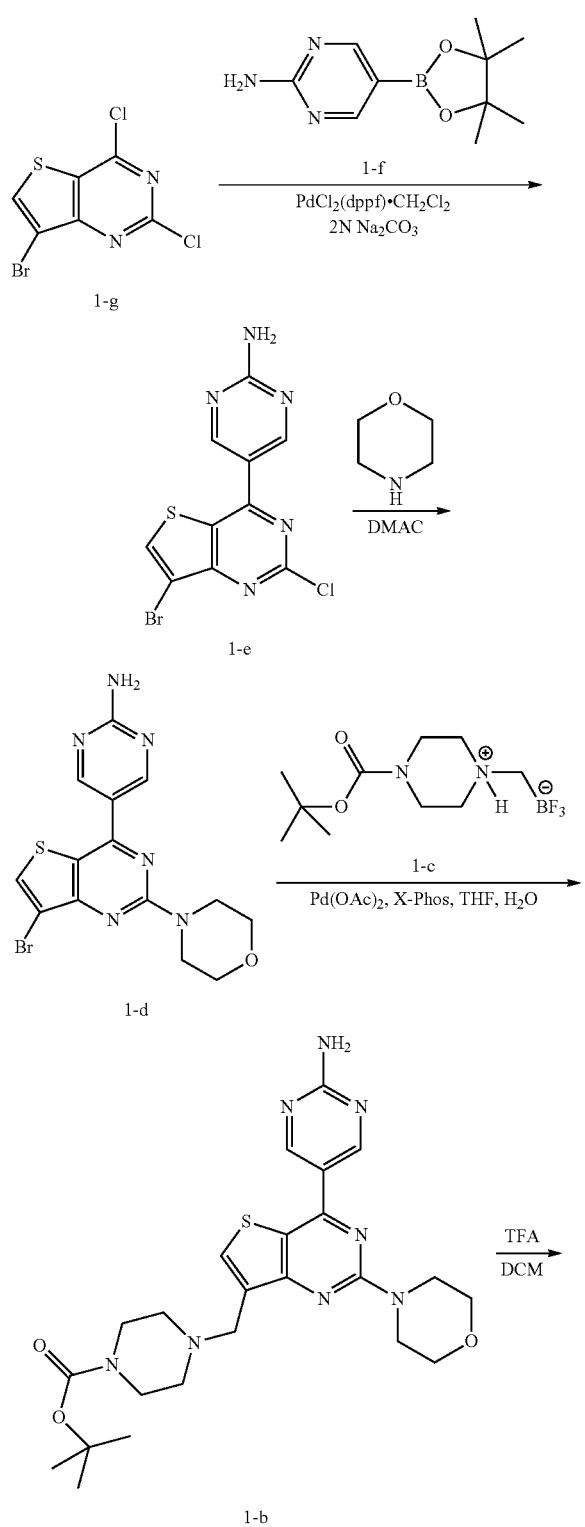

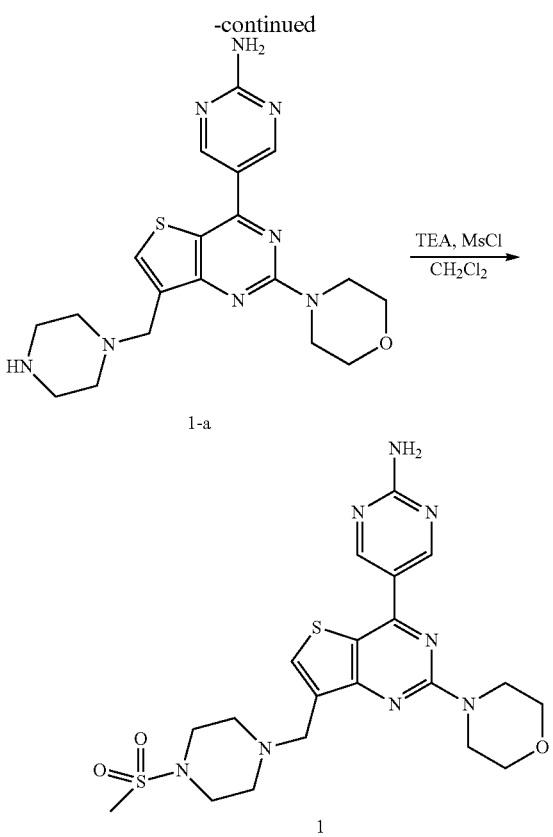

Synthesis of Compound 1-e

To a reaction flask was added compound 1-g (according to the synthesis procedure in the reference: Tetrahedron 2007, 63, 3608-3614) (6.0 g, 21.1 mmol), compound 1-f (4.9 g, 22.2 mmol), 1,4—dioxan (300 mL), aqueous sodium carbonate (2 M, 32 mL, 63.39 mmol), PdCl$_2$(dppf) (1.1 g, 1.48 mmol). The mixture was stirred overnight at 80° C. under nitrogen. After cooling to room temperature, the reaction mixture was diluted with ethyl acetate and water. The organic phase was separated and the aqueous phase was extracted with ethyl acetate. The organic layers were combined, washed successively with water and saturated brine, dried over anhydrous sodium sulfate, filtered, concentrated. The residue was purified by column chromatography (dichloromethane/tetrahydrofuran=25:1 to 10:1) to afford compound 1-e (3.99 g, yield 55%). LC-MS (ESI): m/z=341.9 [M+H]$^+$.

Synthesis of Compound 1-d

To a reaction flask were added 1-e (3.99 g, 11.65 mmol), morpholine (3.4 mL, 23.29 mmol), N,N-dimethylacetamide (DMAC) (60 mL). Under nitrogen, the reaction mixture was stirred overnight at 94° C. In the next day, after cooling to room temperature, water (120 mL) was added. The precipitated solid was filtered, the filter cake was washed with water, dried by coevaporating with toluene, and then recrystallized from 1,4-dioxane to afford compound 1-d (2.3 g, yield 50%) as a yellow solid. LC-MS (ESI): m/z=393.0 [M+H]$^+$. $^1$H NMR (500 MHz, CDCl$_3$): δ 8.99 (s, 2H), 8.52 (s, 1H), 7.45 (s, 2H), 3.86 (t, J=5.0 Hz, 4H), 3.72 (t, J=4.5 Hz, 4H).

Synthesis of Compound 1-b

Compound 1-d (20 mg, 0.05 mmol), compound 1-c (according to the synthesis procedure in the reference: J. Org Chem 2011, 76, 2762-2769) (17 mg, 0.065 mmol), palladium acetate (3 mg, 0.017 mmol), X-phos (14.3 mg, 0.03 mmol) and cesium carbonate (48 mg, 0.15 mmol) were added to a sealed tube containing THF (1.5 mL) and water (0.5 mL). Under nitrogen, the reaction was performed at 80° C. for 24 hours. After cooling, water was added, and the solution was extracted with ethyl acetate. The organic phase was dried over anhydrous sodium sulfate, filtered, and concentrated. The crude product was purified by column chromatography (dichloromethane: methanol=20:1) to give compound 1-b (8 mg, yield 31%) as a white solid. MS (ESI): m/e 513.3(M+H)$^+$.

Synthesis of Compound 1-a

Compound 1-b (20 mg, 0.04 mmol) was dissolved in dichloromethane (2 mL), and then trifluoroacetic acid (2 mL) was added. The reaction mixture was stirred for 30 minutes at room temperature, concentrated. Saturated sodium carbonate solution (10 mL) was added, and the mixture was extracted with ethyl acetate (10 mL×2), dried over anhydrous magnesium sulfate, filtered, and concentrated. The crude product was purified by column chromatography (dichloromethane: methanol=10:1) to give compound 1-a (12 mg, yield 73%) as a white solid. MS (ESI): m/e 413.2 (M+H)$^+$. $^1$H NMR (500 MHz, DMSO-$d_6$): δ 9.00 (s, 2H), 8.12 (s, 1H), 7.40 (s, 2H), 3.82 (t, 4H), 3.75 (s, 2H), 3.71 (t, 4H), 2.85 (d, 4H), 2.49 (d, 4H).

Synthesis of Compound 1

Compound 1-a (60 mg, 0.145 mmol) was dissolved in dichloromethane (10 mL) and DMF (5 mL), and to the solution were added triethylamine (0.174 mmol) and methanesulfonyl chloride (0.174 mmol) sequentially. The reaction mixture was stirred at room temperature for 30 minutes, concentrated and the crude product was purified by column chromatography (dichloromethane: methanol=20:1) to afford compound 1 (20 mg, yield 28%) as a white solid. MS (ESI): m/e 413.2 (M+H)$^+$. $^1$H NMR (500 MHz, CDCl$_3$): δ 9.05 (s, 2H), 7.68 (s, 1H), 5.32 (s, 2H), 3.86 (t, 4H), 3.79 (s, 2H), 3.77 (t, 4H), 3.20 (d, 4H), 2.71 (s, 3H), 2.62 (d, 4H).

Synthetic Route of Compound 2

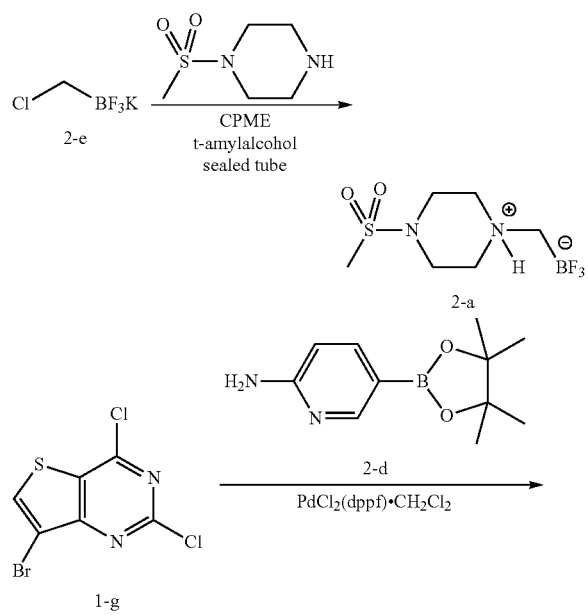

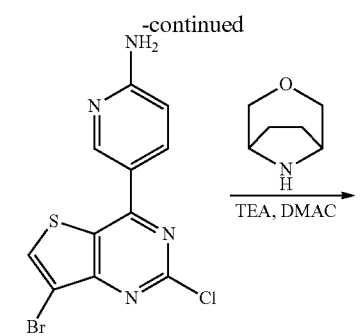

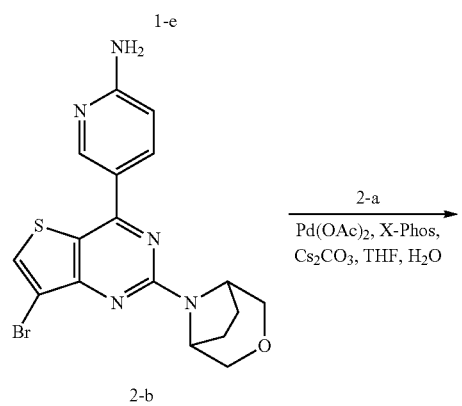

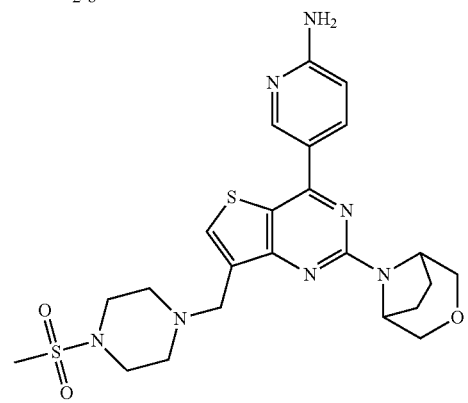

Synthesis of Compound 2-a

To a sealed tube were added compound 2-e (according to the synthesis procedure in the reference: J. Org Chem 2011, 76, 2762-2769) (2.2 g, 14.1 mmol), 1-methanesulfonyl-piperazine (2.27 g, 14.2 mmol), a mixture of cyclopentyl methyl ether (CPME) and t-butanol (3/1, v/v, 12 mL). The reaction mixture was stirred overnight at 110° C. under nitrogen. In the next day, the reaction mixture was concentrated, and acetone (100 mL) was added. After refluxing, the mixture was filtered to remove potassium chloride. The filtrate was concentrated and the residue was dissolved in acetone (15 mL), and diethyl ether was slowly added (30 mL) to make precipitation, more ether (150 mL) was added. After filtering, the filter cake was dried to give compound 2-a (3.2 g, yield 71%). $^1$H NMR (500 MHz, CDCl$_3$): δ 8.85 (s, 1H), 3.59 (d, J=12.5 Hz, 2H), 3.41 (d, J=12.0 Hz, 2H), 3.11 (t, J=11.5 Hz, 2H), 2.87-3.07 (m, 2H), 2.96 (s, 3H).

Synthesis of Compound 2-c

Compound 1-g (400 mg, 1.41 mmol), compound 1-d (310 mg, 1.41 mmol), PdCl$_2$(dppf).CH$_2$Cl$_2$ (114 mg, 0.14 mmol), 2 N sodium carbonate solution (2.1 mL) were added to a flask containing dioxane (10 mL). The reaction mixture was stirred overnight at 80° C. under nitrogen, water (100 mL) was added, and the solution was extracted with ethyl acetate (100 mL). The organic phase was dried over anhydrous sodium sulfate, filtered, and concentrated. The residue was purified by column chromatography (dichloromethane: methanol=100:1) to give compound 2-c (133 mg, yield 20%) as a yellow solid. LC-MS (ESI): m/e 343.0 (M+H)+.

Synthesis of Compound 2-b

To a reaction flask were added compound 2-c (100 mg, 0.29 mmol), 3-oxa-8-azabicyclo[3.2.1]octane hydrochloride (52 mg, 0.35 mmol), N,N-dimethylacetamide (50 mL), and triethylamine (0.1 mL, 0.64 mmol). Under nitrogen, the reaction mixture was stirred overnight at 94° C. After cooling to room temperature, water (5 mL) was added. The precipitated solid was filtered, the filter cake was washed with water, dried, and the resulting solid was purified by column chromatography (tetrahydrofuran: dichloromethane=10:1) to give compound 2-b (45 mg, yield 37%) as a yellow solid. LC-MS (ESI): m/z 418.0 (M+H)+.

Synthesis of Compound 2

To a microwave tube were added compound 2-b (10 mg, 0.0024 mmol), compound 2-a (12 mg, 0.048 mmol), cesium carbonate (23 mg, 0.072 mmol), x-Phos (4 mg, 0.008 mmol), palladium acetate (4 mg, 0.018 mmol), and a mixture of tetrahydrofuran and water (10/1, v/v, 1 mL). Under nitrogen, the mixture was stirred for 1.5 hours under microwave at 80° C., 150 W. The reaction was cooled to room temperature, filtered, the filter cake was washed with tetrahydrofuran. The filtrate and washings were combined, concentrated and purified by preparative TLC to give compound 2 (7 mg, yield 56%). LC-MS (ESI): m/z 516.2 (M+H)+. 1H NMR (500 MHz, CDCl3): δ 8.93 (1H, d, J=2.0 Hz), 8.26 (1H, dd, J=2.0, 8.5 Hz), 7.73 (1H, s), 6.63 (1H, d, J=8.5 Hz), 4.73-4.91 (4H, m), 3.88 (2H, d, J=10.5 Hz), 3.86 (2H, s), 3.65-3.72 (2H, m), 3.22-3.31 (4H, m), 2.77 (3H, s), 2.70 (4H, t, J=5.0 Hz), 2.08-2.15 (2H, m), 1.95-2.06 (2H, m).

Synthetic Route of Compound 3

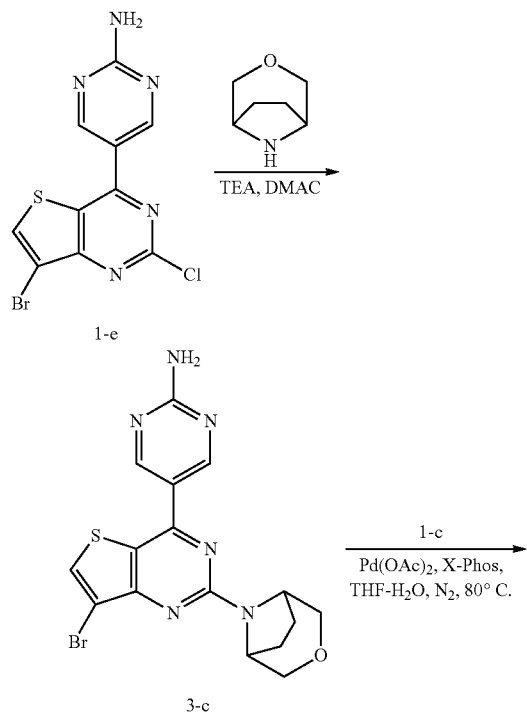

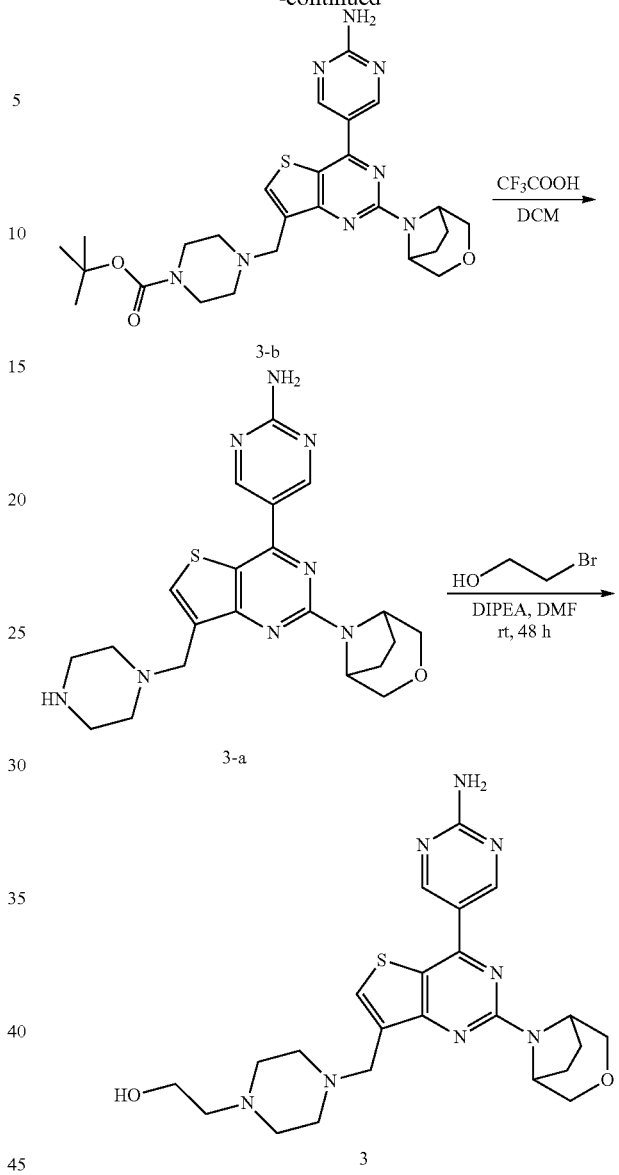

Synthesis of Compound 3-c

To a reaction flask were added compound 1-e (3.91 g, 11.4 mmol), 3-oxa-8-azabicyclo[3.2.1]octane hydrochloride (1.8 g, 12.0 mmol), N,N-dimethylacetamide (60 mL), triethylamine (3.2 mL, 22.8 mmol). Under nitrogen, the reaction mixture was stirred for two days at 94° C. The reaction mixture was cooled to room temperature, water (120 mL) was added. The precipitated solid was filtered, the filter cake was washed with water, and dried. The filtrate was extracted with ethyl acetate. The ethyl acetate phase was washed successively with water and saturated brine, dried over anhydrous sodium sulfate, filtered, concentrated, and combined with the filter cake, and purified by column chromatography (dichloromethane/methanol=200:1 to 25:1), and then recrystallized from 1,4-dioxane to afford compound 3-c (2.2 g, yield 46%) as a yellow solid. LC-MS (ESI): m/z 419.0 [M+H]+. 1H NMR (500 MHz, CDCl3): δ 9.09 (s, 2H), 7.84 (s, 1H), 5.44 (s, 2H), 4.90 (s, 2H), 3.88 (d, J=11.0 Hz, 2H), 3.66-3.73 (m, 2H), 2.11-2.17 (m, 2H), 1.99-2.10 (m, 2H).

Synthesis of Compound 3-b

Compound 3-c (200 mg, 0.48 mmol), compound 1-c (193 mg, 0.72 mmol), palladium acetate (12 mg, 0.04 mmol), X-phos (24 mg, 0.05 mmol) and cesium carbonate (468 mg, 1.44 mmol) were added to a reaction tube having tetrahydrofuran (2.0 mL) and water (0.2 mL). Under nitrogen, the reaction mixture was stirred overnight at 80° C. The reaction mixture was cooled, filtered and washed with tetrahydrofuran, and concentrated. The crude product was purified by HPLC to give compound 3-b (200 mg, yield 78%) as a yellow solid. LC-MS (ESI): m/z 539.3 (M+H)$^+$.

Synthesis of Compound 3-a

Compound 3-b (200 mg, 0.37 mmol) was dissolved in dichloromethane (15 mL), then 2.6 M trifluoroacetic acid/dichloromethane (15 mL) was added slowly, and the reaction mixture was stirred at room temperature for 1 hour. Then the reaction mixture was concentrated and saturated sodium carbonate solution (15 mL) was added. After stirring for 5 minutes at room temperature, the mixture was extracted with ethyl acetate (15 mL×3), the organic phase was dried over anhydrous magnesium sulfate, filtered, and concentrated to give compound 3-a (126 mg, yield 78%) as a yellow solid. LC-MS (ESI): m/z 439.2 (M+H)$^+$.

Synthesis of Compound 3

Compound 3-a (40 mg, 0.09 mmol) was dissolved in DMF (2 mL), to the mixture were added bromoethanol (17 μL, 0.18 mmol) and diisopropyl ethyl amine (0.36 mmol). The reaction mixture was stirred at room temperature for 48 hours and directly purified by HPLC to give compound 3 (34 mg, yield 79%) as a yellow solid. LC-MS (ESI): m/z 483.3 (M+H)$^+$. $^1$H NMR (500 MHz, acetone-d$_6$): δ 9.07 (s, 2H), 7.99 (s, 1H), 6.65 (s, 2H), 4.86 (s, 2H), 3.81 (s, 1H), 3.79 (s, 3H), 3.64 (d, 2H, J=11.5 Hz), 3.56 (t, 2H, J=6.0 Hz), 2.56-2.50 (m, 8H), 2.46 (t, 2H, J=6.0 Hz), 2.08 (t, 2H, J=5.0 Hz), 1.99 (t, 2H, J=5.0 Hz).

Synthetic Route of Compound 4

Synthesis of Compound 4-a

To the reaction tube were added compound 2-e (0.5 g, 3.2 mmol), 2-(4-piperidinyl)-2-propanol (0.46 g, 3.23 mmol), cyclopentyl methyl ether (2.1 mL), t-amyl alcohol (0.7 mL). Under nitrogen, the reaction mixture was stirred overnight at 110° C. In the next day, the reaction mixture was concentrated. Acetone (6 mL) was added. After refluxing, diethyl ether (10 mL) was added slowly to make precipitated, more ether (90 mL) was added. After cooling to room temperature, the mixture was filtered, the filter cake was dried to give compound 4-a (0.77 g, yield 100%). $^1$H NMR (500 MHz, DMSO-d$_6$): δ 9.19 (s, 1H), 4.25 (s, 1H), 3.38 (d, J=12.5 Hz, 2H), 2.67 (t, J=12.5 Hz, 2H), 1.90 (d, J=5.0 Hz, 2H), 1.74 (d, J=13.5 Hz, 2H), 1.44-1.57 (m, 2H), 1.36 (t, J=12.0 Hz, 1H), 1.02 (s, 6H).

Synthesis of Compound 4

To a microwave reaction tube were added compound 3-c (0.1 g, 0.24 mmol), compound 4-a (0.108 g, 0.36 mmol), cesium carbonate (0.233 g, 0.72 mmol), x-Phos (0.012 g, 0.03 mmol), palladium acetate (0.01 g, 0.05 mmol), a mixture of tetrahydrofuran and water (10/1, v/v, 1.1 mL). Under nitrogen, the mixture was stirred under microwave irradiation at 125° C., 150 W, for 1 hour. The reaction mixture was cooled to room temperature, filtered. The filter cake was washed with tetrahydrofuran. The filtrate and washings were combined, concentrated and purified by preparative HPLC to give compound 4 (20 mg, yield 17%). LC-MS (ESI): m/z 496.2 (M+H)$^+$. $^1$H NMR (500 MHz, DMSO-d$_6$): δ 8.99 (s, 2H), 8.06 (s, 1H), 7.38 (s, 2H), 4.76 (s, 2H), 4.01 (s, 1H), 3.64-3.73 (m, 4H), 3.61 (d, J=11.5 Hz, 2H), 2.98 (d, J=10.5 Hz, 2H), 1.85-2.03 (m, 6H), 1.63 (d, J=12.5 Hz, 2H), 1.18-1.31 (m, 2H), 1.05-1.16 (m, 1H), 1.01 (s, 6H).

Synthetic Route of Compound 5

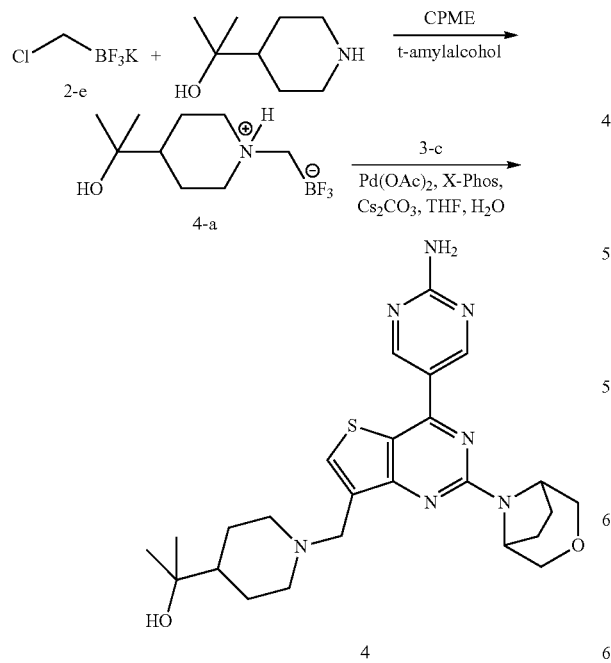

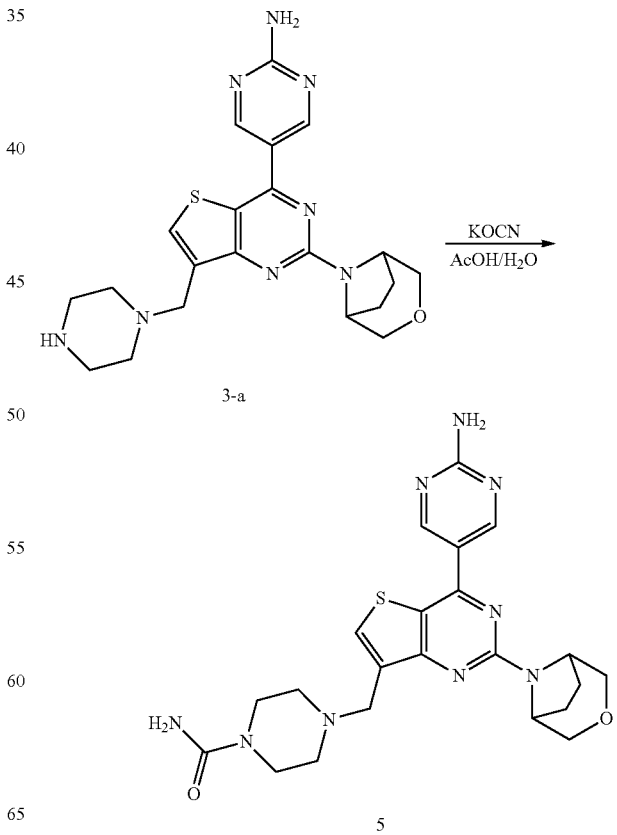

Synthesis of Compound 5

To the solution of compound 3-a (40 mg, 0.09 mmol) in water (1 mL) and acetic acid (0.6 mL) was added a solution of potassium cyanate (371 mg, 0.45 mmol) in water (1 mL). The reaction mixture was stirred overnight at room temperature, water (2 mL) was added, extracted with ethyl acetate (5 mL×3). The organic phase was dried over anhydrous sodium sulfate, filtered, and concentrated. The crude product was purified by HPLC to give compound 5 (14 mg, yield 33%) as a yellow solid. LC-MS (ESI): m/z 482.2 (M+H)+. $^1$H NMR (500 MHz, DMSO-$d_6$): δ 8.98 (s, 2H), 8.12 (s, 1H), 7.38 (s, 2H), 5.90 (s, 2H), 4.76 (s, 2H), 3.76 (s, 2H), 3.71 (d, 2H, J=10.5 Hz), 3.62 (d, 2H, J=10.5 Hz), 3.27 (t, 4H, J=4.5 Hz), 2.40 (t, 4H, J=4.5 Hz), 1.99 (t, 2H, J=5.0 Hz), 1.92 (t, 2H, J=4.5 Hz).

Synthetic Route of Compound 6

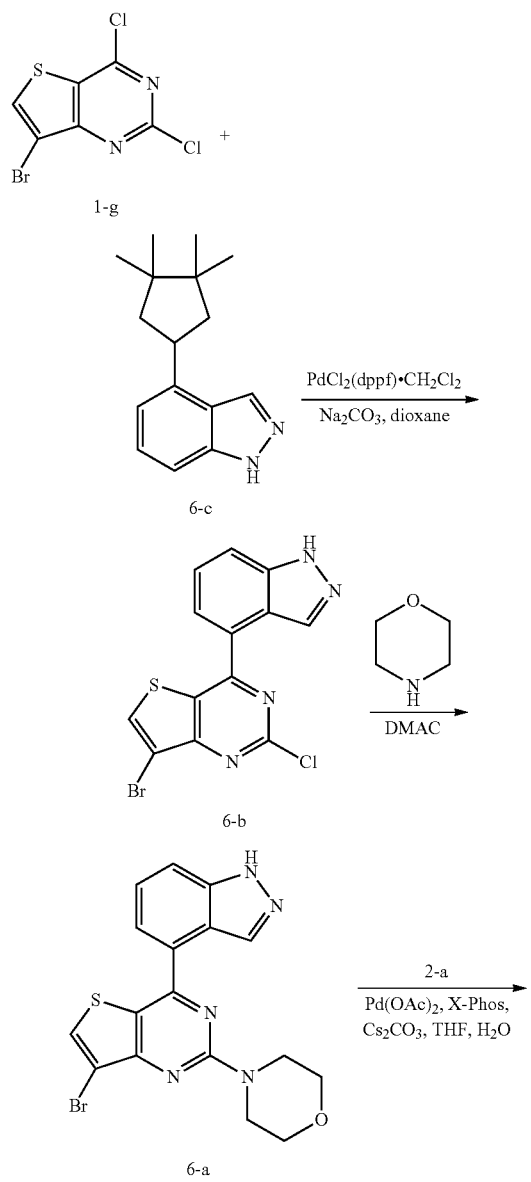

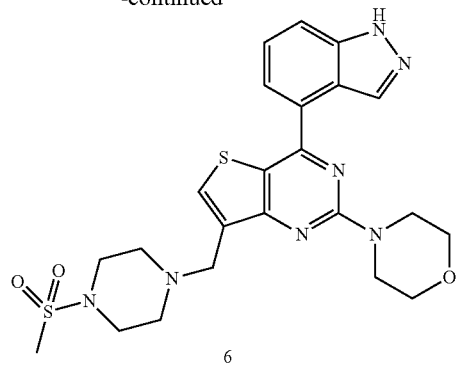

Synthesis of Compound 6-b

To a flask containing dioxane (25 mL) were added compound 6-c (439 mg, 1.8 mmol), compound 1-g (338 mg, 1.2 mmol), PdCl$_2$(dppf)$_2$ (98 mg, 0.12 mmol), aqueous sodium carbonate (2 M, 2.5 mL). Under nitrogen, the reaction mixture was stirred overnight at 80° C. After completion, the reaction mixture was cooled, water (50 mL) was added, then extracted with ethyl acetate (50 mL×3). The organic phase was dried over anhydrous magnesium sulfate, filtered, and concentrated. The residue was purified by column chromatography (petroleum ether: ethyl acetate=3: 1:1) to give compound 6-b (220 mg, yield 51%) as a yellow solid. LC-MS (ESI): m/z 364.9 (M+H)+.

Synthesis of Compound 6-a

To a flask were added 6-b (173 mg, 0.48 mmol), morpholine (1.05 mmol) and N,N-dimethylacetamide (10 mL). Under nitrogen, the reaction mixture was stirred overnight at 94° C. After cooling to room temperature, water (14 mL) was added, and extracted with ethyl acetate (20 mL×3). The organic phase was dried over anhydrous magnesium sulfate, filtered, and concentrated. The residue was purified by column chromatography (petroleum ether: tetrahydrofuran=4:1 to 2:1) to give compound 6-a (137 mg, yield 70%) as a yellow solid. LC-MS (ESI): m/z 416.0 (M+H)+.

Synthesis of Compound 6

To a microwave tube were added compound 6-a (37 mg, 0.09 mmol), compound 2-a (45 mg, 0.18 mmol), cesium carbonate (88 mg, 0.18 mmol), x-Phos (5 mg, 0.009 mmol), palladium acetate (3 mg, 0.009 mmol), a mixture of tetrahydrofuran and water (10/1, v/v, 1.1 mL). Under nitrogen, the reaction mixture was stirred with microwave irradiation, 125° C., 150 W, for 1 hour. After cooling to room temperature, the reaction mixture was filtered, the filter cake was washed with tetrahydrofuran. The filtrate and washings were combined, concentrated and the residue was purified by preparative TLC to afford compound 6 (6 mg, 13% yield). LC-MS (ESI): m/z 514.2 (M+H)+. $^1$H NMR (500 MHz, CDCl$_3$): δ 8.61 (s, 1H), 7.92 (d, 1H, J=6.5 Hz), 7.79 (s, 1H), 7.68 (d, 1H, J=8.0 Hz), 7.58 (t, 1H, J=7.5 Hz), 3.98 (s, 4H), 3.91 (s, 2H), 3.86 (s, 4H), 3.30 (s, 4H), 2.78 (s, 3H), 2.74 (s, 4H).

Synthetic Route of Compound 7

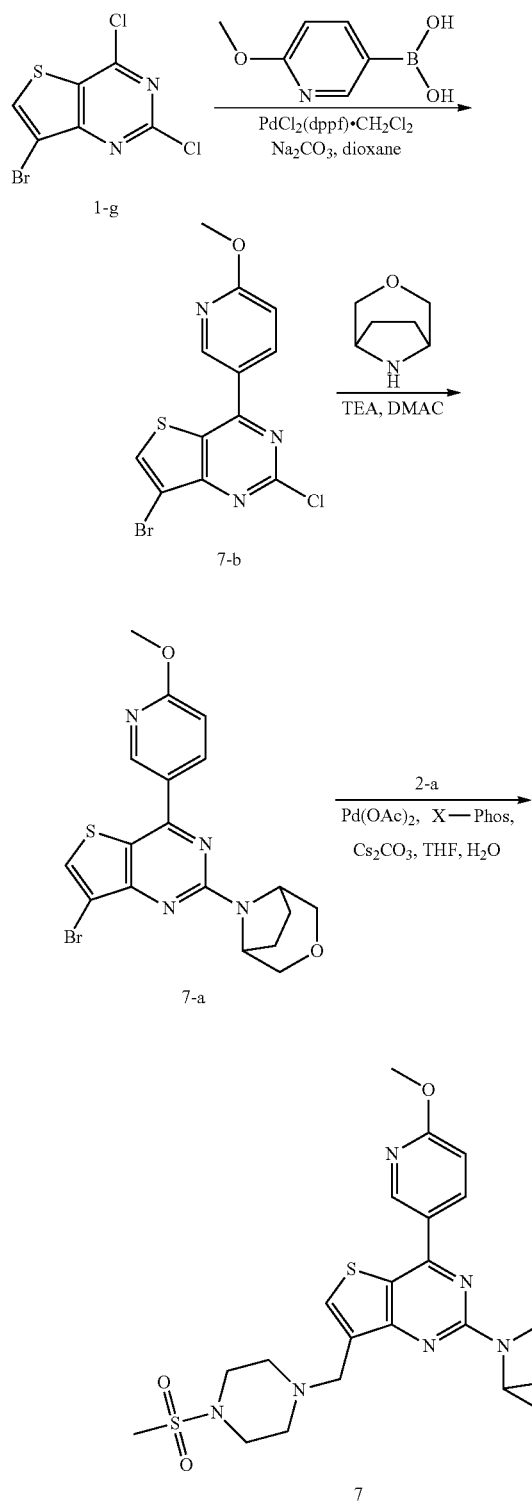

Synthesis of Compound 7-b

To a flask containing dioxane (16 mL) were added compound 1-g (400 mg, 1.41 mmol), 2-Methoxy-pyridine 5-boronic acid (236 mg, 1.55 mmol), PdCl$_2$(dppf)·CH$_2$Cl$_2$ (115 mg, 0.14 mmol), sodium carbonate solution (2 M, 2.1 mL). Under nitrogen, the reaction mixture was stirred at 80° C. overnight. Water (50 mL) was added, and the solution was extracted with ethyl acetate (50 mL). The organic phase was dried over anhydrous sodium sulfate, filtered, and concentrated. The residue was purified by column chromatography (petroleum ether: ethyl acetate=30:1) to give compound 7-b (235 mg, yield 49%) as a yellow solid. LC-MS (ESI): m/e 355.9 (M+H)$^+$.

Synthesis of Compound 7-a

To a reaction flask were added compound 7-b (235 mg, 0.66 mmol), 3-oxa-8-azabicyclo[3.2.1]octane hydrochloride (118 mg, 0.79 mmol), N,N-dimethylacetamide (8 mL), triethylamine (0.12 mL, 200 mg, 1.98 mmol). Under nitrogen, the reaction mixture was heated to 94° C., and stirred for 24 hours, diluted with water (20 mL), stirred at room temperature for 30 minutes. The precipitated yellow solid was filtered, the filter cake was purified by column chromatography (petroleum ether: ethyl acetate=20:1) to give compound 7-a (171 mg, yield 60%) as a yellow solid. LC-MS (ESI): m/e 434.0(M+H)$^+$.

Synthesis of Compound 7

To a reaction tube containing tetrahydrofuran (2 mL) and water (0.2 mL) were added compound 7-a (171 mg, 0.395 mmol), compound 2-a (117 mg, 0.47 mmol), palladium acetate (18 mg, 0.08 mmol), X-phos (19 mg, 0.04 mmol), cesium carbonate (0.569 g, 1.19 mmol). Under nitrogen, the reaction mixture was sealed and stirred overnight at 80° C. After cooling, the reaction mixture was filtered through celite, washed with tetrahydrofuran. The filtrate and washings were combined and concentrated. The residue was purified by Prep-HPLC to give compound 7 (45 mg, yield 22%) as a yellow solid. LC-MS (ESI): m/e 531.2 (M+H)$^+$. $^1$H NMR (500 MHz, CDCl$_3$): δ 9.02(s, 1H), 8.37(d, 1H), 7.75(s, 1H), 6.91(d, 1H), 4.86(s, 2H), 4.04(s, 3H), 3.88(d, 4H), 3.68(d, 2H), 3.27(s, 4H), 2.78(s, 3H), 2.71-2.69(m, 4H), 2.13(d, 2H), 2.04-2.02(m, 2H).

Synthetic Route of Compound 8

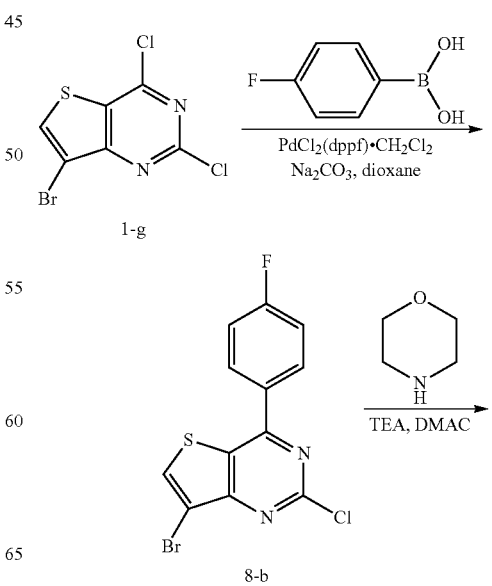

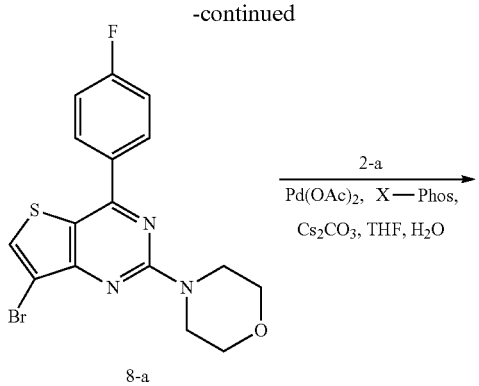

125° C. and stirred for 1 hour under nitrogen atmosphere. The reaction mixture was diluted with tetrahydrofuran, filtered and the filtrate was concentrated. The residue was purified by HPLC to afford compound 8 (77 mg, 55% yield). LC-MS (ESI): m/z 492.1 (M+H)+. $^1$H NMR (500 MHz, CDCl$_3$): δ 8.17-8.14 (m, 2H), 7.75 (s, 1H), 7.26 (dd, J=16.5, 8.0 Hz, 2H), 3.95 (t, J=5.0 Hz, 4H), 3.87 (s, 2H), 3.85 (t, J=5.0 Hz, 4H), 3.28 (t, J=5.0 Hz, 4H), 2.77 (s, 3H), 2.71 (t, J=5.0 Hz, 4H).

Synthetic Route of Compound 9

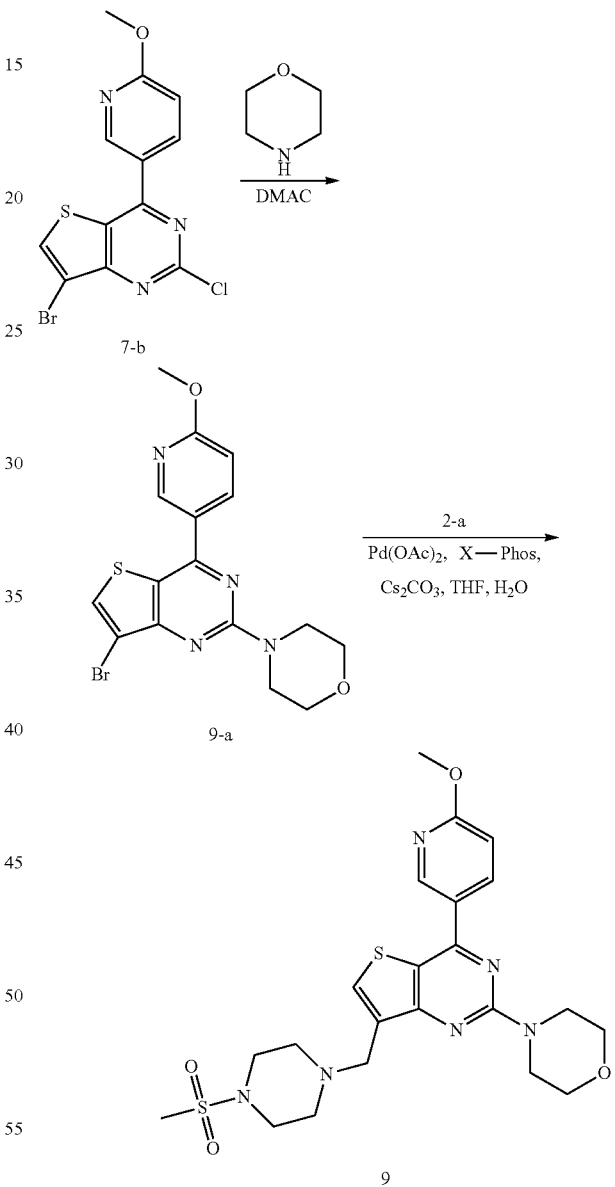

Synthesis of Compound 8-b

To a flask containing dioxane (25 mL) were added compound 1-g (350 mg, 1.24 mmol), 4-fluorophenyl boronic acid (208 mg, 1.48 mmol), PdCl$_2$(dppf)$_2$ (100 mg, 0.12 mmol), aqueous sodium carbonate (2 M, 2.5 mL). Under nitrogen, the reaction mixture was stirred overnight at 80° C. After cooling, water (50 mL) was added, and the solution was extracted with ethyl acetate (50 mL×3). The organic layers were dried over anhydrous magnesium sulfate, filtered, and concentrated. The residue was purified by column chromatography (petroleum ether: ethyl acetate=3:1 to 1:1) to give compound 8-b (336 mg, 83% yield) as a yellow solid. LC-MS (ESI): m/z 342.9 (M+H)+.

Synthesis of Compound 8-a

A mixture of compound 8-b (356 mg, 1.04 mmol), morpholine (0.3 mL, 3.12 mmol) and N N-dimethylacetamide (15 mL) was heated to 95° C. and stirred overnight. After cooling to room temperature, the reaction mixture was concentrated and the residue was diluted with ethyl acetate, washed successively with water and saturated brine. The organic phase was dried over anhydrous sodium sulfate, concentrated. The residue was purified by column chromatography (petroleum ether: ethyl acetate acetate=2:1) to give compound 8-a (120 mg, 30% yield). LC-MS (ESI): m/z 396.0 (M+H)+.

Synthesis of Compound 8

A mixture of compound 8-a (120 mg, 0.31 mmol), compound 2-a (153 mg, 0.62 mmol), palladium acetate (10 mg, 0.05 mmol), X-Phos (10 mg, cat), cesium carbonate (302 mg, 0.93 mmol), tetrahydrofuran (1.4 mL) and water (0.3 mL) was placed into a microwave apparatus and heated to Synthesis of Compound 9-a Compound 7-b (211 mg, 0.59 mmol) and morpholine (129 mg, 1.48 mmol) were dissolved in DMAC (5 mL), the mixture was heated to 94° C. and stirred for 24 hours under nitrogen. The reaction mixture was diluted with water (50 mL), extracted with ethyl acetate (50 mL). The organic phase was washed with water and saturated brine, dried over anhydrous sodium sulfate, filtered, and concentrated. The residue was purified by column chromatography (petroleum ether: ethyl acetate=20:1) to give compound 9-a (134 mg, yield 56%) as a yellow solid. LC-MS (ESI): m/e 407.0 (M+H)⁺.

Synthesis of Compound 9

To a microwave tube containing tetrahydrofuran (2 mL) and water (0.2 mL) were added compound 9-a (134 mg, 0.33 mmol), compound 2-a (81.6 mg, 0.40 mmol), palladium acetate (15 mg, 0.07 mmol), X-phos (15.8 mg, 0.03 mmol), and cesium carbonate (323 mg, 0.99 mmol). Under nitrogen, the mixture was sealed and stirred overnight at 80° C. After cooling, the reaction mixture was filtered through celite, washed with tetrahydrofuran. The filtrate and washings were combined and concentrated. The residue was purified by Prep-HPLC to give compound 9 (10 mg, 6%) as a yellow solid. LC-MS (ESI): m/e 505.1 (M+H)⁺. $^1$H NMR (500 MHz, CDCl$_3$): δ 9.03 (s, 1H), 8.39 (d, 1H), 7.76 (s, 1H), 6.91 (d, 1H), 4.04 (s, 3H), 3.95-3.93 (m, 4H), 3.88 (d, 2H), 3.85-3.83 (m, 4H), 3.29-3.27 (m, 4H), 2.78 (s, 3H), 2.72-2.70 (m, 4H).

Synthetic Route of Compound 10

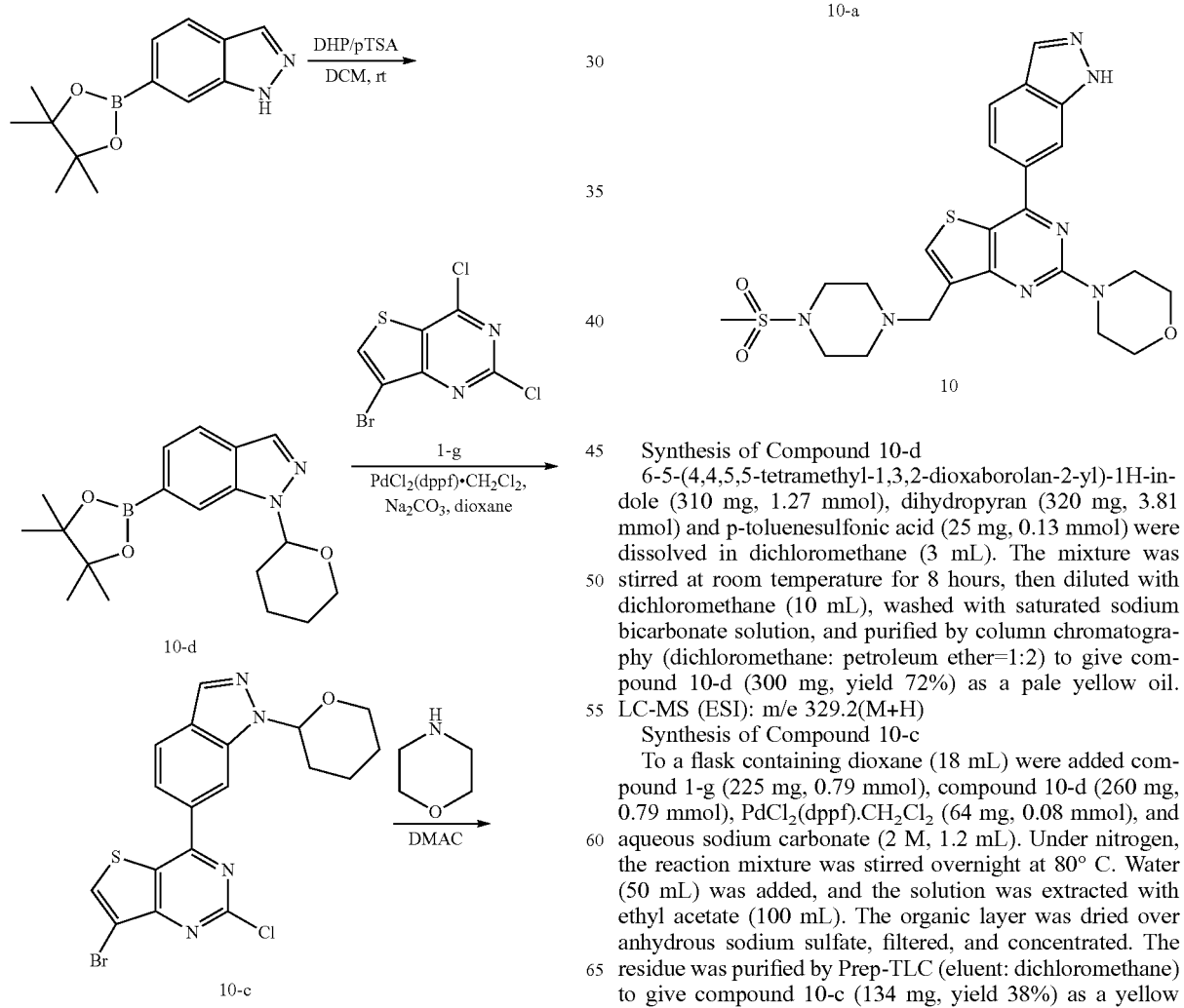

Synthesis of Compound 10-d 6-5-(4,4,5,5-tetramethyl-1,3,2-dioxaborolan-2-yl)-1H-indole (310 mg, 1.27 mmol), dihydropyran (320 mg, 3.81 mmol) and p-toluenesulfonic acid (25 mg, 0.13 mmol) were dissolved in dichloromethane (3 mL). The mixture was stirred at room temperature for 8 hours, then diluted with dichloromethane (10 mL), washed with saturated sodium bicarbonate solution, and purified by column chromatography (dichloromethane: petroleum ether=1:2) to give compound 10-d (300 mg, yield 72%) as a pale yellow oil. LC-MS (ESI): m/e 329.2(M+H)

Synthesis of Compound 10-c

To a flask containing dioxane (18 mL) were added compound 1-g (225 mg, 0.79 mmol), compound 10-d (260 mg, 0.79 mmol), PdCl$_2$(dppf).CH$_2$Cl$_2$ (64 mg, 0.08 mmol), and aqueous sodium carbonate (2 M, 1.2 mL). Under nitrogen, the reaction mixture was stirred overnight at 80° C. Water (50 mL) was added, and the solution was extracted with ethyl acetate (100 mL). The organic layer was dried over anhydrous sodium sulfate, filtered, and concentrated. The residue was purified by Prep-TLC (eluent: dichloromethane) to give compound 10-c (134 mg, yield 38%) as a yellow solid. LC-MS (ESI): m/e 449.8(M+H)⁺.

Synthesis of Compound 10-b

Compound 10-c (134 mg, 0.30 mmol) and morpholine (65 mg, 0.75 mmol) were dissolved in DMAC (5 mL). The mixture was heated to 94° C., stirred overnight under nitrogen. The mixture was diluted with water (50 mL), extracted with ethyl acetate. The organic phase was washed with water and saturated brine, dried over anhydrous sodium sulfate, filtered, and concentrated. The residue was purified by Prep-TLC (eluent: dichloromethane) to give compound 10-b (105 mg, yield 70%) as a yellow solid. LC-MS (ESI): m/e 500.1(M+H)$^+$.

Synthesis of Compound 10-a

To a reaction tube containing tetrahydrofuran (3 mL) and water (0.3 mL) were added compound 10-b (105 mg, 0.21 mmol), compound 2-a (104 mg, 0.42 mmol), palladium acetate (10.1 mg, 0.07 mmol), X-phos (10.1 mg, 0.04 mmol), and cesium carbonate (205 mg, 0.63 mmol). Under nitrogen, the tube was sealed, and the mixture was stirred overnight at 80° C. After cooling, the reaction mixture was filtered through celite, washed with tetrahydrofuran. The filtrate and washings were combined and concentrated. The residue was purified by Prep-TLC (methylene chloride:methanol=50:1) to give compound 10-a (67 mg, 53% yield) as a yellow solid.

LC-MS (ESI): m/e 598.2(M+H)$^+$

Synthesis of Compound 10

To a round bottom flask containing methanol (3 mL) and water (1 mL) was added compound 10-a (67 mg, 0.11 mmol), then methanesulfonic acid (54 mg, 0.56 mmol) was added under nitrogen. The mixture was stirred at room temperature for 1 hour, and then warmed to 65° C., stirred for another 16 hours. The reaction solution was washed with saturated sodium bicarbonate solution to pH 7~8. Water (20 mL) was added, and the solution was extracted with ethyl acetate (20 mL). The organic phase was dried over anhydrous sodium sulfate, filtered, and concentrated. The residue was purified by Prep-TLC (methylene chloride: methanol=20:1) to give compound 10 (40 mg, 70% yield). LC-MS (ESI): m/e 514.2 (M+H)$^+$. $^1$H NMR (500 MHz, CDCl$_3$): δ 10.9(s, 1H), 8.15(s, 1H), 7.96(s, 1H), 7.93-7.89(m. 2H), 7.78(s, 1H), 3.90(s, 2H), 3.86-3.84(m, 4H), 3.76-3.74(m, 4H), 3.33-3.31(m. 4H), 2.770, 2.77-2.75(m, 7H).

Synthetic Route of Compound 11

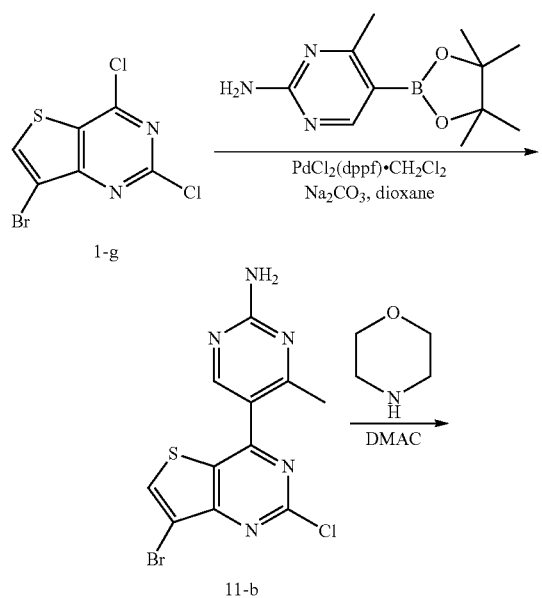

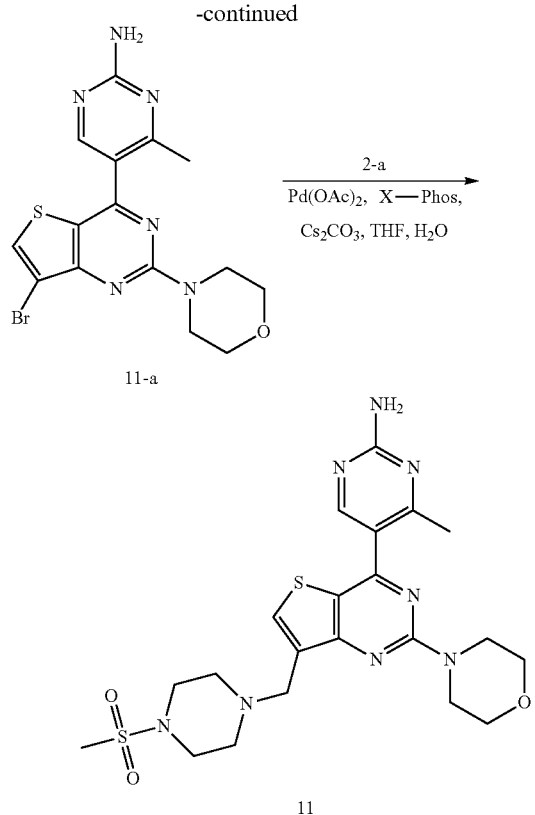

Synthesis of Compound 11-b

To a reaction flask were added compound 1-g (200 mg, 0.70 mmol), 4-methyl-5-(4,4,5,5-tetramethyl-1,3,2-dioxaborolan-2-yl)pyrimidin-2-amine (174 mg, 0.74 mmol), 1,4-dioxane (10 mL), aqueous sodium carbonate (2 M, 1 mL, 2.0 mmol) and PdCl$_2$(dppf) (51 mg, 0.07 mmol). The mixture was stirred overnight at 80° C. under nitrogen atmosphere. In the next day, after cooling to room temperature, the reaction mixture was diluted with ethyl acetate and water. The organic phase was separated and the aqueous phase was extracted with ethyl acetate. The combined organic layers were washed successively with water and saturated brine, dried over anhydrous sodium sulfate, filtered, concentrated. The residue was purified by column chromatography (dichloromethane/tetrahydrofuran=25:1 to 10:1) to give compound 11-b (111 mg, 44% yield). MS (ESI): m/z 356 (M+H)$^+$.

Synthesis of Compound 11-a

Compound 11-b (90 mg, 0.25 mmol) and morpholine (56 mg, 0.63 mmol) were dissolved in DMAC (5 mL). The mixture was heated to 94° C. and stirred overnight under nitrogen. The reaction mixture was diluted with water (50 mL), and extracted with ethyl acetate (50 mL). The organic phase was washed with water and saturated brine, dried over anhydrous sodium sulfate, filtered, and concentrated. The residue was purified by Prep-TLC (eluent: dichloromethane) to give compound 11-a (90 mg, 87% yield) as a yellow solid. LC-MS (ESI): m/e 407.0(M+H)$^+$.

Synthesis of Compound 11

To a reaction tube containing tetrahydrofuran (3 mL) and water (0.3 mL) were added compound 11-a (90 mg, 0.22 mmol), compound 2-a (109 mg, 0.44 mmol), palladium acetate (10 mg, 0.044 mmol), X-phos (10.6 mg, 0.042 mmol) and cesium carbonate (0.216 g, 0.64 mmol). Under nitrogen, the reaction mixture was sealed and stirred overnight in an oil bath at 80° C. After cooling, the reaction mixture was filtered through celite, washed with tetrahydrofuran. The filtrate and washings were combined and concentrated. The residue was purified by Prep-TLC (methylene chloride: methanol=35:1) followed by Prep-HPLC to afford compound 11 (28 mg, yield 25%) as a white solid. LC-MS (ESI): m/e 505.2 (M+H)$^+$. $^1$H NMR (500 MHz, CDCl$_3$): δ 8.53(s, 1H), 7.74(s, 1H), 5.24(s, 2H), 3.90-3.88(m, 4H), 3.86(s, 2H), 3.83-3.81(m. 4H), 3.28(s, 4H), 2.78(s, 3H), 2.71(s, 4H), 2.50(s, 3H).

Synthetic Route of Compound 12 nitrogen. The mixture was diluted with water (50 mL), and extracted with ethyl acetate (50 mL). The organic phase was washed with saturated brine (50 mL), dried over anhydrous sodium sulfate, filtered, and concentrated. The residue was purified by Prep-TLC (methylene chloride: methanol=50:1) to give compound 12-a (90 mg, yield 59%) as a yellow solid. LC-MS (ESI): m/e 393.0(M+H)$^+$.

Synthesis of Compound 12

To a reaction tube containing tetrahydrofuran (4 mL) and water (0.4 mL) were added compound 12-a (90 mg, 0.23 mmol), compound 2-a (112 mg, 0.46 mmol), palladium acetate (10.2 mg, 0.05 mmol), X-phos (11 mg, 0.02 mmol) and cesium carbonate (223 mg, 0.68 mmol). The mixture was sealed and stirred overnight in an oil bath at 80° C. under nitrogen. After cooling, the reaction mixture was filtered through celite, washed with tetrahydrofuran. The filtrate and washings were combined and concentrated. The residue was purified by Prep-TLC (methylene chloride: methanol=20:1) to give compound 12 (20 mg, 20% yield) as a yellow solid. LC-MS (ESI): m/e 490.1(M+H)$^+$. $^1$H NMR (500 MHz, CDCl$_3$): δ 8.95(s, 1H), 8.28-8.26(m, 1H), 7.72(s, 1H), 4.89(s, 2H), 3.94-3.93(m, 4H), 3.86-3.83(m, 6H), 3.28-3.26(m, 4H), 2.78(s, 3H), 2.71-2.69(m, 4H).

Synthetic Route of Compound 13

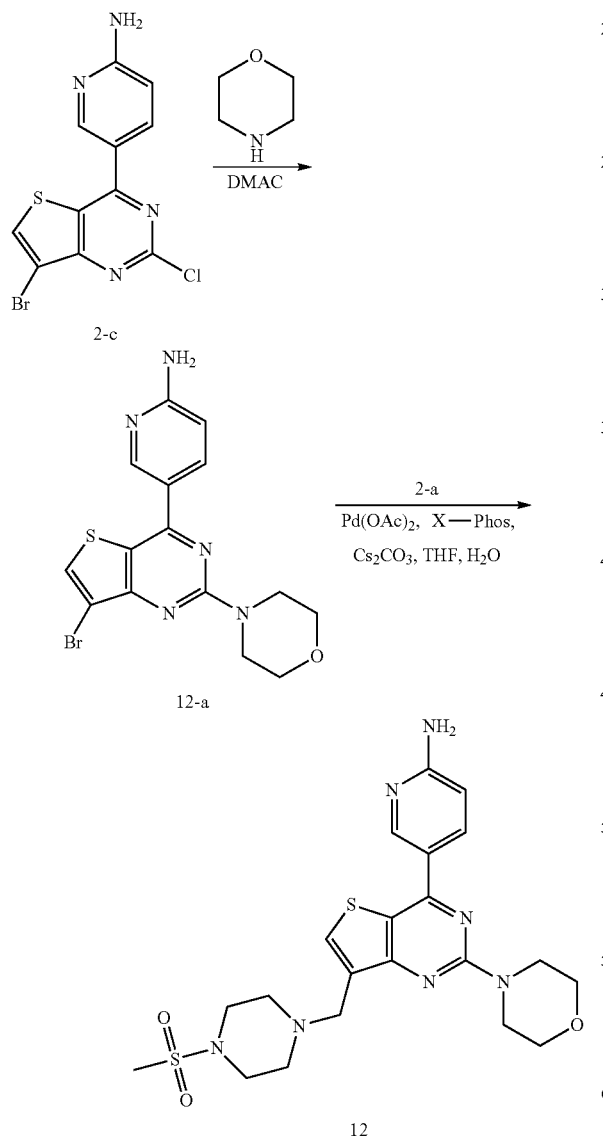

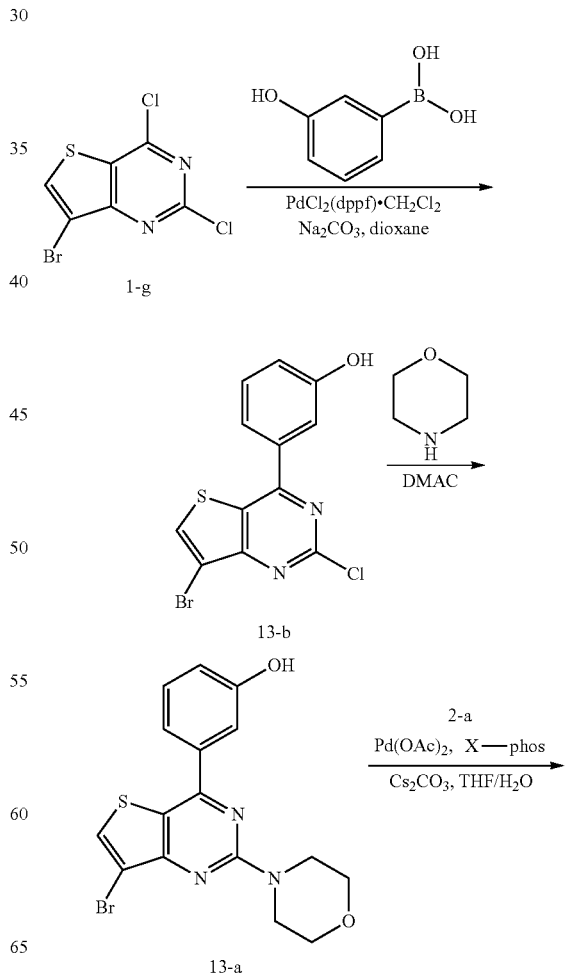

Synthesis of Compound 12-a

Compound 2-c (133 mg, 0.39 mmol) and morpholine (67.8 mg, 0.78 mmol) were dissolved in DMAC (4 mL), and the mixture was heated to 94° C. and stirred overnight under

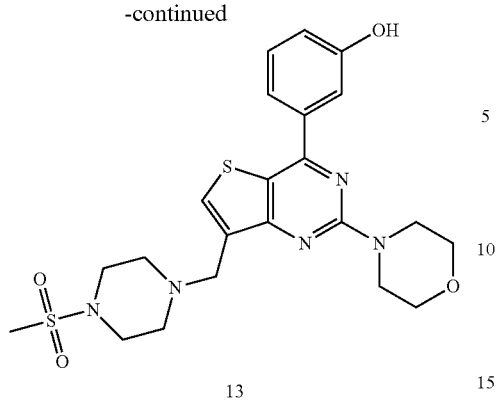

13

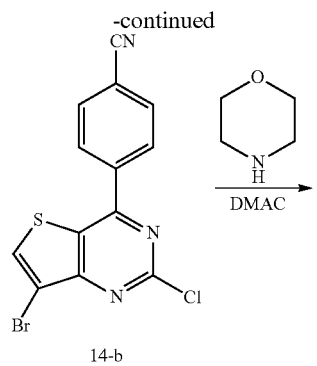

14-b

Synthesis of Compound 13-b

To a flask containing dioxane (10 mL) were added compound 1-g (400 mg, 1.41 mmol), 3-hydroxyphenyl boronic acid (214 mg, 1.55 mmol), PdCl$_2$(dppf)$_2$ (115 mg, 0.14 mmol) and aqueous sodium carbonate (2 M, 2.1 mL). Under nitrogen, the reaction mixture was stirred overnight at 80° C. After cooling, water (100 mL) was added, and the solution was extracted with ethyl acetate (100 mL). The organic phase was dried over anhydrous magnesium sulfate, filtered, and concentrated. The residue was purified by column chromatography (dichloromethane: methanol=30:1) to give compound 13-b (198 mg, yield 41%) as a yellow solid. LC-MS (ESI): m/z 340.9 (M+H)$^+$.

Synthesis of Compound 13-a

A mixture of compound 13-b (198 mg, 0.58 mmol), morpholine (126 mg, 1.45 mmol) and N, N-dimethylacetamide (4 mL) was heated to 95° C. and stirred overnight. The reaction mixture was diluted with water (50 mL), extracted with ethyl acetate (50 mL). The organic phase was washed with saturated brine (50 mL), dried over anhydrous sodium sulfate, filtered, and concentrated. The residue was purified by Prep-TLC (methylene chloride: petroleum ether=2:1) to give compound 13-a (137 mg, yield 60%) as a yellow solid. LC-MS (ESI): m/z 392.0 (M+H)$^+$.

Synthesis of Compound 13

To a reaction tube was added a mixture of compound 13-a (137 mg, 0.35 mmol), compound 2-a (175 mg, 0.70 mmol), palladium acetate (17 mg, 0.07 mmol), X-Phos (17 mg, 0.04 mmol), cesium carbonate (342 mg, 1.05 mmol), tetrahydrofuran (3 mL) and water (0.3 mL) under nitrogen atmosphere, and the mixture was heated to 80° C. with oil bath and stirred overnight. After cooling, the reaction mixture was filtered through celite, washed with tetrahydrofuran. The filtrate and washings were combined and concentrated. The residue was purified by Prep-TLC (methylene chloride: methanol=20:1) to give compound 13 (36 mg, 21% yield). LC-MS (ESI): m/z 490.1 (M+H)$^+$. $^1$H NMR (500 MHz, CDCl$_3$): δ 7.68 (s, 1H), 7.55(d, 1H), 7.31(t, 1H), 7.05(s, 1H), 6.95(d, 1H), 3.85-3.84 (m, 6H), 3.80-3.78(m, 4H), 3.33(s, 4H), 2.78-2.76(m, 6H).

Synthetic Route of Compound 14

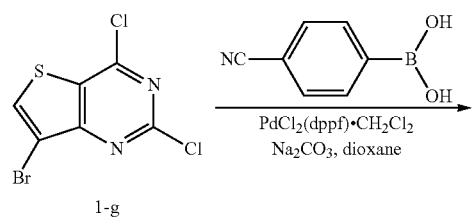

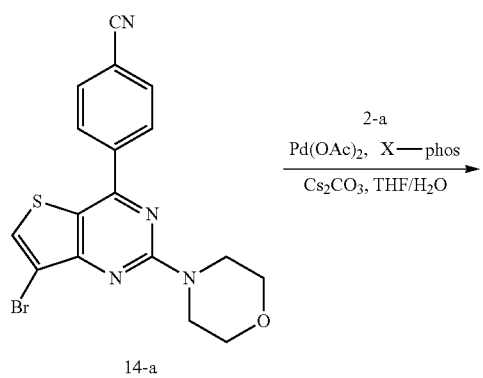

14-a

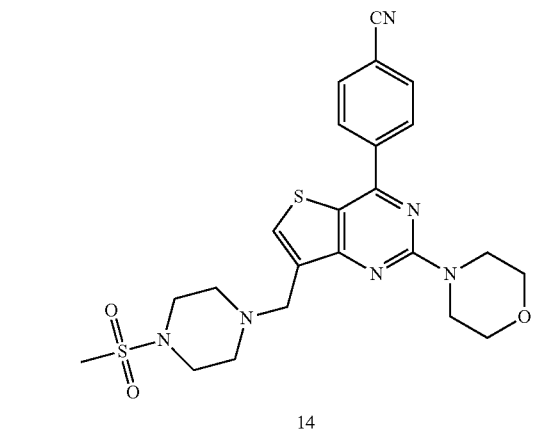

14

Synthesis of Compound 14-b

To a flask containing dioxane (25 mL) were added compound 1-g (338 mg, 1.2 mmol), p-cyano phenyl boronic acid (212 mg, 1.44 mmol), PdCl$_2$(dppf)$_2$ (98 mg, 0.12 mmol) and 2 M sodium carbonate solution (2.5 mL). The mixture was stirred overnight at 80° C. under nitrogen. After cooling, water (50 mL) was added, and the solution was extracted with ethyl acetate (50 mL×3). The organic phase was dried over anhydrous magnesium sulfate, filtered, and concentrated. The residue was purified by column chromatography (petroleum ether/ethyl acetate=3:1 to 1:1) to give compound 14-b (370 mg, 88% yield) as a yellow solid. LC-MS (ESI): m/e 349.9 (M+H)$^+$.

Synthesis of Compound 14-a

Compound 14-b (370 mg, 1.06 mmol), morpholine (205 µL, 2.34 mmol), and triethylamine (0.18 mL, 1.32 mmol) were dissolved in DMAC (7 mL). The mixture was heated to 94° C. and stirred for 24 hours under nitrogen. After cooling, water (14 mL) was added, and the mixture was extracted with ethyl acetate (20 mL×3). The organic phase was dried over anhydrous magnesium sulfate, filtered, and concentrated. The residue was purified by column chromatography (petroleum ether/tetrahydrofuran=4:1 to 2:1) to give compound 14-a (243 mg, 57% yield) as a yellow solid. LC-MS (ESI): m/e 401.0(M+H)+.

Synthesis of Compound 14

To a microwave tube containing THF (1.0 mL) and water (0.1 mL) were added compound 14-a (243 mg, 0.60 mmol), compound 2-a (295 mg, 1.2 mmol), palladium acetate (3 mg, 0.012 mmol), X-phos (6 mg, 0.012 mmol) and cesium carbonate (117 mg, 0.36 mmol). Under nitrogen, the reaction mixture was stirred for 24 hours at 80° C. Reaction was not complete, the reaction mixture was placed in microwave for 1 hour at 125° C., 150 W. After cooling, the reaction mixture was filtered through celite, washed with tetrahydrofuran. The filtrate and washings were combined and concentrated. The residue was purified by Prep-HPLC to give compound 14 (50 mg, yield 17%) as a yellow solid. LC-MS (ESI): m/e 499.2 (M+H)+. 1H NMR (500 MHz, CDCl3): δ 8.25 (d, 2H, J=8.0 Hz), 7.84 (d, 2H, J=8.0 Hz), 7.79 (s, 1H), 3.95 (t, 4H, J=4.5 Hz), 3.88 (s, 2H), 3.85 (t, 4H, J=4.5 Hz), 3.28 (t, 4H, J=4.5 Hz), 2.78 (s, 3H), 2.71 (t, 4H, J=4.5 Hz).

Synthetic Route of Compound 15

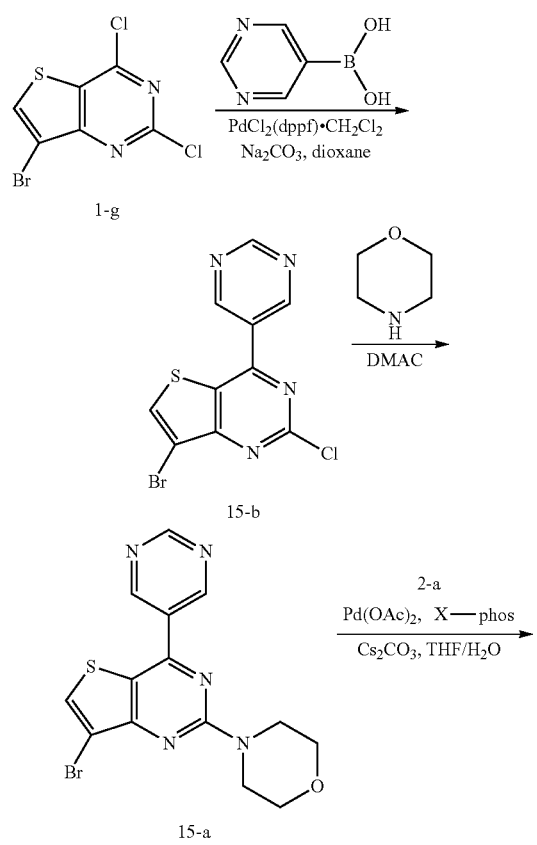

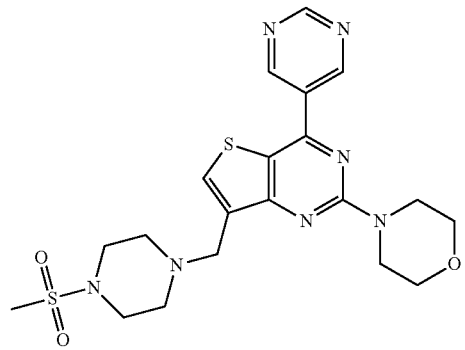

15

Synthesis of Compound 15-b

To a flask containing 1,4-dioxane (25 mL) were added compound 1-g (338 mg, 1.2 mmol), pyrimidine 5-boronic acid (178 mg, 1.44 mmol), PdCl2(dppf)2 (98 mg, 0.12 mmol) and 2 M sodium carbonate solution (2.5 mL). Under nitrogen, the mixture was stirred at 80° C. for overnight. After cooling, water (50 mL) was added, and the solution was extracted with ethyl acetate (50 mL×3). The organic phase was dried over anhydrous magnesium sulfate, filtered, and concentrated. The residue was purified by column chromatography (petroleum ether/ethyl acetate=3:1 to 1:1) to give compound 15-b (152 mg, yield 39%) as a yellow solid. LC-MS (ESI): m/e 326.9 (M+H)+.

Synthesis of Compound 15-a

Compound 15-b (152 mg, 0.47 mmol), morpholine (91 µL, 1.03 mmol) and triethylamine (0.18 mL, 1.32 mmol) were dissolved in DMAC (7 mL). Under nitrogen, the mixture was heated to 94° C. and stirred for 24 hours. After cooling, water (14 mL) was added, and the solution was extracted with ethyl acetate (20 mL x 3). The organic phase was dried over anhydrous magnesium sulfate, filtered, and concentrated. The residue was purified by column chromatography (petroleum ether/tetrahydrofuran=4:1 to 2:1) to give compound 15-a (93 mg, 53% yield) as a yellow solid. LC-MS (ESI): m/e 378.0 (M+H)+.

Synthesis of Compound 15

To a microwave tube containing THF (1.0 mL) and water (0.1 mL) were added compound 15-a (93 mg, 0.25 mmol), compound 2-a (123 mg, 0.5 mmol), palladium acetate (3 mg, 0.012 mmol), X-phos (6 mg, 0.012 mmol) and cesium carbonate (117 mg, 0.36 mmol). Under nitrogen, the reaction mixture was stirred for 24 hours at 80° C. Reaction was not complete, the reaction mixture was placed in microwave for 1 hour at 125° C., 150W. After cooling, the reaction mixture was filtered through celite, washed with tetrahydrofuran. The filtrate and washings were combined and concentrated. The residue was purified by Prep-HPLC to give compound 15 (27 mg, yield 23%) as a yellow solid. LC-MS (ESI): m/e 476.1 (M+H)+. 1H NMR (500 MHz, CDCl3): δ 9.48 (s, 2H), 9.36 (s, 1H), 7.82 (s, 1H), 3.96 (t, 4H, J=4.5 Hz), 3.88 (s, 2H), 3.85 (t, 4H, J=4.5 Hz), 3.28 (t, 4H, J=4.5 Hz), 2.79 (s, 3H), 2.71 (t, 4H, J=4.5 Hz).

Synthetic Route of Compound 16

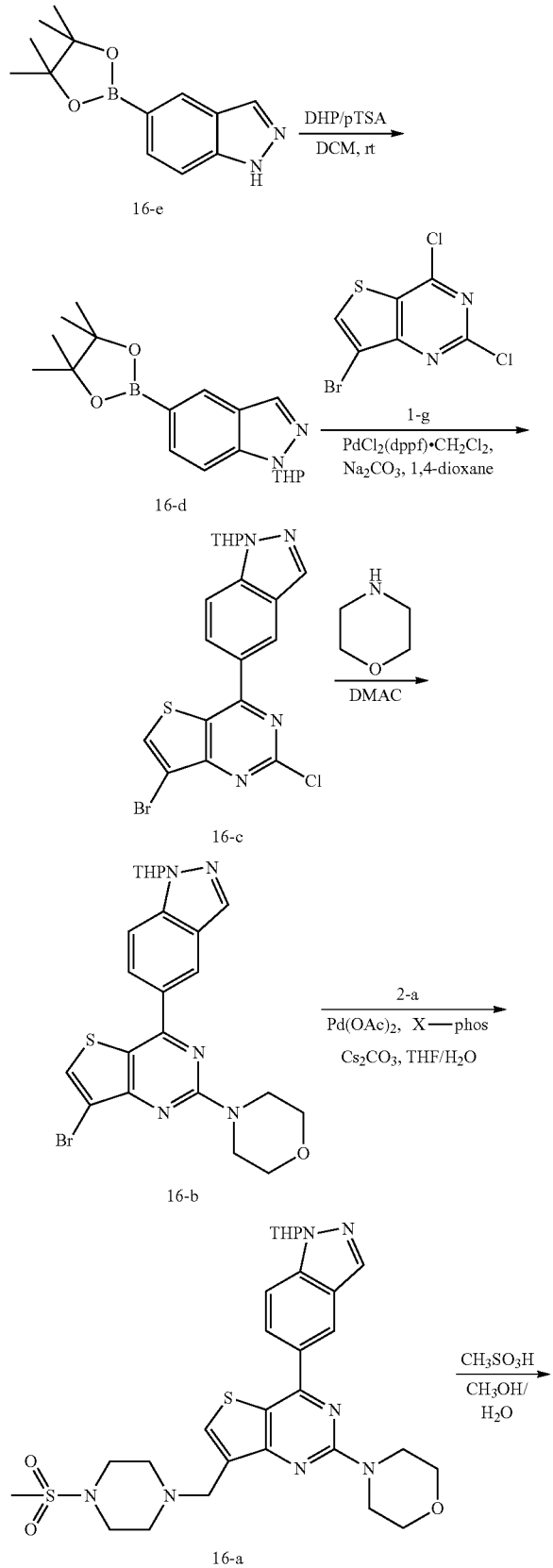

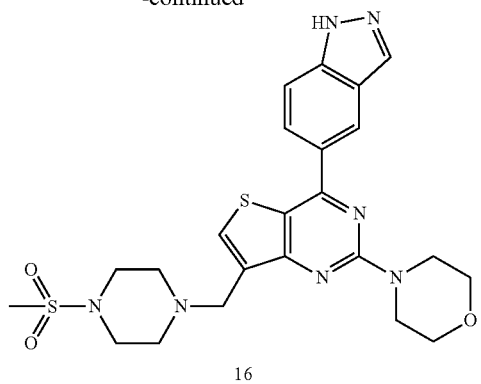

Synthesis of Compound 16-d

To a solution of compound 16-e (400 mg, 1.628 mmol) in dichloromethane (5 mL) were added dihydropyran (DHP) (413 mg, 4.92 mmol) and p-toluenesulfonic acid (pTSA) (31 mg, 0.164 mmol). The mixture was stirred overnight at room temperature. In the next day, the reaction mixture was diluted with dichloromethane (10 mL), the organic layer was washed with saturated NaHCO$_3$ solution, dried over anhydrous Na$_2$SO$_4$, filtered, and concentrated. The residue was purified by column chromatography (petroleum ether: ethyl acetate=9:1) to give compound 16-d (404 mg, yield 76%) as a colorless oil. LC-MS (ESI): m/e 329.2 (M+H)$^+$.

Synthesis of Compound 16-c

To a flask containing dioxane (18 mL) were added compound 1-g (256 mg, 0.902 mmol), compound 16-d (404 mg, 0.902 mmol), PdCl$_2$(dppf)·CH$_2$Cl$_2$ (74 mg, 0.092 mmol) and 2 N sodium carbonate solution (1.5 mL). Under nitrogen, the reaction mixture was stirred overnight at 80° C. Water (100 mL) was added, and the solution was extracted with ethyl acetate (60 mL). The organic phase was dried over anhydrous sodium sulfate, filtered, and concentrated. The residue was purified by Prep-TLC (methylene chloride: petroleum ether=2:1) to give compound 16-c (170 mg, yield 42%) as a yellow solid. LC-MS (ESI): m/e 449.0 (M+H)$^+$.

Synthesis of Compound 16-b

Compound 16-c (150 mg, 0.335 mmol) and morpholine (73 mg, 0.837 mmol) were dissolved in DMAC (4 mL). Under nitrogen, the mixture was heated to 94° C. and stirred overnight. The mixture was diluted with water (50 mL), and the solution was extracted with ethyl acetate (50 mL). The organic phase was washed with saturated brine, dried over anhydrous sodium sulfate, filtered, and concentrated. The residue was purified by Prep-TLC (ethyl acetate: petroleum ether=1:4) to give compound 16-b (150 mg, yield 90%) as a yellow solid. LC-MS (ESI): m/e 500.1 (M+H)$^+$.

Synthesis of Compound 16-a

To a reaction tube containing THF (3 mL) and water (0.3 mL) were added compound 16-b (150 mg, 0.300 mmol), compound 2-a (148 mg, 0.600 mmol), palladium acetate (14.6 mg, 0.06 mmol), X-phos (14.5 mg, 0.03 mmol) and cesium carbonate (0.293 g, 0.900 mmol). Under nitrogen, the mixture was stirred overnight in an 80° C. oil bath. After cooling, the reaction mixture was filtered through celite, washed with tetrahydrofuran. The filtrate and washings were combined and concentrated. The residue was purified by Prep-TLC (methylene chloride: methanol=50:1) to give compound 16-a (55 mg, 31% yield) as a yellow solid. LC-MS (ESI): m/e 598.3 (M+H)$^+$.

Synthesis of Compound 16

To a round bottom flask containing methanol (3 mL) and water (1 mL) were added compound 16-a (55 mg, 0.092 mmol), methanesulfonic acid (44 mg, 0.460 mmol) was added under nitrogen. The mixture was stirred at room temperature for 1 hour, and then warmed to 65° C., stirred for another 16 hours. The reaction solution was washed with saturated sodium bicarbonate solution to pH 7~8. Water (20 mL) was added, and the solution was extracted with ethyl acetate (20 mL). The organic phase was dried over anhydrous sodium sulfate, filtered, and concentrated. The residue was purified by Prep-TLC (methylene chloride: methanol=20:1) to give compound 16 (38 mg, 80% yield). LC-MS (ESI): m/e 514.2 (M+H)$^+$. $^1$HNMR (500 MHz, CDCl$_3$): δ 10.83 (s, 1H), 8.59 (s, 1H), 8.24-8.21 (m, 2H), 7.76 (s, 1H), 7.61 (d, 1H), 3.98-3.96 (m, 4H), 3.49 (s, 2H), 3.30-3.28 (m, 4H), 2.78 (s, 3H), 2.74-2.72 (m, 4H).

Synthetic Route of Compound 17

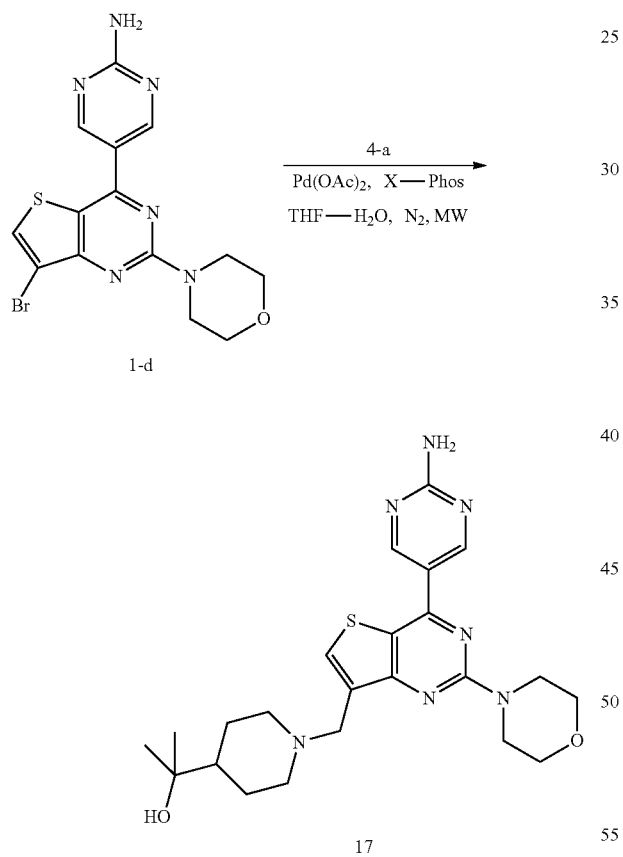

Synthesis of Compound 17

To a microwave tube containing THF (1.0 mL) and water (0.1 mL) were added compound 1-d (157 mg, 0.4 mmol), compound 2-a (180 mg, 0.8 mmol), palladium acetate (3 mg, 0.012 mmol), X-phos (6 mg, 0.012 mmol) and cesium carbonate (117 mg, 0.36 mmol). Under nitrogen, the reaction mixture was stirred for 24 hours at 80° C. Reaction was not complete, the reaction mixture was placed in microwave for 1 hour at 125° C., 150W. After cooling, the reaction mixture was filtered through celite, washed with tetrahydrofuran. The filtrate and washings were combined and concentrated. The residue was purified by Prep-HPLC to give compound 17 (86 mg, yield 50%) as a yellow solid. LC-MS (ESI): m/e 470.0 (M+H)$^+$. $^1$HNMR (500 MHz, CDCl$_3$): δ 9.10 (s, 2H), 7.86 (s, 1H), 5.58 (d, 2H, J=6.0 Hz), 3.92 (t, 4H, J=5.0 Hz), 3.85 (s, 2H), 3.83 (t, 4H, J=5.0 Hz), 3.13 (d, 2H, J=11.0 Hz), 2.14 (t, 2H, J=11.5 Hz), 1.76-1.73 (m, 4H), 1.49 (d, 1H, J=3.0 Hz), 1.46 (d, 1H, J=2.5 Hz), 1.16 (s, 6H).

Synthetic Route of Compound 18

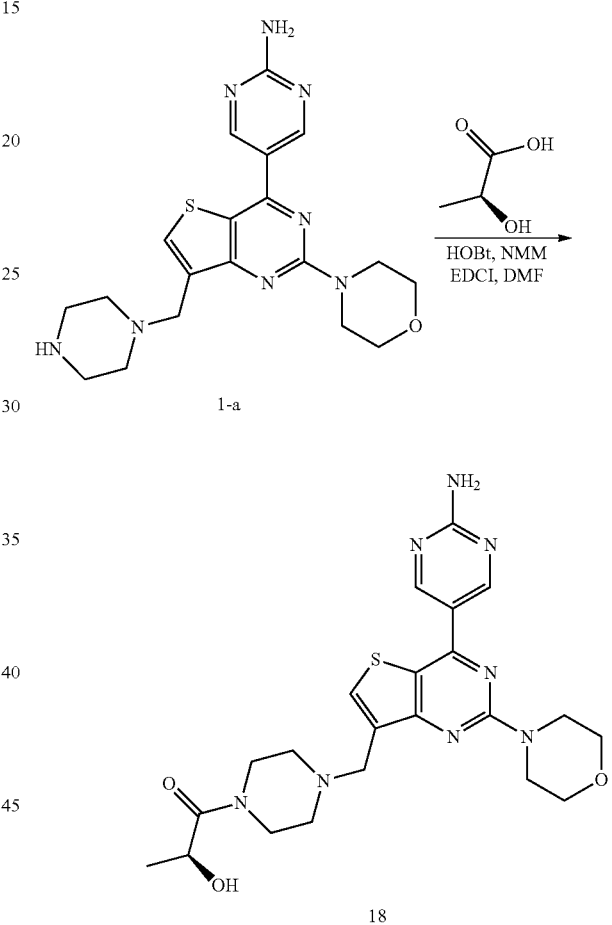

Synthesis of Compound 18

Compound 1-a (60 mg, 0.146 mmol) and L-lactic acid (13.2 mg, 0.146 mmol) were dissolved in DMF (2 mL), and then were added HOBt (25 mg, 0.186 mmol), NMM (0.372 mmol) and EDCI (36 mg, 0.186 mmol) one by one. The reaction mixture was stirred at 25° C. for 24 hours. Water (5 mL) was added to quench the reaction. The mixture was extracted with dichloromethane (10 mL×3). The organic phase was washed with saturated brine (30 mL×2), dried over anhydrous sodium sulfate, filtered, and concentrated. The residue was purified by Prep-TLC (DCM/MeOH=20/1) to give compound 18 (30 mg, yield 42%) as a yellow solid. LC-MS (ESI): m/z 485.2 (M+H)$^+$. $^1$H NMR (500 MHz, CDCl$_3$): δ 9.10 (s, 2H), 7.80 (s, 1H), 4.47 (dd, 1H, J=13.0

Hz, 6.5 Hz), 3.93 (t, 4H, J=4.5 Hz), 3.86 (s, 2H), 3.85 (t, 4H, J=5.5 Hz), 3.78 (t, 1H, J=3.5 Hz), 3.63 (t, 1H, J=3.5 Hz), 3.48 (t, 2H, J=9.0 Hz), 2.60 (s, 4H), 1.32 (d, 3H, J=6.5 Hz).

Synthetic Route of Compound 19

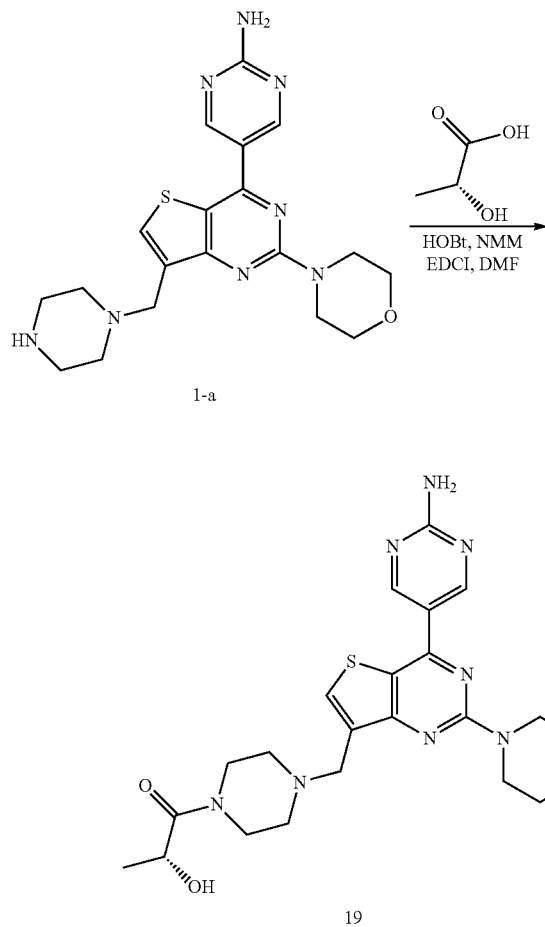

Synthesis of Compound 19

Compound 1-a (70 mg, 0.17 mmol) and D-lactic acid (16.2 mg, 0.17 mmol) were dissolved in DMF (2 mL), and then were added HOBt (29 mg, 0.217 mmol), NMM (0.434 mmol) and EDCI (42 mg, 0.217 mmol) one by one. The reaction mixture was stirred at 25° C. for 24 hours. Water (5 mL) was added to quench the reaction. The mixture was extracted with dichloromethane (10 mL×3). The organic phase was washed with saturated brine (30 mL×2), dried over anhydrous sodium sulfate, filtered, and concentrated. The residue was purified by Prep-TLC (DCM/MeOH=20/1) to give compound 19 (50 mg, yield 61%) as a yellow solid. LC-MS (ESI): m/z 485.2 (M+H)$^+$. $^1$H NMR (500 MHz, CDCl$_3$): δ 9.02 (s, 2H), 7.72 (s, 1H), 4.39 (dd, 1H, J=13.5 Hz, 7.0 Hz), 3.85 (t, 4H, J=4.5 Hz), 3.79 (s, 2H), 3.77 (t, 4H, J=4.5 Hz), 3.71 (t, 1H, J=5.0 Hz), 3.54 (t, 1H, J=5.5 Hz), 3.40 (m, 2H), 2.52 (s, 4H), 1.24 (d, 3H, J=6.5 Hz).

Synthetic Route of Compound 20

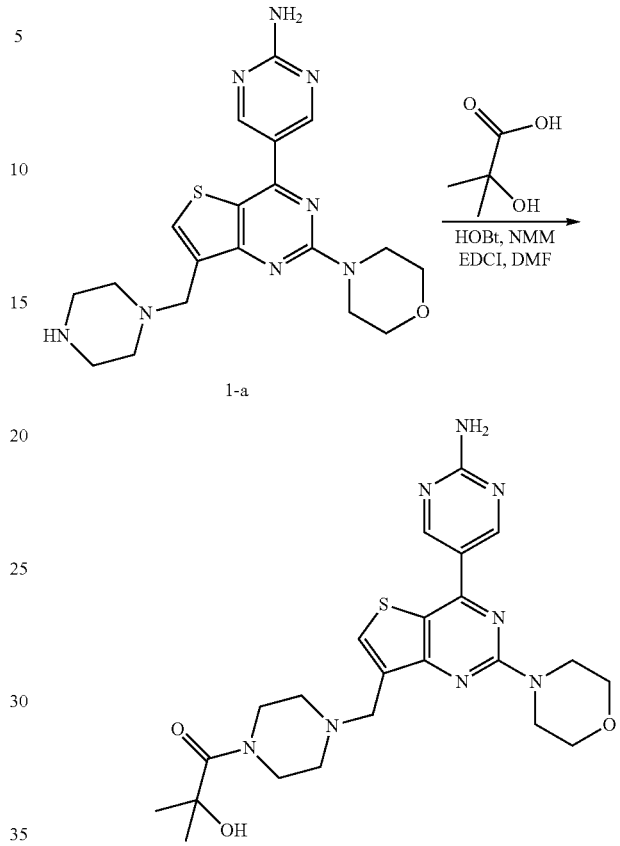

Synthesis of Compound 20

According to the synthesis procedure of compound 19, using compound 1-a (65 mg, 0.157 mmol) and 2-methyl lactate (18 mg, 0.173 mmol) as starting material to give compound 20 (40 mg, 51% yield) as a yellow solid. LC-MS (ESI): m/z 499.2 (M+H)$^+$. $^1$H NMR (500 MHz, CDCl$_3$): δ 9.00 (s, 2H), 8.13 (s, 1H), 7.38 (s, 2H), 3.82 (t, 4H, J=4.5 Hz), 3.80 (s, 2H), 3.72 (t, 4H, J=4.5 Hz), 3.32 (s, 4H), 2.45 (s, 4H), 1.27 (s, 6H).

Synthetic Route of Compound 21

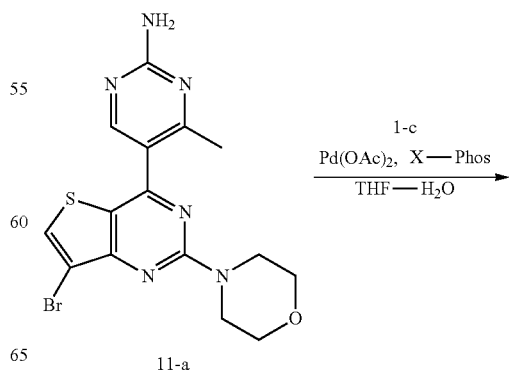

-continued

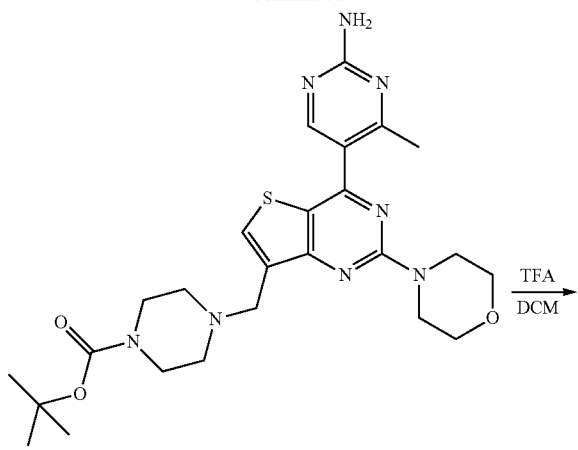
21-b

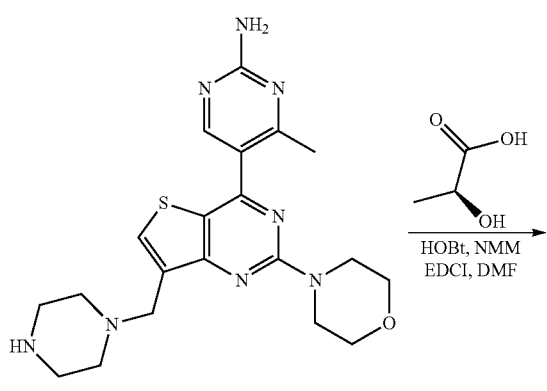
21-a

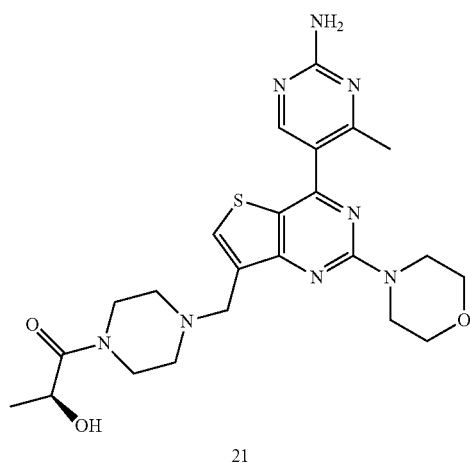
21

Synthesis of Compound 21-b

To a reaction tube were added compound 11-a (366 mg, 0.9 mmol), compound 1-c (485 mg, 1.8 mmol), Pd(OAc)$_2$ (40 mg, 0.18 mmol), x-Phos (43 mg, 0.09 mmol), Cs$_2$CO$_3$ (879 mg, 2.7 mmol), THF (3.6 mL), H$_2$O (0.4 mL). Under nitrogen, the mixture was stirred overnight at 80° C. After cooling, the reaction mixture was filtered through a plug of 100-200 mesh silica gel. The filter cake was washed with THF, and the combined filtrates were concentrated. The residue was purified by column chromatography to give compound 21-b (382 mg, 81%). LC-MS (ESI): m/z 527.3 (M+H)$^+$.

Synthesis of Compound 21-a

Compound 21-b (382 mg, 0.73 mmol) was dissolved in DCM (3 mL), and then CF$_3$COOH/DCM (2.6 M, 3 mL) was slowly added, and the reaction mixture was stirred at room temperature for 1 hour. The reaction mixture was concentrated and saturated sodium carbonate solution (5 mL) was added. After stirring for 5 minutes at room temperature, the mixture was extracted with DCM (10 mL×6). The organic phase was washed with saturated brine (20 mL×2), dried over anhydrous sodium sulfate, filtered and concentrated to afford compound 21-a (180 mg, yield 58%) as a yellow solid. LC-MS (ESI): m/z 427.2(M+H)$^+$.

Synthesis of Compound 21

Compound 21-a (90 mg, 0.21 mmol) and L-lactic acid (21 mg, 0.22 mmol) were dissolved in DMF (2 mL), and then were added HOBt (43 mg, 0.32 mmol), NMM (64 mg, 0.63 mmol) and EDCI (61 mg, 0.32 mmol) one by one. The reaction mixture was stirred at 25° C. for 24 hours. In the next day, water (30 mL) was added to quench the reaction. The mixture was extracted with dichloromethane (30 mL×3). The organic phase was washed with saturated brine (10 mL×2), dried over anhydrous sodium sulfate, filtered, and concentrated. The residue was purified by Prep-TLC (DCM/MeOH=20/1) to give compound 21 (25 mg, yield 24%) as a white solid. LC-MS (ESI): m/z 499.2 (M+H)$^+$. $^1$H NMR (500 MHz, CDCl$_3$ (two drops of deuterated methanol were added)): δ 8.43 (1H, s), 7.74 (1H, s), 4.39 (1H, q), 3.64-3.90 (12H, m), 3.48-3.61 (1H, m), 3.34-3.48 (2H, m), 2.46-2.65 (4H, m), 2.43 (3H, s), 1.26 (3H, d).

Synthetic Route of Compound 22

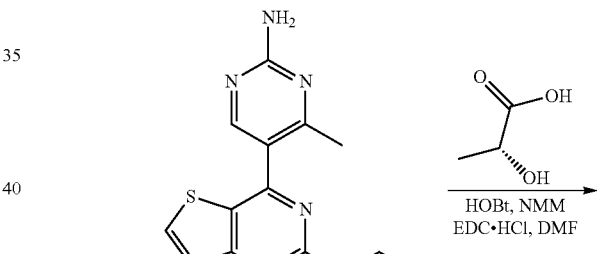
21-a

22

Synthesis of Compound 22

Compound 21-a (90 mg, 0.21 mmol) and D-lactic acid (21 mg, 0.22 mmol) were dissolved in DMF (2 mL), and then were added HOBt (43 mg, 0.32 mmol), NMM (64 mg, 0.63 mmol) and EDCI (61 mg, 0.32 mmol) one by one. The reaction mixture was stirred at 25° C. for 24 hours. In the next day, water (30 mL) was added to quench the reaction. The mixture was extracted with dichloromethane (30 mL×3). The organic phase was washed with saturated brine (10 mL×2), dried over anhydrous sodium sulfate, filtered, and concentrated. The residue was purified by Prep-TLC (DCM/MeOH=20/1) to give compound 22 (29 mg, yield 28%) as a white solid. LC-MS (ESI): m/z 499.2 (M+H)$^+$. $^1$H NMR (500 MHz, CDCl$_3$ (two drops of deuterated methanol were added)): δ 8.44 (1H, s), 7.74 (1H, s), 4.39 (1H, q), 3.66-2.96 (12H, m), 3.48-3.61 (1H, m), 3.33-3.48 (2H, m), 2.47-2.66 (4H, m), 2.44 (3H, s), 1.26 (3H, d).

Synthetic Route of Compound 23

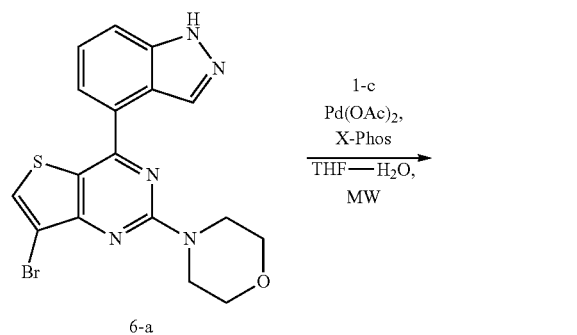

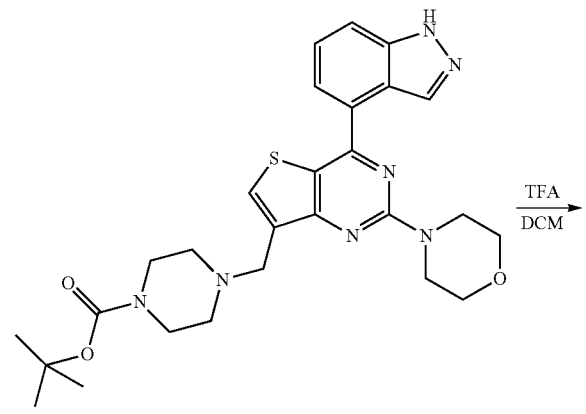

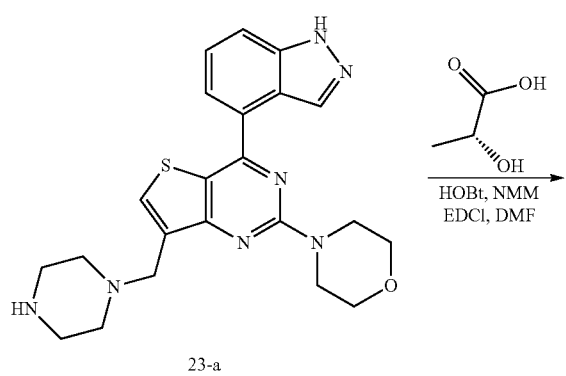

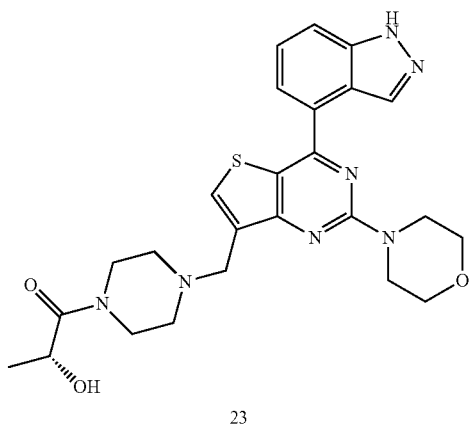

Synthesis of Compound 23-b

According to the synthesis procedure of compound 21-b, using compound 6-a (374 mg, 0.9 mmol) and compound 1-c (485 mg, 1.8 mmol) as starting material to give compound 23-b (169 mg, yield 35%) as a yellow solid. LC-MS (ESI): m/z 536.2 (M+H)$^+$.

Synthesis of Compound 23-a

According to the synthesis procedure of compound 21-a, using compound 23-b (160 mg, 0.3 mmol) as starting material to give compound 23-a (102 mg, yield 78%) as a yellow solid. LC-MS (ESI): m/z 436.2 (M+H)$^+$.

Synthesis of Compound 23

According to the synthesis procedure of compound 22, using compound 23-a (37.4 mg, 0.086 mmol) and D-lactic acid (16 mg, 0.17 mmol) as starting material to give compound 23 (15 mg, 34% yield) as a yellow solid. LC-MS (ESI): m/z 508.3 (M+H)$^+$. $^1$H NMR (500 MHz, CDCl$_3$): δ 8.59 (1H, s), 7.91 (1H, d), 7.79 (1H, s), 7.66 (1H, d), 7.48-7.59 (1H, m), 4.45 (1H, q), 3.92-4.02 (4H, m), 3.89 (2H, s), 3.81-3.87 (4H, m), 3.38-3.50 (2H, m), 2.52-2.73 (4H, m), 1.32 (3H, d), 3.75-3.82 (1H, m), 3.56-3.71 (1H, m).

Synthetic Route of Compound 24

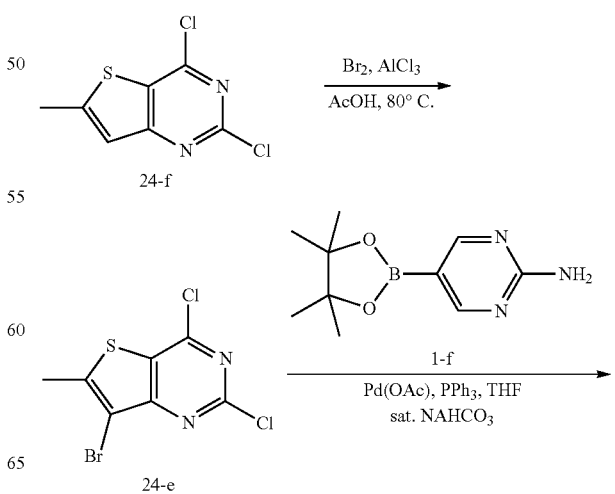

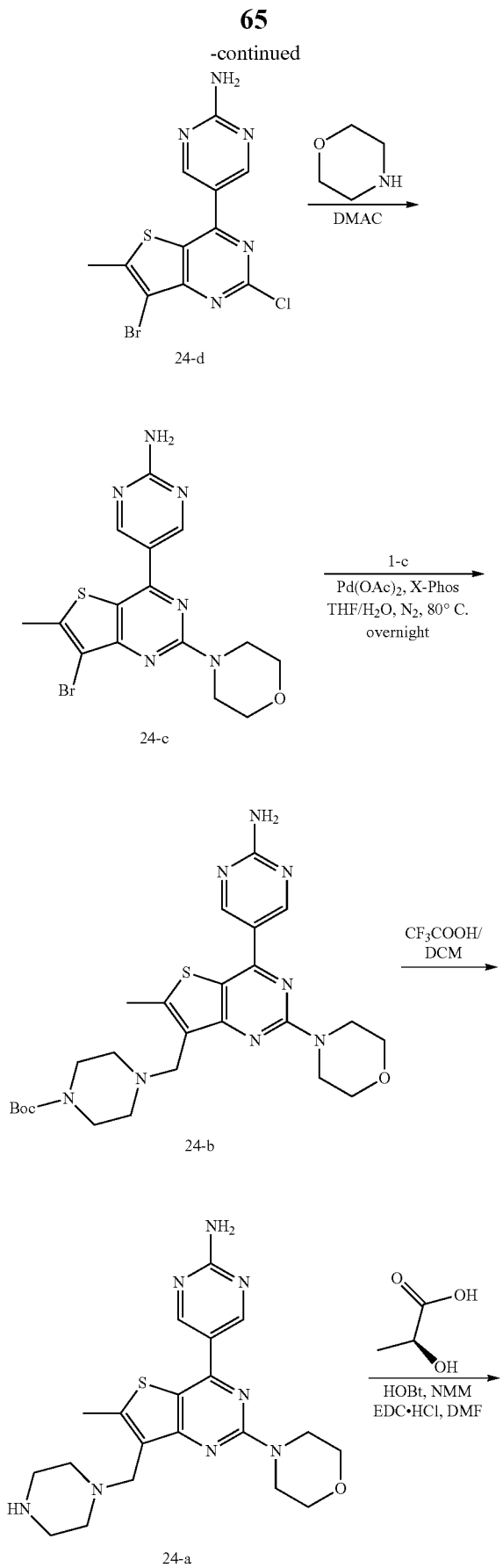
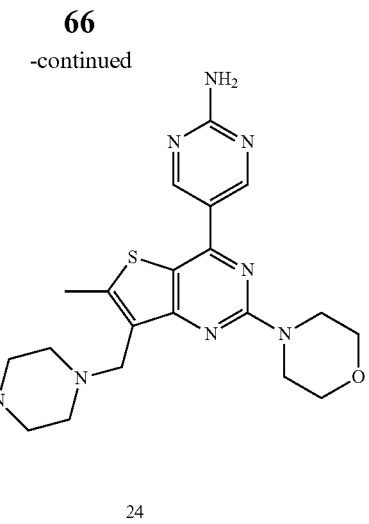

Synthesis of Compound 24-e

To an acetic acid (15 mL) solution of 24-f (according to the synthesis procedure in the patent: WO 2007/023382 A2) (992 mg, 4.6 mmol) and aluminum trichloride (1.23 g, 9.2 mmol) was slowly added a solution of bromine (0.72 mL, 13.8 mmol) in acetic acid (5 mL) at room temperature. After dropwise addition, the reaction mixture was heated to 80° C. and stirred for 6 hours. After cooling, the reaction mixture was poured into ethyl acetate (40 mL), washed with water (40 mL), then 5% sodium thiosulfate solution (40 mL×2) to remove the color of bromine. The aqueous phase was extracted with ethyl acetate (120 mL×2). The organic layers were combined and washed with saturated sodium bicarbonate solution (100 mL) and saturated brine (200 mL), dried over anhydrous sodium sulfate, filtered, and concentrated to give title compound 24-e (1.035 g, yield 76%) as a pale yellow solid. LC-MS (ESI): m/z 296.9 (M+H)$^+$.

Synthesis of Compound 24-d

Compound 24-e (287 mg, 0.97 mmol), Pd (OAc) 2 (23 mg, 0.1 mmol) and triphenylphosphine (51 mg, 0.194 mmol) were dissolved in tetrahydrofuran (14 mL). After stirring at room temperature for 5 minutes, compound 1-f (237 mg, 1.07 mmol) and a saturated solution of sodium bicarbonate (1.4 mL). Under nitrogen, the reaction mixture was stirred overnight at 90° C., cooled, filtered, washed with tetrahydrofuran, and the washings and filtrate were concentrated. The residue was purified by column chromatography (petroleum ether/tetrahydrofuran=1/1) to give title compound 24-d (137 mg, yield 45%) as a pale yellow solid. LC-MS (ESI): m/z 355.9 (M+H)$^+$.

Synthesis of Compound 24-c

Compound 24-d (137 mg, 0.39 mmol) and morpholine (0.86 mmol) were dissolved in DMAC (6 mL), under nitrogen, the mixture was heated to 94° C. and stirred overnight. After cooling, water (12 mL) was added, the precipitated solid was filtered, washed with water, rinsed with ether, and dried to give title compound 24-c (152 mg, yield 90%) as a yellow solid. LC-MS (ESI): m/z 407.1 (M+H)$^+$.

Synthesis of Compound 24-b

To a reaction tube containing THF (2.0 mL) and water (0.2 mL) were added compound 24-c (152 mg, 0.37 mmol), compound 1-c (150 mg, 0.56 mmol), palladium acetate (9 mg, 0.037 mmol), X-phos (18 mg, 0.037 mmol) and cesium carbonate (362 mg, 1.11 mmol). Under nitrogen, the reaction mixture was stirred overnight at 80° C. After cooling, the mixture was filtered and rinsed with THF. The filtrate and washings were concentrated. The residue was purified by Prep-TLC (DCM/MeOH=20/1) to give title compound 24-b (148 mg, yield 75%) as a yellow solid. LC-MS (ESI): m/z 527.2 (M+H)⁺.

Synthesis of Compound 24-a

Compound 24-b (148 mg, 0.28 mmol) was dissolved in DCM (10 mL), and then CF₃COOH/DCM (2.6 M, 10 mL) was slowly added, and the reaction mixture was stirred at room temperature for 1 hour. The reaction mixture was concentrated and saturated sodium carbonate solution (10 mL) was added. After stirring for 5 minutes at room temperature, the mixture was extracted with DCM (10 mL×3). The organic phase was washed with saturated brine (30 mL×2), dried over anhydrous sodium sulfate, filtered and concentrated to afford title compound 24-a (113 mg, yield 94%) as a pale yellow solid. LC-MS (ESI): m/z 427.2 (M+H)⁺.

Synthesis of Compound 24

Compound 24-a (57 mg, 0.134 mmol) and L-lactic acid (13 mg, 0.147 mmol) were dissolved in DMF (3 mL), and then were added HOBt (27 mg, 0.201 mmol), NMM (0.402 mmol) and EDCI (39 mg, 0.201 mmol) one by one. The reaction mixture was stirred at room temperature for overnight, quenched with water (6 mL). The mixture was extracted with dichloromethane (10 mL×3). The organic layers were combined and washed with saturated brine (30 mL×2), dried over anhydrous sodium sulfate, filtered, and concentrated. The residue was purified by Prep-TLC (DCM/MeOH=10/1) to give title compound 24 (20 mg, yield 31%) as a pale yellow solid. LC-MS (ESI): m/z 499.2 (M+H)⁺. ¹H NMR (400 MHz, CDCl₃): δ 9.01 (s, 2H), 5.54 (s, 2H), 4.37 (t, 1H, J=5.6 Hz), 3.88 (d, 1H, J=6.0 Hz), 3.35 (t, 4H, J=4.0 Hz), 3.77 (t, 4H, J=4.0 Hz), 3.69 (s, 2H), 3.66 (d, 1H, J=4.0 Hz), 3.50 (t, 1H, J=6.4 Hz), 3.31 (t, 2H, J=5.6 Hz), 2.57 (s, 3H), 2.45 (t, 4H, J=4.0 Hz), 1.24 (d, 3H, J=6.4 Hz).

Synthetic Route of Compound 25

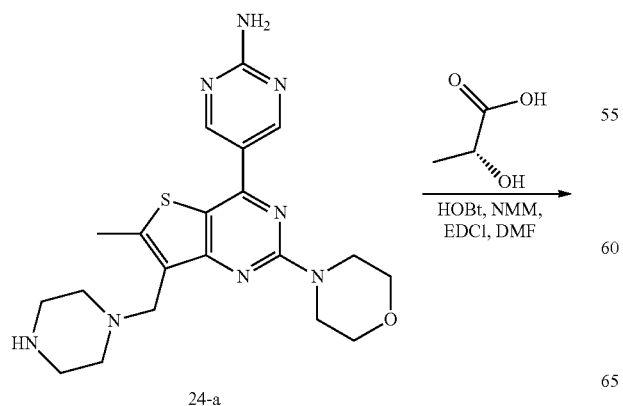

24-a

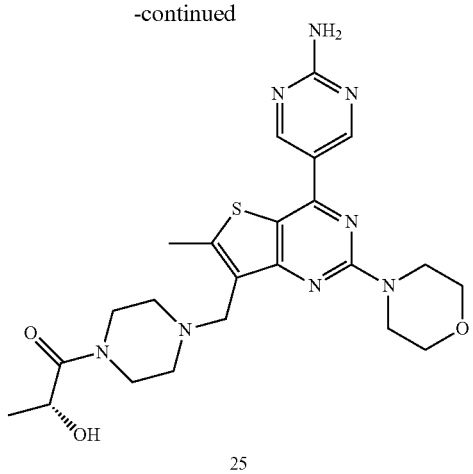

25

Synthesis of Compound 25

According to the synthesis procedure of compound 24, using compound 24-a (56 mg, 0.134 mmol) and D-lactic acid (13 mg, 0.147 mmol) as starting material to give title compound 25 (23 mg, yield 35%) as a pale yellow solid. LC-MS (ESI): m/z 499.3 (M+H)⁺. ¹H NMR (400 MHz, CDCl₃): δ 9.01 (s, 2H), 5.51 (s, 2H), 4.38 (t, 1H, J=6.8 Hz), 3.87 (d, 1H, J=6.8 Hz), 3.83 (t, 4H, J=5.2 Hz), 3.77 (t, 4H, J=5.2 Hz), 3.69 (s, 2H), 3.66 (d, 1H, J=4.0 Hz), 3.50 (t, 1H, J=4.0 Hz), 3.31 (t, 2H, J=4.0 Hz), 2.57 (s, 3H), 2.45 (t, 4H, J=4.0 Hz), 1.24 (d, 3H, J=6.4 Hz).

Synthetic Route of Compound 26

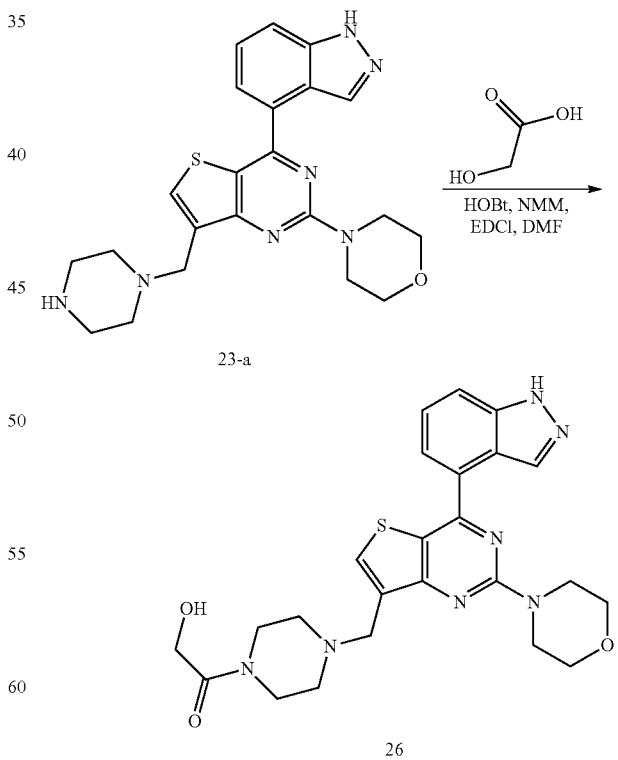

Synthesis of Compound 26

Compound 23-a (0.185 mmol) and glycolic acid (22 mg, 0.278 mmol) were dissolved in DMF (2.5 mL), and then were added HOBt (38 mg, 0.278 mmol), NMM (1.85 mmol) and EDCI (54 mg, 0.278 mmol) one by one. The reaction mixture was stirred at 25° C. for overnight. In the next day, the reaction mixture was quenched with water (4 mL). The mixture was extracted with dichloromethane (10 mL×3). The organic layers were combined and washed with water (10 mL×2), dried over anhydrous sodium sulfate, filtered, and concentrated. The residue was purified by Prep-TLC (DCM/MeOH=15/1) to give title compound 26 (30 mg, yield 33%) as a yellow solid. LC-MS (ESI): m/z 494.2 (M+H)+. 1H NMR (500 MHz, CDCl3): δ 8.58 (1H, s), 7.90 (1H, d), 7.78 (1H, s), 7.64 (1H, d), 7.48-7.58 (1H, m), 4.16 (2H, s), 3.91-4.05 (4H, m), 3.89 (2H, s), 3.79-3.87 (4H, m), 3.72 (2H, t), 3.48 (1H, s), 3.32 (2H, t), 2.53-2.69 (4H, m).

Synthetic Route of Compound 27

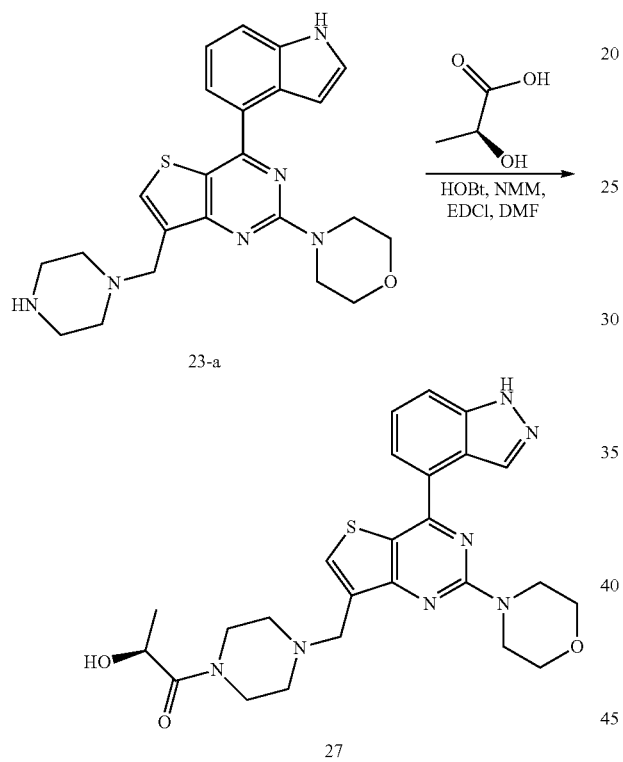

Synthesis of Compound 27

Compound 23-a (0.185 mmol) and L-lactic acid (16 mg, 0.172 mmol) were dissolved in DMF (1.5 mL), and then were added HOBt (18 mg, 0.129 mmol), NMM (0.1 mL, 0.90 mmol) and EDCI (25 mg, 0.129 mmol) one by one. The reaction mixture was stirred at 25° C. for overnight. In the next day, the reaction mixture was quenched with water. The mixture was extracted with dichloromethane. The organic phase was washed with water and saturated sodium chloride, dried over anhydrous sodium sulfate, filtered, and concentrated. The residue was purified by Prep-TLC (eluent: first time DCM/MeOH=10/1; second time THF) to give title compound 27 (20 mg, yield 46%) as a yellow solid. LC-MS (ESI): m/z 508.2 (M+H)+. 1H NMR (500 MHz, CDCl3): δ 8.59 (1H, s), 7.91 (1H, d), 7.78 (1H, s), 7.65 (1H, m), 7.48-7.59 (1H, m), 4.46 (1H, q), 3.92-4.50 (4H, m), 3.89 (2H, s), 3.80-3.87 (4H, m), 3.73-3.80 (1H, m), 3.57-3.69 (1H, m), 3.36-3.53 (4H, m), 2.50-2.75 (4H, m), 1.32 (3H, d).

Synthetic Route of Compound 28

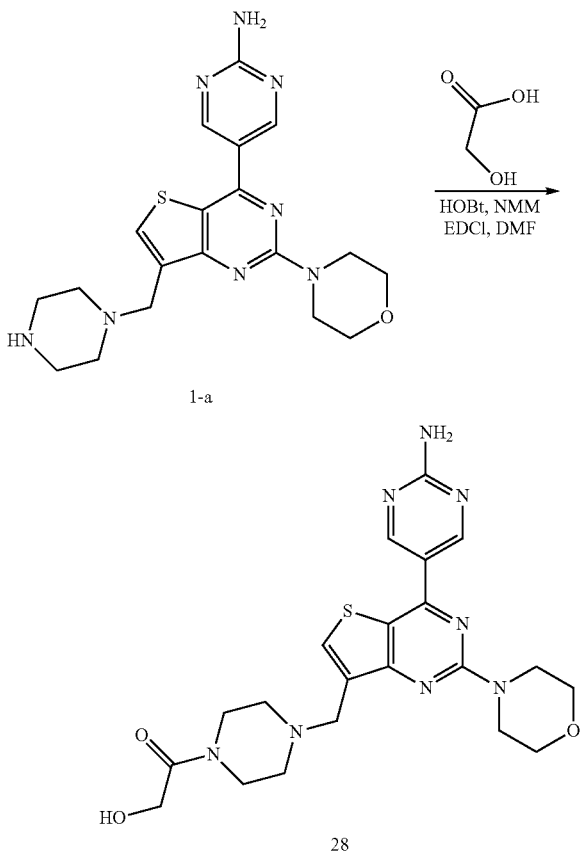

Synthesis of Compound 28

According to the synthesis procedure of compound 26, using compound 1-a (0.18 mmol) as starting material to give title compound 28 (40 mg, 47% yield) as a light yellow solid. LC-MS (ESI): m/z 471.3 (M+H)+. 1H NMR (400 MHz, CDCl3): δ 9.13 (s, 2H), 7.76 (s, 1H), 5.38 (s, 2H), 4.15 (d, 2H, J=4.0 Hz), 3.88-3.97 (m, 4H), 3.79-3.88 (m, 6H), 3.67-3.74 (m, 2H), 3.62 (t, 1H, J=4.4 Hz), 3.30 (t, 2H, J=4.8 Hz), 2.53-2.63 (m, 4H).

Synthetic Route of Compound 29

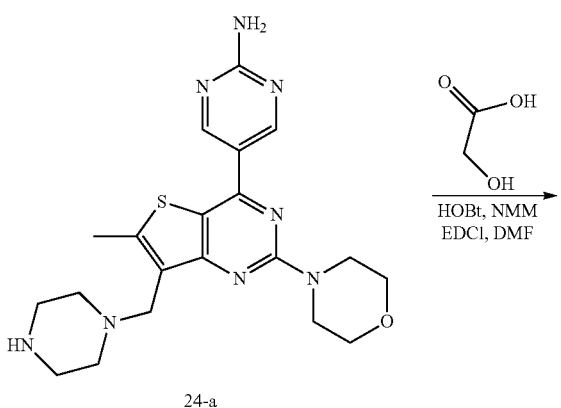

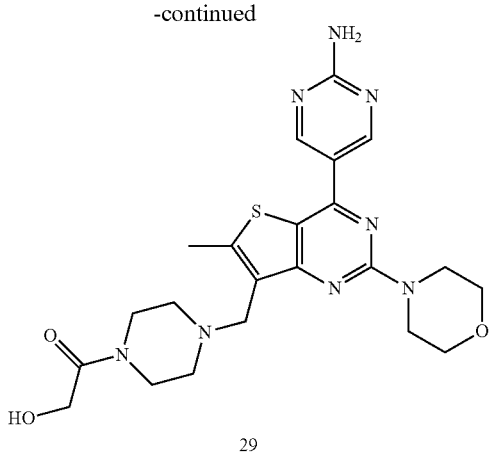

29

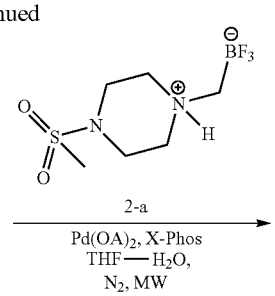

Synthesis of Compound 29

According to the synthesis procedure of compound 26, using compound 24-a (0.164 mmol) as starting material to give title compound 29 (45 mg, 57% yield) as a light yellow solid. LC-MS (ESI): m/z 485.2 (M+H)+. $^1$H NMR (500 MHz, CDCl$_3$): δ 9.06 (s, 2H), 4.14 (s, 2H), 3.90 (s, 4H), 3.84 (s, 4H), 3.79 (s, 2H), 3.64 (s, 2H), 3.27 (d, 2H, J=5.0 Hz), 2.66 (s, 3H), 2.55 (t, 4H, J=5.0 Hz).

Synthetic Route of Compound 30

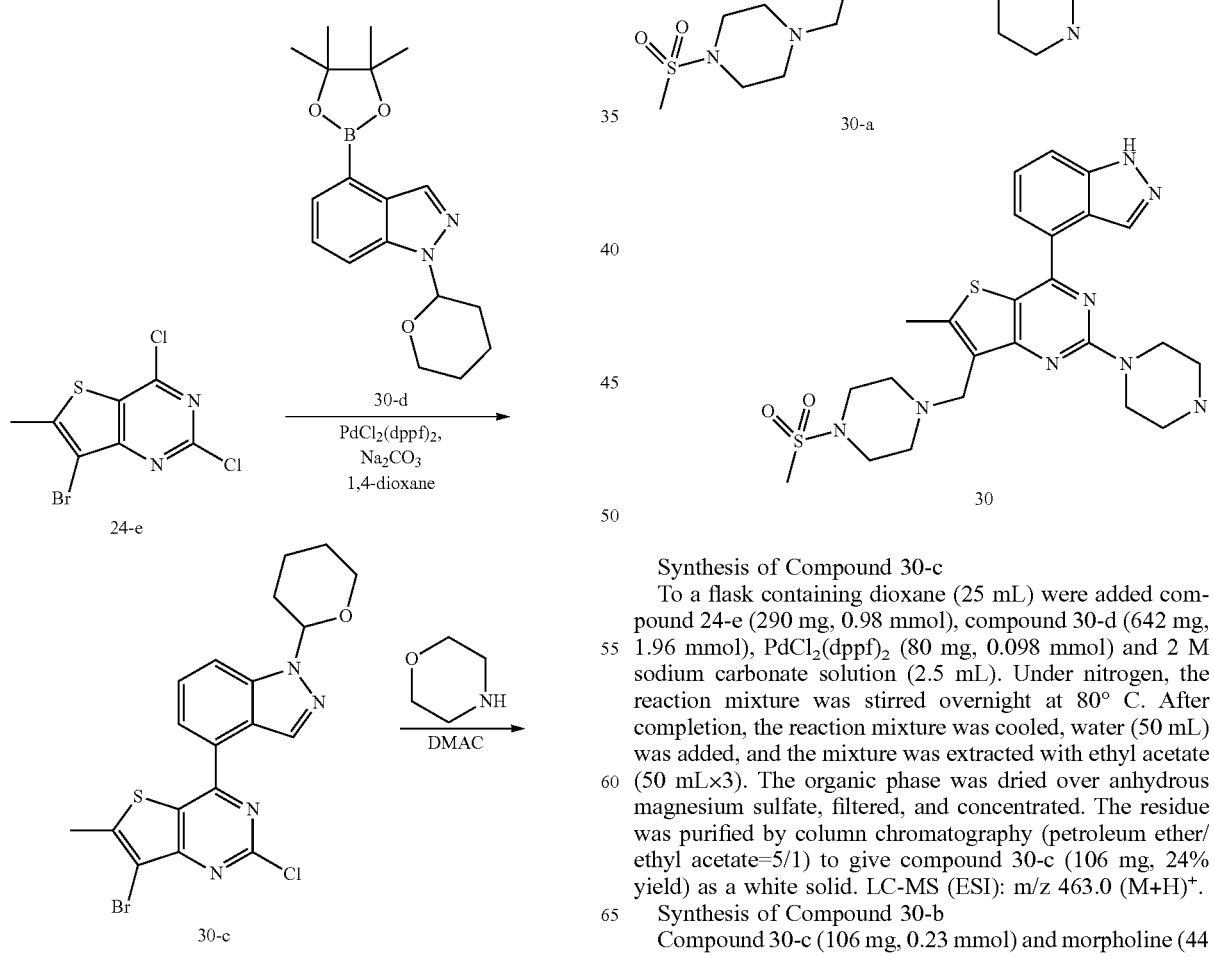

Synthesis of Compound 30-c

To a flask containing dioxane (25 mL) were added compound 24-e (290 mg, 0.98 mmol), compound 30-d (642 mg, 1.96 mmol), PdCl$_2$(dppf)$_2$ (80 mg, 0.098 mmol) and 2 M sodium carbonate solution (2.5 mL). Under nitrogen, the reaction mixture was stirred overnight at 80° C. After completion, the reaction mixture was cooled, water (50 mL) was added, and the mixture was extracted with ethyl acetate (50 mL×3). The organic phase was dried over anhydrous magnesium sulfate, filtered, and concentrated. The residue was purified by column chromatography (petroleum ether/ethyl acetate=5/1) to give compound 30-c (106 mg, 24% yield) as a white solid. LC-MS (ESI): m/z 463.0 (M+H)+.

Synthesis of Compound 30-b

Compound 30-c (106 mg, 0.23 mmol) and morpholine (44 mg, 0.50 mmol) were dissolved in DMAC (3 mL), the reaction solution was stirred overnight at 94° C. under nitrogen. In the next day, the reaction mixture was cooled to room temperature. Water (6 mL) was added. The precipitated solid was filtered. The filter cake was washed with water, dried to give compound 30-b (125 mg, yield 90%) as a light yellow solid. LC-MS (ESI): m/z 514.1 (M+H)⁺.

Synthesis of Compound 30-a

To a microwave tube containing THF (1.0 mL) and water (0.1 mL) were added compound 30-b (125 mg, 0.25 mmol), compound 2-a (123 mg, 0.50 mmol), palladium acetate (6 mg, 0.025 mmol), X-phos (12 mg, 0.025 mmol) and cesium carbonate (245 mg, 0.75 mmol). The mixture was put into a microwave and stirred for 1 hour at 125° C., 150 W, under nitrogen. After cooling, the reaction mixture was filtered and washed with tetrahydrofuran. The filtrate and washings were combined and concentrated. The residue was purified by Prep-TLC (DCM/MeOH=20/1) to give compound 30-a (76 mg, 51% yield) as a yellow solid. LC-MS (ESI): m/z 612.2 (M+H)⁺.

Synthesis of Compound 30

Compound 30-a (76 mg, 0.124 mmol) was dissolved in methanol (4.5 mL) and water (1.5 mL), and to the solution was added methanesulfonic acid (60 mg, 0.62 mmol). Under nitrogen, the reaction mixture was stirred, first at room temperature for 1 hour, and then at 65° C. overnight. The reaction mixture was cooled to room temperature, saturated sodium bicarbonate solution was added dropwise to pH 7-8, and extracted with dichloromethane (10 mL×3). The organic phase was washed with saturated brine (30 mL), dried over anhydrous over sodium sulfate, filtered, and concentrated. The residue was purified by Prep-TLC (DCM/MeOH=10/1) to give compound 30 (60 mg, 92% yield) as a light yellow solid. LC-MS (ESI): m/z 528.2 (M+H)⁺. ¹H NMR (500 MHz, CDCl₃-CD₃OD): δ 8.54 (s, 1H), 7.85 (d, 1H, J=7.0 Hz), 7.68 (d, 1H, J=8.5 Hz), 7.54 (t, 1H, J=7.0 Hz), 3.97 (t, 4H, J=5.0 Hz), 3.87 (t, 4H, J=5.0 Hz), 3.83 (s, 2H), 3.24 (s, 4H), 2.78 (s, 3H), 2.70 (t, 4H, J=4.5 Hz), 2.63 (s, 3H).

Synthetic Route of Compound 31

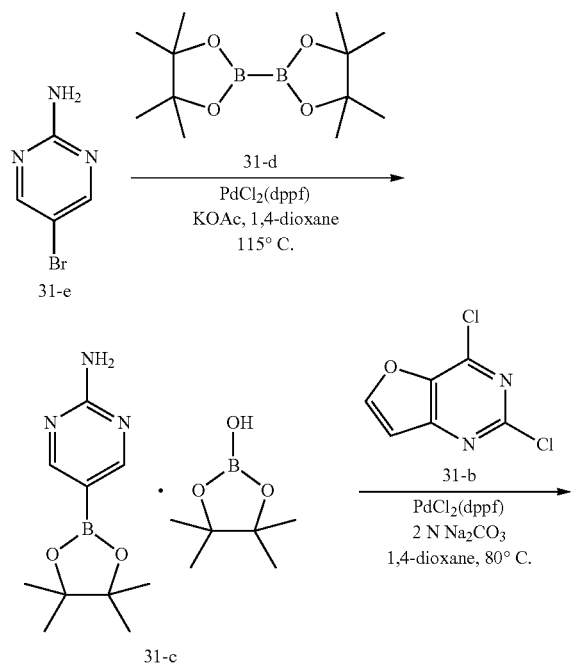

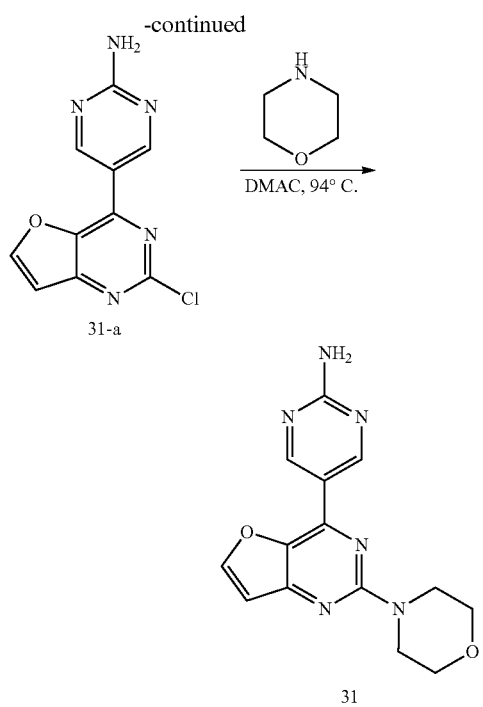

Synthesis of Compound 31-c

To a 1000 mL dry flask were added compound 31-e (20 g, 115 mmol), compound 31-d (32.2 g, 126.5 mmol), PdCl₂(dppf)*CH₂Cl₂ (4.68 g, 5.75 mmol), KOAc (33.86 g, 345 mmol) and 1,4-dioxane (600 mL). Under nitrogen, the reaction mixture was refluxed overnight at 115° C. The reaction mixture was cooled to room temperature. Ethyl acetate (1000 mL) was added, and the mixture was placed in ultrasound for 15 minutes, filtered. The organic phase was successively washed with water (1000 mL×2), brine (1000 mL), dried over anhydrous sodium sulfate, filtered through a short silica gel column (about 5 cm height) and concentrated. The crude product was treated with dichloromethane/petroleum ether (1/3), filtered, washed with petroleum ether. The resulting solid was refluxed in diethyl ether and filtered to give title compound 31-c (18.65 g, yield 45%) as an off-white solid. ¹H NMR (400 MHz, DMSO): δ 8.37 (s, 2H), 7.94 (s, 1H), 7.04 (s, 2H), 3.34 (s, 1H), 1.26 (s, 12H), 1.16 (s, 12H).

Synthesis of Compound 31-a

To a reaction flask were added compound 31-c (0.088 mmol), compound 31-b (according to the synthesis procedure in the patent: WO 2011/079230 A2) (15 mg, 0.080 mmol), PdCl₂(dppf) (3 mg, 0.004 mmol), 2 N aqueous sodium carbonate solution (0.12 mL, 0.24 mmol) and 1,4-dioxane (3 mL). Under nitrogen, the mixture was stirred overnight at 80° C. After the reaction mixture was concentrated, the residue was diluted with water (15 mL), and the aqueous phase was extracted with dichloromethane (15 mL×2). The organic layers were combined and washed successively with water and saturated brine, dried over anhydrous sodium sulfate, filtered, and concentrated to give crude product 31-a (35 mg) which was used directly in the next reaction without further purification. LC-MS (ESI): m/z=248.1 [M+H]⁺.

Synthesis of Compound 31

A mixture of compound 31-a (35 mg, 0.142 mmol), morpholine (62 mg, 0.71 mmol) and N, N-dimethylacetamide (2 mL) was heated to 94° C. and stirred overnight. After cooling to room temperature the reaction mixture was concentrated and the residue was diluted with ethyl acetate, washed with aqueous ammonia, and the organic phase was separated and dried over anhydrous sodium sulfate, concentrated. The residue was purified by HPLC to afford compound 31 (8 mg, 19.0%). LC-MS (ESI): m/z=299.1 [M+H]$^+$.
$^1$H NMR (400 MHz, CDCl$_3$): δ 9.26 (2H, s), 7.79 (1H, d, J=2.0 Hz), 6.69 (1H, d, J=2.4 Hz), 6.32 (2H, s), 3.80-3.82 (4H, m), 3.75-3.77 (4H, m).

Synthetic Route of Compound 32

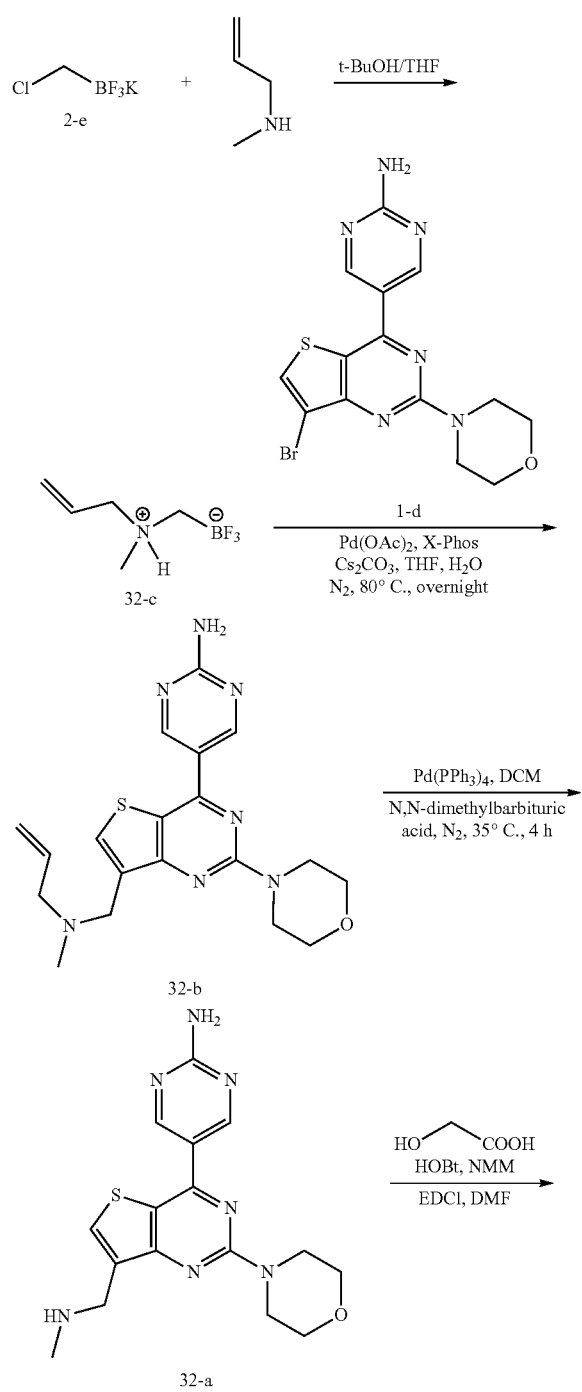

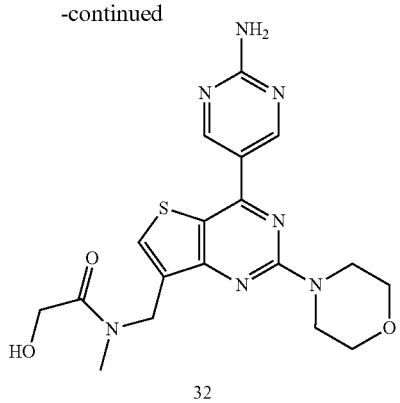

Synthesis of Compound 32-c

To a sealed tube were added compound 2-e (3.12 g, 20.0 mmol), methyl allyl amine (3.4 mL, 40.0 mmol), THF (11 mL), tert-butanol (5 mL). Under nitrogen, the reaction mixture was stirred overnight at 80° C. In the next day, the reaction mixture was concentrated. To the reaction mixture was added acetone. After refluxing, diethyl ether was slowly added to make precipitation, filtered, and the filter cake was dried to give compound 32-c (3.12 g, 69%) as a white solid.
$^1$H NMR (400 MHz, CDCl$_3$): δ 8.62 (1H, brs), 5.77-5.99 (1H, m), 5.35-5.51 (2H, m), 3.56 (2H, d, J=6.8 Hz), 2.59 (3H, s), 1.92 (2H, brs).

Synthesis of Compound 32-b

To a microwave tube were added compound 1-d (100 mg, 0.246 mmol), compound 32-c (189 mg, 1.23 mmol), palladium acetate (6 mg, 0.0246 mmol), X-Phos (12 mg, 0.0246 mmol), cesium carbonate (240 mg, 0.738 mmol), THF (1.0 mL) and water (0.1 mL). Under nitrogen, the reaction mixture was stirred overnight at 80° C. After completion, the reaction mixture was filtered, washed with THF and the filtrate was concentrated. The residue was purified by Prep-TLC (CH$_2$Cl$_2$/MeOH=20/1) to afford compound 32-b (22 mg, yield 23%) as a pale yellow solid. LC-MS (ESI): m/z 398.2 [M+H]$^+$.

Synthesis of Compound 32-a

Compound 32-b (48 mg, 0.12 mmol), tetrakis(triphenylphosphine) palladium (14 mg, 0.012 mmol) and N, N-dimethyl-barbituric acid (57 mg, 0.36 mmol) were dissolved in chloroethane (12 mL) and the reaction mixture was stirred at 35° C. for 4 hours under nitrogen. The reaction mixture was concentrated, and the residue was dissolved in ethyl acetate (30 mL), washed with 0.1 M sodium carbonate and (10 mL×2). The organic phase was dried over anhydrous sodium sulfate, filtered, and concentrated to give compound 32-a (13 mg, yield 30%) as a yellow solid. LC-MS (ESI): m/z 358.1 [M+H]$^+$.

Synthesis of Compound 32

Compound 32-a (16 mg, 0.045 mmol) and glycolic acid (4 mg, 0.054 mmol) were dissolved in DMF (3 mL), and then were added HOBt (10 mg, 0.068 mmol), NMM (15 ul, 0.135 mmol) and EDC.HCl (13 mg, 0.068 mmol) one by one. After the reaction mixture was stirred at room temperature overnight, water (6 mL) was added to quench the reaction. The reaction mixture was extracted with dichloromethane (10 mL×3), and the organic phase was washed with brine (30 mL×2), dried over anhydrous sodium sulfate, filtered, and concentrated. The crude product was purified by Prep-HPLC to afford compound 32 (14 mg, yield 74%) as a yellow solid. LC-MS (ESI): m/z 416.1 [M+H]$^+$. $^1$H NMR (400 MHz, CDCl$_3$-MeOD): δ 9.02 (s, 2H), 7.79 (s, 1H), 4.74 (s, 1H), 4.47 (s, 2H), 4.09 (s, 2H), 3.85 (t, 4H, J=4.4 Hz), 3.77 (t, 4H, J=4.0 Hz), 2.91 (s, 3H).

Synthetic Route of Compound 33

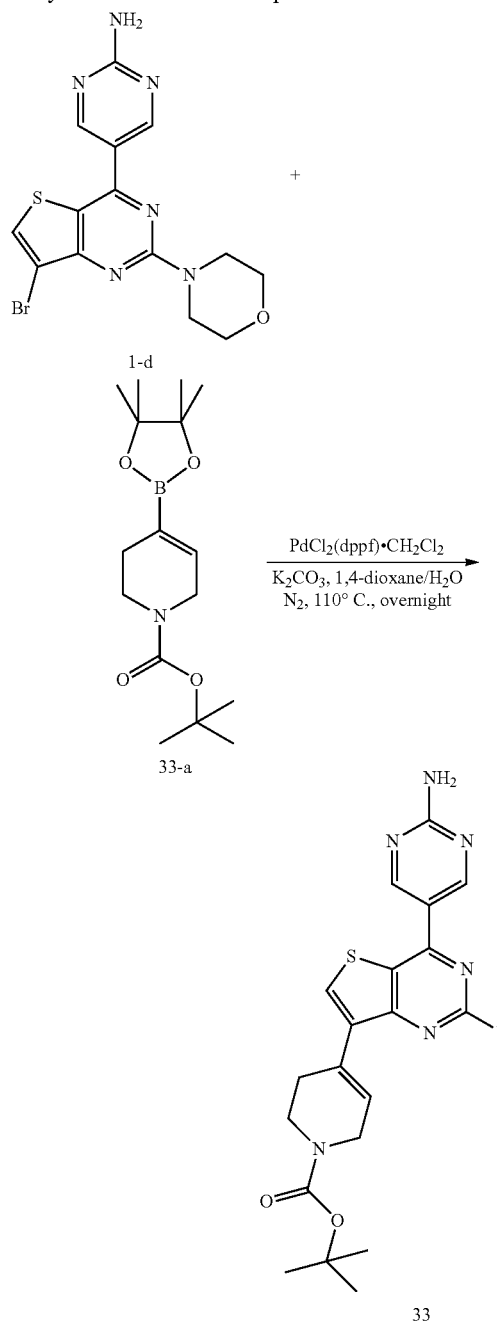

Synthesis of Compound 33

Compound 1-d (300 mg, 0.756 mmol), compound 33-a (according to the synthesis procedures in patent: WO 2008/088881) (284 mg, 0.918 mmol), PdCl$_2$(dppf).CH$_2$Cl$_2$ (63 mg, 0.077 mmol), potassium carbonate (317 mg, 2.23 mmol) and dioxane (25 mL) were added to a flask, and the mixture was stirred overnight at 110° C. under nitrogen. The reaction mixture was cooled, diluted with ethyl acetate (100 mL), washed with water (50 mL). The organic phase was dried over anhydrous sodium sulfate, filtered, and concentrated. The crude product was purified by Prep-HPLC to give compound 33 (151 mg, yield 40%) as a yellow solid. LC-MS (ESI): m/z 496.2 [M+H]$^+$. $^1$H NMR (500 MHz, CDCl$_3$-MeOD): δ 9.09 (s, 2H), 7.67 (s, 1H), 7.24 (s, 1H), 4.17 (s, 2H), 3.90 (s, 4H), 3.87 (s, 4H), 3.70 (t, 2H, J=5.0 Hz), 2.66 (s, 2H), 1.50 (s, 9H).

Synthetic Route of Compound 34

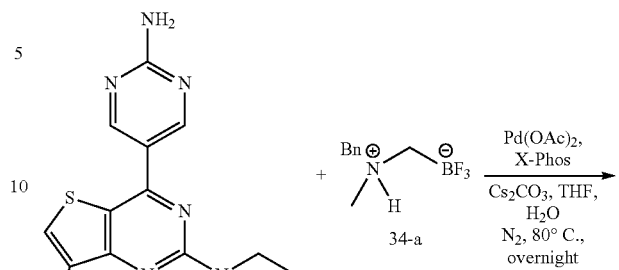

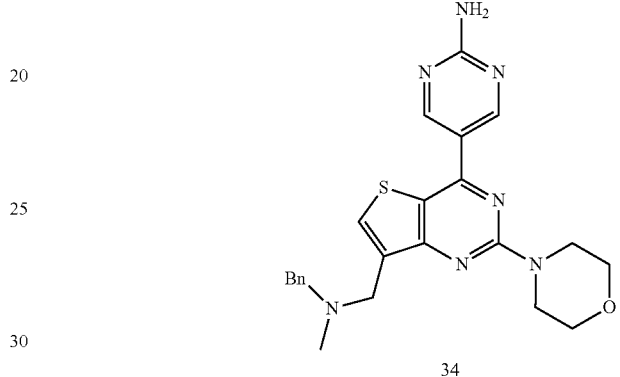

Synthesis of Compound 34

To a microwave tube were added compound 1-d (600 mg, 1.53 mmol), compound 34-a (according to the synthesis procedures in reference: J. Org Chem 2011, 76, 2762-2769) (466 mg, 2.3 mmol), palladium acetate (34 mg, 0.153 mmol), X-Phos (73 mg, 0.153 mmol), cesium carbonate (1.495 g, 4.59 mmol), THF (6.0 mL) and water (0.6 mL). Under nitrogen, the reaction mixture was stirred overnight at 80° C., filtered, rinsed with THF, and the filtrate was concentrated. The crude product was purified by Prep-TLC (DCM/MeOH=20/1) and then washed with methylene chloride/diethyl ether (1/4) and ether to give compound 34 (510 mg, yield 75%) as a yellow solid. LC-MS (ESI): m/z 448.2 [M+H]$^+$. $^1$H NMR (500 MHz, CDCl$_3$-MeOD): δ 9.10 (s, 2H), 7.86 (s, 1H), 7.39 (d, 2H, J=7.0 Hz), 7.35 (t, 3H, J=7.5 Hz), 3.89 (t, 4H, J=5.0 Hz), 3.86 (s, 2H), 3.84 (t, 4H, J=4.5 Hz), 3.64 (s, 2H), 2.31 (s, 3H).

Synthetic Route of Compound 35

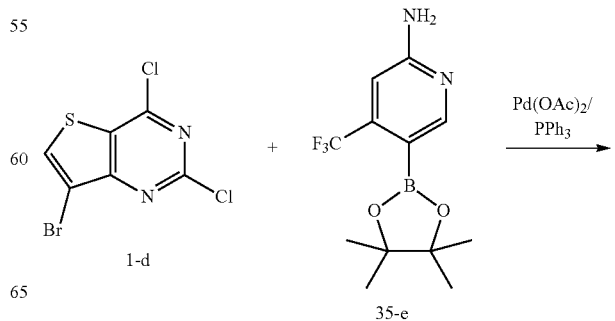

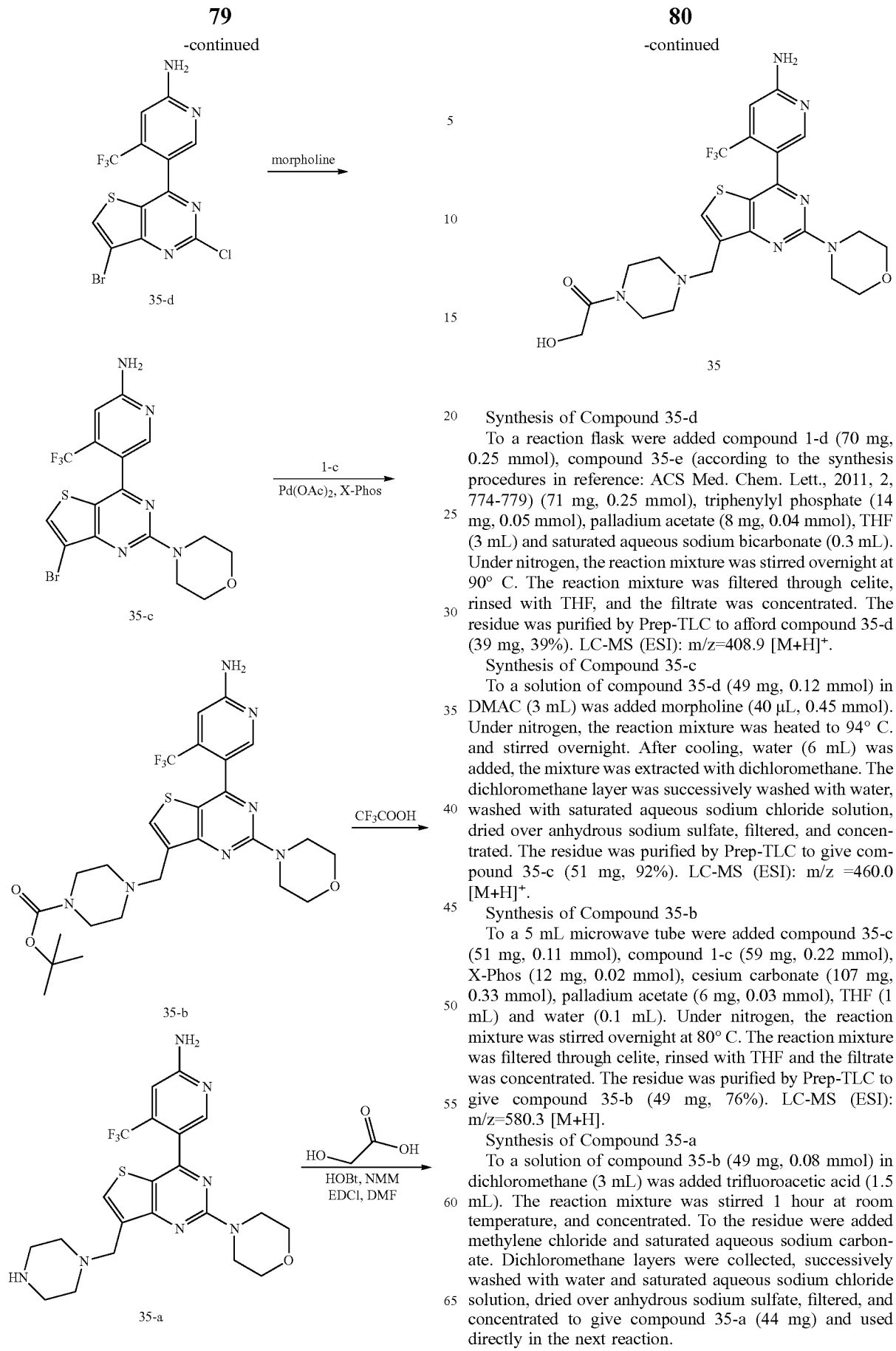

Synthesis of Compound 35-d

To a reaction flask were added compound 1-d (70 mg, 0.25 mmol), compound 35-e (according to the synthesis procedures in reference: ACS Med. Chem. Lett., 2011, 2, 774-779) (71 mg, 0.25 mmol), triphenylyl phosphate (14 mg, 0.05 mmol), palladium acetate (8 mg, 0.04 mmol), THF (3 mL) and saturated aqueous sodium bicarbonate (0.3 mL). Under nitrogen, the reaction mixture was stirred overnight at 90° C. The reaction mixture was filtered through celite, rinsed with THF, and the filtrate was concentrated. The residue was purified by Prep-TLC to afford compound 35-d (39 mg, 39%). LC-MS (ESI): m/z=408.9 [M+H]$^+$.

Synthesis of Compound 35-c

To a solution of compound 35-d (49 mg, 0.12 mmol) in DMAC (3 mL) was added morpholine (40 μL, 0.45 mmol). Under nitrogen, the reaction mixture was heated to 94° C. and stirred overnight. After cooling, water (6 mL) was added, the mixture was extracted with dichloromethane. The dichloromethane layer was successively washed with water, washed with saturated aqueous sodium chloride solution, dried over anhydrous sodium sulfate, filtered, and concentrated. The residue was purified by Prep-TLC to give compound 35-c (51 mg, 92%). LC-MS (ESI): m/z =460.0 [M+H]$^+$.

Synthesis of Compound 35-b

To a 5 mL microwave tube were added compound 35-c (51 mg, 0.11 mmol), compound 1-c (59 mg, 0.22 mmol), X-Phos (12 mg, 0.02 mmol), cesium carbonate (107 mg, 0.33 mmol), palladium acetate (6 mg, 0.03 mmol), THF (1 mL) and water (0.1 mL). Under nitrogen, the reaction mixture was stirred overnight at 80° C. The reaction mixture was filtered through celite, rinsed with THF and the filtrate was concentrated. The residue was purified by Prep-TLC to give compound 35-b (49 mg, 76%). LC-MS (ESI): m/z=580.3 [M+H].

Synthesis of Compound 35-a

To a solution of compound 35-b (49 mg, 0.08 mmol) in dichloromethane (3 mL) was added trifluoroacetic acid (1.5 mL). The reaction mixture was stirred 1 hour at room temperature, and concentrated. To the residue were added methylene chloride and saturated aqueous sodium carbonate. Dichloromethane layers were collected, successively washed with water and saturated aqueous sodium chloride solution, dried over anhydrous sodium sulfate, filtered, and concentrated to give compound 35-a (44 mg) and used directly in the next reaction.

Synthesis of Compound 35

To a solution of compound 35-a (44 mg, 0.092 mmol) in DMF (2 mL) were added glycolic acid (10 mg, 0.13 mmol), NMM (35 μL, 0.313 mmol), HOBt (20 mg, 0.147 mmol) and EDCI (27 mg, 0.141 mmol). The reaction mixture was stirred overnight at 27° C. To the reaction mixture were added water and dichloromethane. The dichloromethane layers were collected, successively washed with water and saturated aqueous sodium chloride solution, dried over anhydrous sodium sulfate, filtered, and concentrated. The residue was purified by Prep-HPLC to give compound 35 (21 mg, 48%). LC-MS (ESI): m/z=538.2 [M+H]$^+$. $^1$H NMR (400 MHz, CDCl$_3$): δ 8.46 (1H, s), 7.74 (1H, s), 6.90 (1H, s), 4.99 (2H, s), 4.15 (2H, s), 3.82-3.92 (6H, m), 3.75-3.82 (4H, m), 3.60-3.75 (3H, m), 3.31 (2H, t, J=4.8 Hz), 2.51-2.68 (4H, m).

Synthetic Route of Compound 36

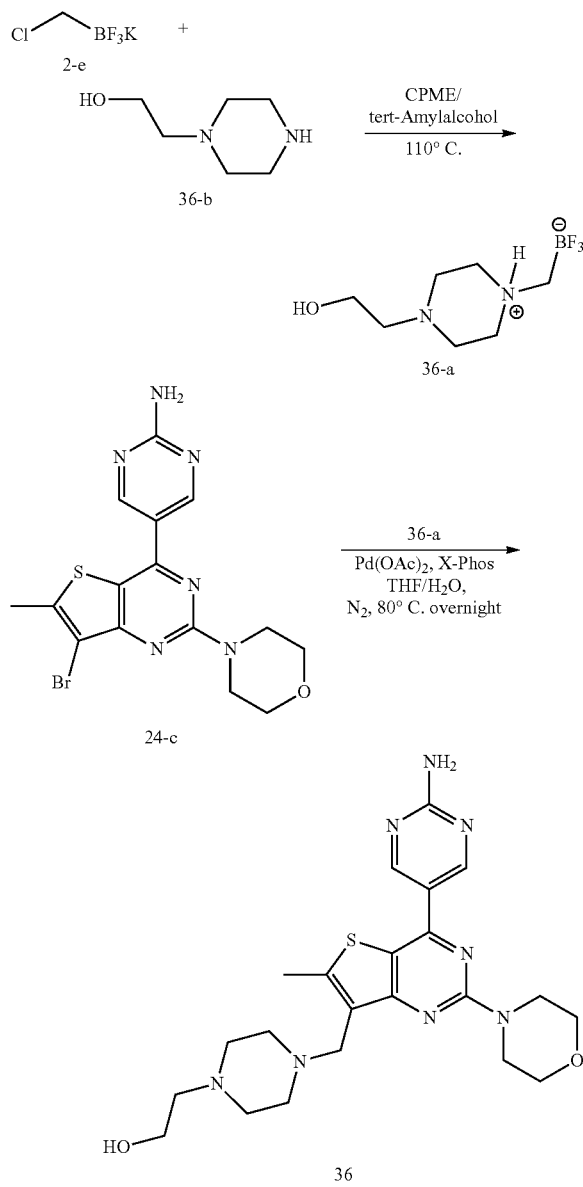

Synthesis of Compound 36-a

To a sealed tube were added compound 2-e (1.26 g, 8.07 mmol), compound 36-b (1.05 g, 8.07 mmol), cyclopentyl methyl ether (CPME) (24 mL) and tert-amyl alcohol (8 mL). Under nitrogen, the mixture was stirred overnight at 110° C. The reaction mixture was concentrated, acetone was added to the residue and refluxed, and then diethyl ether was slowly added to make precipitation, filtered, and the filter cake was dried to give compound 36-a (1.04 g, 45%) which was used directly in the next reaction.

Synthesis of Compound 36

Compound 24-c (100 mg, 0.246 mmol), compound 36-a (261 mg, 1.23 mmol), palladium acetate (6 mg, 0.025 mmol), X-Phos (12 mg, 0.025 mmol), cesium carbonate (240 mg, 0.738 mmol), THF (1.0 mL) and water (0.1 mL) were added in a microwave tube. Under nitrogen, the reaction mixture was stirred overnight at 80° C. After cooling, the mixture was filtered and rinsed with THF, the filtrate and washings were concentrated. The crude product was purified by Prep-HPLC to afford compound 36 (20 mg, yield 18%) as a pale yellow solid. LC-MS (ESI): m/z 471.3 [M+H]$^+$. $^1$H NMR (500 MHz, CDCl$_3$): δ 9.07 (s, 2H), 3.91 (t, 4H, J=5.0 Hz), 3.84 (t, 4H, J=5.0 Hz), 3.77 (s, 2H), 3.62 (t, 2H, J=5.0 Hz), 2.65 (s, 3H), 2.59 (s, 4H), 2.54 (t, 6H, J=5.0 Hz).

Biological Effect Example 1 PI3Kα and PI3Kδ Enzymatic Inhibitory Activity IC50 Assay 1. Buffer preparation: 50 mM HEPES, pH 7.5, 3 mM MgCl$_2$, 1 mM EGTA, 100 mM NaCl, 0.03% CHAPS.
2. Compound was formulated in 100% DMSO in a concentration gradient, deposited to a 384-well plate to make final DMSO concentration of 1%.
3. PI3Kα and PI3Kδ enzymes were diluted to be the optimum concentration with the following buffer: 50 mM HEPES, pH 7.5, 3 mM MgCl$_2$, 1 mM EGTA, 100 mM NaCl, 0.03% CHAPS, 2 mM DTT. Transferred to a 384-well plate and incubated with the compound for a certain time.
4. Substrate was diluted to an optimum concentration with following buffer: 50 mM HEPES, pH 7.5, 3 mM MgCl$_2$, 1 mM EGTA, 100 mM NaCl, 0.03% CHAPS, 2 mM DTT, 50 μM PIP2, Km ATP. The reaction was performed in a 384-well plate for 1 h at room temperature for PI3Kα and 2 hrs at room temperature for PI3Kδ.
5. Read the conversion rate using Caliper Reader, and calculate the inhibition rate as the average of two tests.

Table 1 lists the representative compounds and their PI3Kδ and PI3Kα IC50 values:

TABLE 1

| Compound code | IC50 on PI3Kα (nM) | IC50 on PI3Kδ (nM) |
| --- | --- | --- |
| 1 | 9.5 | 18 |
| 6 | 57 | 62 |
| 11 | 13.1 | 28.3 |
| 12 | 232 | 190 |
| 13 | 265 | 327 |
| 15 | 104 | 200 |
| 17 | 245 | 65.4 |
| 18 | 12.0 | 12.6 |
| 19 | 51.4 | 31.9 |
| 20 | 46.2 | 52.0 |
| 21 | 35 | 4.7 |
| 22 | 77 | 11 |
| 23 | 202 | 16 |
| 24 | 18.9 | 8.3 |
| 25 | 56 | 13 |
| 26 | 141 | 41 |
| 27 | 76 | 18 |
| 28 | 24 | 38 |
| 29 | 18 | 7 |
| 30 | 262.2 | 60.4 |

TABLE 1-continued

| Compound code | IC50 on PI3Kα (nM) | IC50 on PI3Kδ (nM) |
|---|---|---|
| 31 | 26 | 290 |
| 32 | 32 | 137 |
| 36 | 157 | 56 |

Biological Effect Example 2 Cell Proliferation Inhibition Assay

Cancer cell lines (A549, PC3, or U97-MG) in the logarithmic growth phase were plated at a density of about 3,000 per well in 96-well plates, 90 μL/well, using double wells for each concentration. Control wells containing corresponding concentration of vehicle and without cells were also prepared. After 24 hrs, positive control compound and example compounds were added to make 10 μL/well and final DMSO concentration of 0.5%. The cells were incubated with compounds for 72 hrs in the presence of 10% Invitrogen fetal bovine serum, 37° C., 5% $CO_2$. 5 mg/mL MTT solution was added to make 10 μL/well, and incubated for 4 hours at 37° C. A dd$H_2O$ solution (10% SDS, 5% isobutanol, 10 mmol/L HCl) was added to make 100 μL/well and incubated overnight at 37° C. OD values were measured using microplate reader under 580 nm and 680 nm, and the $IC_{50}$ values of the example compounds for cancer cells were calculated. Experimental data are shown in Table 2:

TABLE 2

| Compound code | A549 ($IC_{50}$, μM) | PC3 ($IC_{50}$, μM) | U87-MG ($IC_{50}$, μM) |
|---|---|---|---|
| 1 | 2.9944 | 3.1394 | 6.5683 |
| 6 | 4.6422 | 6.1073 | 7.4109 |
| 11 | 6.4383 | 10.098 | 12.1719 |
| 17 | 4.8164 | 5.3876 | 7.8122 |
| 18 | 3.637 | 2.3144 | 8.8724 |
| 19 | 3.9947 | 2.6073 | 8.078 |
| 24 | 2.7395 | 2.0674 | 9.3573 |
| 25 | 6.6843 | 3.0606 | 11.2905 |
| 26 | 9.3333 | 3.2792 | 19.7315 |
| 28 | 2.5991 | 1.9357 | 4.4577 |
| 29 | 2.7024 | 1.4867 | 3.7358 |

As shown in Table 1 and Table 2, the compounds of the present invention have very good inhibition to PI3 kinase activity and the proliferation of some cancer cells, and this kind of compounds is a potential drug for treating or preventing diseases or disorders associated with PI3 kinase, particularly cancer.

Biological Effect Example 3 Growth Inhibition Effects of Compounds to Malignant Glioma Cell U87MG Xenograft in Nude Mice Groups of nude mice were implanted subcutaneously in the right hind back with $4 \times 10^6$ U87MG cells. Start dosing when mean tumor volume reached approximately 150 (100-200) $mm^3$. Grouping method: before dosing, animals were weighted, tumor sizes were measured, and randomized according to the tumor size (randomized block design), 8 mice per group. A solvent (0.5% CMC-Na+0.2% Tween-80) was dosed once daily by oral gavage for solvent control group, and pre-determined dose of test compound was dosed once daily by oral gavage for a dosing group, for 20 consecutive days.

Tumor diameters were measured twice a week with a vernier caliper. Tumor volume was calculated with formula: $V=0.5a \times b^2$, a and b represent longer and shorter diameter of tumor. Antitumor efficacy of the test compound was evaluated with TGI (%) reflecting tumor growth inhibition rates, which is calculated as follows: TGI (%)=[1−(tumor volume of treating group at the end of dosing period−tumor volume of treating group in the beginin of dosing)/(tumor volume of vehicle group at the end of dosing period−tumor volume of vehicle group in the beginin of dosing)]×100%. Meanwhile, the weight of nude mice in each group was weighed twice weekly for a preliminary evaluation of compound toxicity. Experimental data are shown in Table 3.

TABLE 3

| Compound code | Body weight (g) | | Tumor size ($mm^3$) | | TGI (%) | p value |
|---|---|---|---|---|---|---|
| | D 0 | D 20 | D 0 | D 20 | | |
| Vehicle | 22.12 ± 0.35 | 24.11 ± 0.42 | 148.40 ± 13.65 | 873.04 ± 107.01 | — | — |
| GDC-0941 (25 mg/kg) | 22.24 ± 0.33 | 23.64 ± 0.42 | 149.86 ± 14.67 | 456.64 ± 68.28 | 57.65 | 0.005 |
| GDC-0941 (50 mg/kg) | 22.47 ± 0.41 | 23.57 ± 0.35 | 150.72 ± 16.35 | 396.57 ± 54.30 | 66.07 | 0.001 |
| 29 (20 mg/kg) | 22.40 ± 0.22 | 22.69 ± 0.36 | 148.62 ± 14.64 | 232.84 ± 48.68 | 88.38 | <0.001 |
| 29 (50 mg/kg) | 22.21 ± 0.33 | 21.99 ± 0.30 | 151.36 ± 14.64 | 130.48 ± 16.63 | 102.88 | <0.001 |
| 29 (150 mg/kg) | 22.76 ± 0.31 | 20.62 ± 0.28 | 148.16 ± 13.74 | 47.70 ± 10.16 | 113.86 | <0.001 |

Wherein the compound GDC-0941 (CAS No.: 957054-30-7) is a known inhibitor of PI3K. Its structure is as follows:

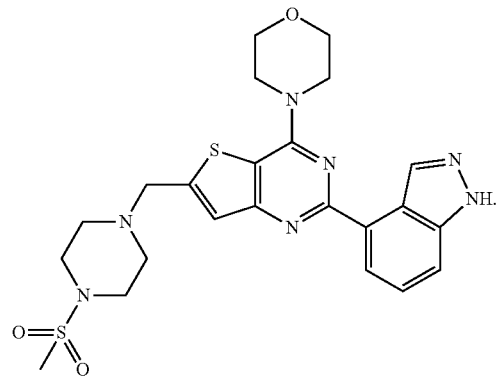

GDC-0941

As can be seen from Table 3, compound 29 has a strong in vivo anti-tumor activity, and its ability to inhibit tumor growth of malignant glioma cells U87MG xenograft in nude mice is significantly better than GDC-0941, and less toxic side effects, the tested mice can still torelate even the high dose (150 mg/kg).

What is claimed is:

1. A fused pyrimidine compound represented by formula I, a pharmaceutically acceptable salt, hydrate, and solvate thereof, an optical isomer or a prodrug thereof,

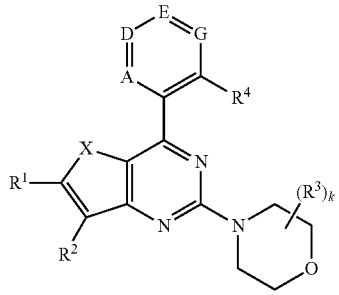

wherein:

X is S or O;

$R^1$ is hydrogen, deuterium, halogen, an alkyl, an alkoxy, an alkenyl, an alkynyl, a cycloalkyl, a heterocycloalkyl, an aryl or a heteroaryl;

$R^2$ is hydrogen, deuterium, halogen, CN, —$(CR^8R^9)_m$NR$^5$R$^6$, —$(CR^8R^9)_m$NR$^7$C(=Y)R$^5$, —$(CR^8R^9)_m$NR$^7$S(O)$_2$R$^5$, —$(CR^8R^9)_m$OR$^5$, —$(CR^8R^9)_m$S(O)$_2$R$^5$, —$(CR^8R^9)_m$S(O)$_2$NR$^5$R$^6$, —C(OR$^5$)R$^6$R$^8$, —C(=Y)R$^5$, —C(=Y)OR$^5$, —C(=Y)NR$^5$R$^6$, —C(=Y)NR$^7$OR$^5$, —C(=O)NR$^7$S(O)$_2$R$^5$, —C(=O)NR$^7$(CR$^8$R$^9$)$_m$NR$^5$R$^6$, —NR$^7$C(=Y)R$^6$, —NR$^7$C(=Y)OR$^6$, —NR$^7$C(=Y)NR$^5$R$^6$, —NR$^7$S(O)$_2$R$^5$, —NR$^7$S(O)$_2$NR$^5$R$^6$, —SR$^5$, —S(O)$_2$R$^5$, —S(O)$_2$NR$^5$R$^6$, —SC(=Y)R$^5$, —SC(=Y)OR$^5$, a $C_{1-12}$ alkyl, a $C_{2-8}$ alkenyl, a $C_{2-8}$ alkynyl, a $C_{3-12}$ carbocyclyl, a $C_{2-20}$ heterocyclyl, a $C_{6-20}$ aryl or a $C_{1-20}$ heteroaryl;

all of $R^3$ are the same or different from each other, and $R^3$ is selected from the group consisting of deuterium, halogen, $C_{1-6}$ alkyl, or any two of the $R^3$ may be linked by a single bond, $C_{1-6}$ alkylene or $C_{1-6}$ alkylene having one or more carbon atoms replaced by heteroatom, the heteroatom is O, N, or S;

A is N or CR$^{4a}$;

D is N or CR$^{4b}$;

E is N or CR$^{4d}$;

G is N or CR$^{4e}$;

A, D, E and G are not N at the same time;

each of $R^4$, $R^{4a}$, $R^{4b}$, $R^{4d}$ and $R^{4e}$ is independently hydrogen, halogen, —CN, an alkyl, an alkoxy, an alkenyl, an alkynyl, a cycloalkyl, a heterocycloalkyl, —NR$^5$R$^6$, —OR$^5$, —SR$^5$, —C(O)R$^5$, —NR$^5$C(O)R$^6$, —N(C(O)R$^6$)$_2$, —NR$^5$C(O)NR$^{5'}$R$^6$, —NR$^7$S(O)$_2$R$^5$, —C(=O)OR$^5$ or —C(=O)NR$^5$R$^6$, or $R^4$ or $R^{4d}$, with $R^{4e}$, and the atoms to which they are attached form a saturated, unsaturated or partially unsaturated 5-membered or 6-membered heterocycle, the 5-membered or 6-membered heterocycle contains at least two heteroatoms selected from O, N, or S, the 5-membered or 6-membered heterocycle is fused to the 6-membered ring containing A, D, E and G;

each of $R^5$, $R^{5'}$, $R^6$, $R^7$ and $R^{7'}$ is independently hydrogen, a $C_{1-12}$ alkyl, a $C_{2-8}$ alkenyl, a $C_{2-8}$ alkynyl, a $C_{3-12}$ carbocyclyl, a $C_{2-20}$ heterocyclyl, a $C_{6-20}$ aryl or a $C_{1-20}$ heteroaryl, or $R^5$, $R^6$ together with the nitrogen to which they are attached form an heterocycle optionally substituted by a substituent selected from the group consisting of: oxo, —(CH$_2$)$_m$OR$^7$, —NR$^7$R$^{7'}$, —CF$_3$, halogen, —SO$_2$R$^7$, —C(=O)R$^7$, —NR$^7$C(=Y)R$^{7'}$, —NR$^7$S(O)$_2$R$^{7'}$, —C(=Y)NR$^7$R$^{7'}$, $C_{1-12}$ alkyl, $C_{2-8}$ alkenyl, $C_{2-8}$ alkynyl, $C_{3-12}$ carbocyclyl, $C_{2-20}$ heterocyclyl, $C_{6-20}$ aryl and $C_{1-20}$ heteroaryl;

$R^8$ is hydrogen, deuterium, halogen, —CN, a hydroxy, an alkoxy, a cycloalkoxy, a $C_{1-12}$ alkyl, a $C_{2-12}$ alkenyl, a $C_{2-12}$ alkynyl, a $C_{3-12}$ cycloalkyl, a $C_{6-12}$ aryl, a 3-12 membered heterocycloalkyl or a 5-12 membered heteroaryl;

$(CR^8R^9)_m$ represents that m $(CR^8R^9)$ is connected, wherein each of $R^8$ and $R^9$ is the same or different from each other, and independently selected from hydrogen, deuterium, halogen, —CN, a hydroxy, an alkoxy, a $C_{1-12}$ alkyl, a $C_{2-12}$ alkenyl, a $C_{2-12}$ alkynyl, a $C_{3-12}$ cycloalkyl, a $C_{6-12}$ aryl, a 3-12 membered heterocycloalkyl or a 5-12 membered heteroaryl; or $R^8$, $R^9$ together with the atoms to which they are attached form a saturated or partially unsaturated $C_{3-12}$ carbocyclic ring or $C_{2-20}$ heterocyclic ring;

wherein the alkyl, alkenyl, alkynyl, cycloalkyl, carbocycle, heterocycle, heterocycloalkyl, aryl, or heteroaryl is optionally substituted by a substituent selected from the group consisting of: halogen, —CN, —CF$_3$, —NO$_2$, oxo, R$^5$, —C(=Y)R$^5$, —C(=Y)OR$^5$, —C(=Y)NR$^5$R$^6$, —(CR$^8$R$^9$)$_m$NR$^5$R$^6$, —(CR$^8$R$^9$)$_m$OR$^5$, —NR$^5$R$^6$, —NR$^7$C(=Y)R$^5$, —NR$^7$C(=Y)OR$^6$, —NR$^7$C(=Y)NR$^5$R$^6$, —(CR$^8$R$^9$)$_m$NR$^7$SO$_2$R$^5$, =NR$^7$, OR$^5$, —OC(=Y)R$^5$, —OC(=Y)OR$^5$, —OC(=Y)NR$^5$R$^6$, —OS(O)$_2$(OR$^5$), —OP(=Y)(OR$^5$)(OR$^6$), —OP(OR$^5$)(OR$^6$), —SR$^5$, —S(O)R$^5$, —S(O)$_2$R$^5$, —S(O)$_2$NR$^5$R$^6$, —S(O)(OR$^5$), —S(O)$_2$(OR$^5$), —SC(=Y)R$^5$, —SC(=Y)OR$^5$, —SC(=Y)NR$^5$R$^6$, $C_{1-12}$ alkyl, $C_{2-8}$ alkenyl, $C_{2-8}$ alkynyl, $C_{3-12}$ carbocyclyl, $C_{2-20}$ heterocyclyl, $C_{6-20}$ aryl or $C_{1-20}$ heteroaryl;

Y is O, S, or NR$^7$;

m and k are independently 0, 1, 2, 3, 4, 5 or 6.

2. The fused pyrimidine compound represented by formula I, the pharmaceutically acceptable salt, hydrate, and solvate thereof, the optical isomer or the prodrug thereof according to claim 1, wherein where $R^1$ is an alkyl, the alkyl is a $C_{1-3}$ alkyl.

3. The fused pyrimidine compound represented by formula I, the pharmaceutically acceptable salt, hydrate, and solvate thereof, the optical isomer or the prodrug thereof according to claim 1, wherein where each of $R^4$, $R^{4a}$, $R^{4b}$, $R^{4d}$ and $R^{4e}$ is independently halogen, the halogen is F, Cl, Br or I;

and/or where each of $R^4$, $R^{4a}$, $R^{4b}$, $R^{4d}$ and $R^{4e}$ is independently an alkyl, the alkyl is a $C_{1-6}$ alkyl;

and/or where each of $R^4$, $R^{4a}$, $R^{4b}$, $R^{4d}$ and $R^{4e}$ is independently an alkoxy, the alkoxy is a $C_{1-6}$ alkoxy.

4. The fused pyrimidine compound represented by formula I, the pharmaceutically acceptable salt, hydrate, and solvate thereof, the optical isomer or the prodrug thereof according to claim 1, wherein where each of $R^5$, $R^{5'}$, $R^6$, $R^7$ and $R^{7'}$ is independently a $C_{1-12}$ alkyl or a $C_{6-20}$ aryl, the $C_{1-12}$ alkyl is tert-butyl or methyl; the $C_{6-20}$ aryl is phenyl.

5. The fused pyrimidine compound represented by formula I, the pharmaceutically acceptable salt, hydrate, and solvate thereof, the optical isomer or the prodrug thereof according to claim 1, wherein where each of $R^5$, $R^{5'}$, $R^6$, $R^7$ and $R^{7'}$ is independently an alkyl, the alkyl is (S)-α-hydroxyethyl, (R)-α-hydroxyethyl, hydroxymethyl, or α-hydroxy isopropyl.

6. The fused pyrimidine compound represented by formula I, the pharmaceutically acceptable salt, hydrate, and solvate thereof, the optical isomer or the prodrug thereof according to claim 1, wherein where $R^2$ is a $C_{1-12}$ alkyl, the $C_{1-12}$ alkyl is a $C_{1-3}$ alkyl, the substituent of the $C_{1-3}$ alkyl is a $C_{2-20}$ heterocyclyl or —NR$^7$C(=Y)R$^5$, the $C_{2-20}$ heterocyclyl is optionally substituted by a substituent selected from the group consisting of: halogen, —CN, —CF$_3$, —NO$_2$, oxo, R$^5$, —C(=Y)R$^5$, —C(=Y)OR$^5$, —C(=Y)NR$^5$R$^6$, —(CR$^8$R$^9$)$_n$NR$^5$R$^6$, —(CR$^8$R$^9$)$_n$OR$^5$, —NR$^5$R$^6$, —NR$^7$C(=Y)R$^5$, —NR$^7$C(=Y)OR$^6$, —NR$^7$C(=Y)NR$^5$R$^6$, —(CR$^8$R$^9$)$_m$NR$^7$SO$_2$R$^5$, =NR$^7$, OR$^5$, —OC(=Y)R$^5$, —OC(=Y)OR$^5$, —OC(=Y)NR$^5$R$^6$, —OS(O)$_2$(OR$^5$), —OP(=Y)(OR$^5$)(OR$^6$), —OP(OR$^5$)(OR$^6$), —SR$^5$, —S(O)R$^5$, —S(O)$_2$R$^5$, —S(O)$_2$NR$^5$R$^6$, —S(O)(OR$^5$), —S(O)$_2$(OR$^5$), —SC(=Y)R$^5$, —SC(=Y)OR$^5$, —SC(=Y)NR$^5$R$^6$, C$_{1-3}$ alkyl, C$_{2-8}$ alkenyl, C$_{2-8}$ alkynyl, C$_{3-12}$ carbocyclyl, C$_{2-20}$ heterocyclyl, C$_{6-20}$ aryl or C$_{1-20}$ heteroaryl.

7. The fused pyrimidine compound represented by formula I, the pharmaceutically acceptable salt, hydrate, and solvate thereof, the optical isomer or the prodrug thereof according to claim 1, wherein: where R$^2$ is a C$_{1-12}$ alkyl and the substituent of the C$_{1-12}$ alkyl is a C$_{2-20}$ heterocyclyl, the C$_{2-20}$ heterocyclyl is piperazinyl or piperidinyl; the C$_{2-20}$ heterocyclyl is substituted by a C$_{1-3}$ alkyl, the C$_{1-3}$ alkyl is substituted by a hydroxy forming hydroxyl ethyl or α-hydroxy isopropyl; where the C$_{2-20}$ heterocyclyl has one heteroatom, the substituted position of the C$_{2-20}$ heterocyclyl is on its carbon atom or its heteroatom; where the C$_{-20}$ heterocyclyl has two or more heteroatoms, the substituted position of the C$_{2-20}$ heterocyclyl is on its heteroatom;

where R$^2$ is a C$_{2-20}$ heterocyclyl and the C$_{2-20}$ heterocyclyl is substituted by C(=Y)OR$^5$, the C$_{2-20}$ heterocyclyl is a C$_{4-5}$ saturated heterocyclyl containing one heteroatom and only one double bond, wherein the heteroatom is N, O or S.

8. The fused pyrimidine compound represented by formula I, the pharmaceutically acceptable salt, hydrate, and solvate thereof, the optical isomer or the prodrug thereof according to claim 1, wherein: the compound I has the following structure IA:

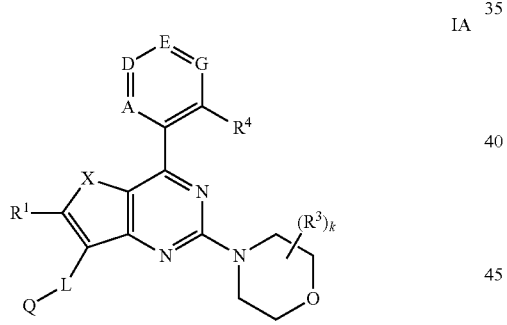

IA wherein Q is a C$_{2-20}$ heterocyclyl, and is optionally substituted by a substituent selected from the group consisting of: halogen, —CN, —CF$_3$, —NO$_2$, oxo, R$^5$, —C(=Y)R$^5$, —C(=Y)OR$^5$, —C(=Y)NR$^5$R$^6$, —(CR$^8$R$^9$)$_n$NR$^5$R$^6$, —(CR$^8$R$^9$)$_n$OR$^5$, —NR$^5$R$^6$, —NR$^7$C(=Y)R$^5$, —NR$^7$C(=Y)OR$^6$, —NR$^7$C(=Y)NR$^5$R$^6$, —(CR$^8$R$^9$)$_m$NR$^7$SO$_2$R$^5$, =NR$^7$, OR$^5$, —OC(=Y)R$^5$, —OC(=Y)OR$^5$, —OC(=Y)NR$^5$R$^6$, —OS(O)$_2$(OR$^5$), —OP(=Y)(OR$^5$)(OR$^6$), —OP(OR$^5$)(OR$^6$), —SR$^5$, —S(O)R$^5$, —S(O)$_2$R$^5$, —S(O)$_2$NR$^5$R$^6$, —S(O)(OR$^5$), —S(O)$_2$(OR$^5$), —SC(=Y)R$^5$, —SC(=Y)OR$^5$, —SC(=Y)NR$^5$R$^6$, C$_{1-12}$ alkyl, C$_{2-8}$ alkenyl, C$_{2-8}$ alkynyl, C$_{3-12}$ carbocyclyl, C$_{2-20}$ heterocyclyl, C$_{6-20}$ aryl or C$_{1-20}$ heteroaryl; L is a C$_{1-3}$ alkylene or absent;

or Q is —NR$^7$C(=Y)R$^5$, other groups and letters have the meanings given in claim 1.

9. The fused pyrimidine compound represented by formula I, the pharmaceutically acceptable salt, hydrate, and solvate thereof, the optical isomer or the prodrug thereof according to claim 8, wherein: the compound IA has a structure represented by a formula selected from the group consisting of:

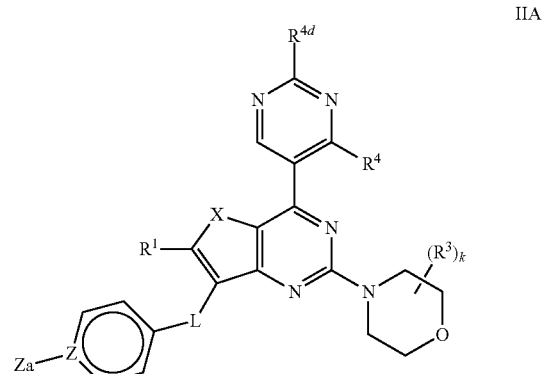

IIA

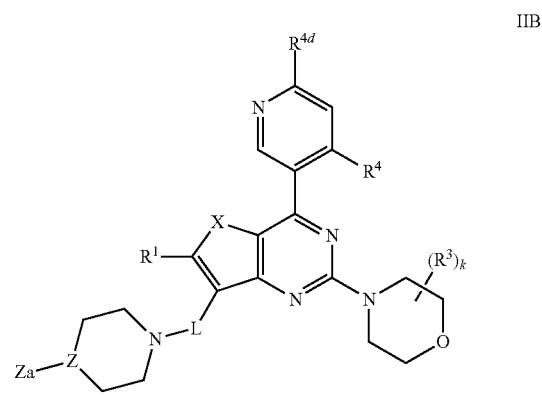

IIB

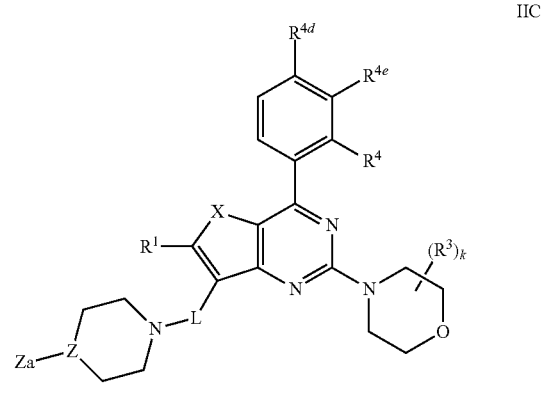

IIC

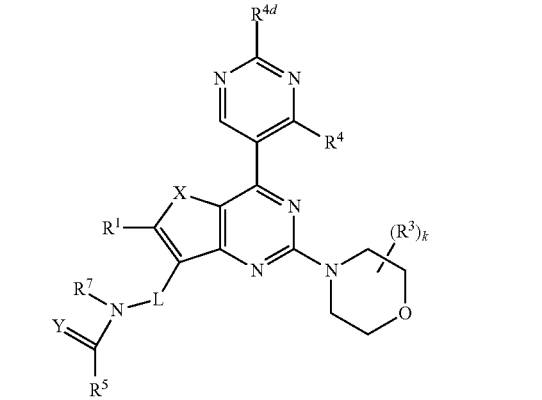

IID

IIE

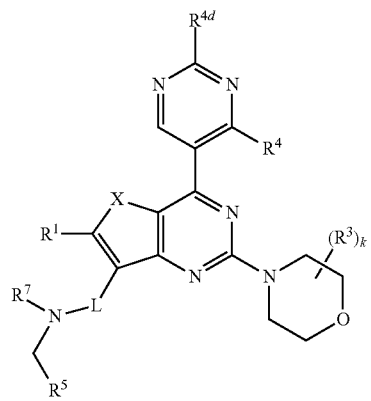

wherein, Z is N or CH, Za is —C(=Y)R⁵, —C(=Y)NR⁵R⁶, —S(O)R⁵, —S(O)₂R⁵, or a $C_{1-12}$ alkyl; other groups and letters have the meanings given above;

is a saturated, partially unsaturated or unsaturated heterocycle.

10. The fused pyrimidine compound represented by formula I, the pharmaceutically acceptable salt, hydrate, and solvate thereof, the optical isomer or the prodrug thereof according to claim 9, wherein: where Za is a $C_{1-12}$ alkyl, the $C_{1-12}$ alkyl is a substituted or unsubstituted $C_{1-3}$ alkyl whose substituent is a hydroxyl, and the hydroxyl together with the alkyl form hydroxyl ethyl or a-hydroxy isopropyl:
and/or, where

is a partially unsaturated heterocycle, only one double bond is contained.

11. The fused pyrimidine compound represented by formula I, the pharmaceutically acceptable salt, hydrate, and solvate thereof, the optical isomer or the prodrug thereof according to claim 9, wherein: the compound IIC has a structure represented by a formula selected from the group consisting of:

IICa

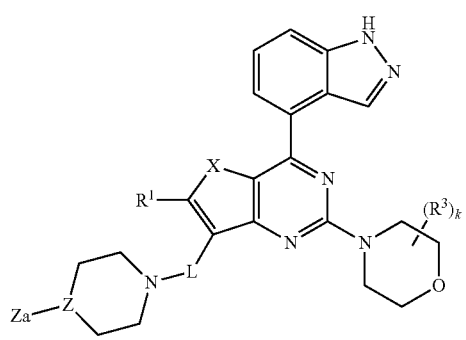

IICb

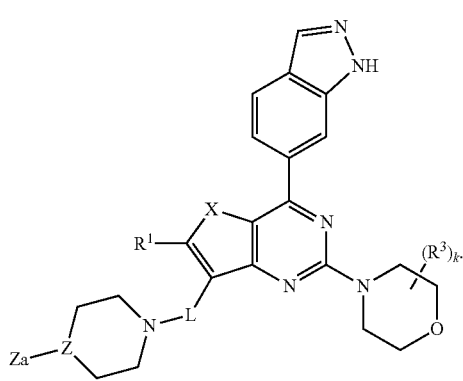

12. The fused pyrimidine compound represented by formula I, the pharmaceutically acceptable salt, hydrate, and solvate thereof, the optical isomer or the prodrug thereof according to claim 1, wherein: the

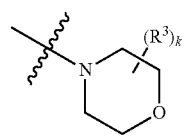

has a structure represented by a formula selected from the group consisting of:

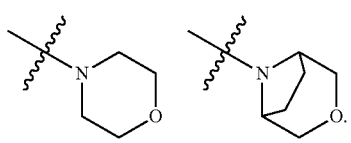 [SMILES: *N1CCOCC1 ; *N1C2CCC1COC2]

13. A fused pyrimidine compound, a pharmaceutically acceptable salt, hydrate, and solvate thereof, an optical isomer or a prodrug thereof wherein the compound has a structure represented by a formula selected from the group consisting of:

1

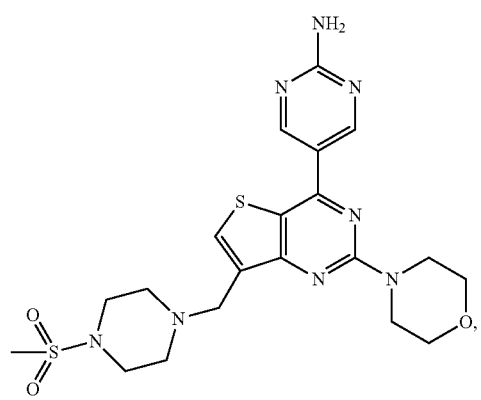

| | |
|---|---|
| 2 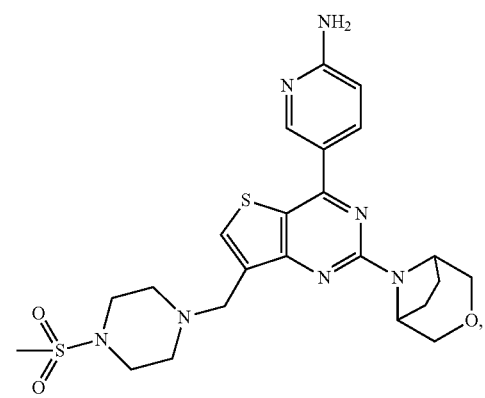 | 6 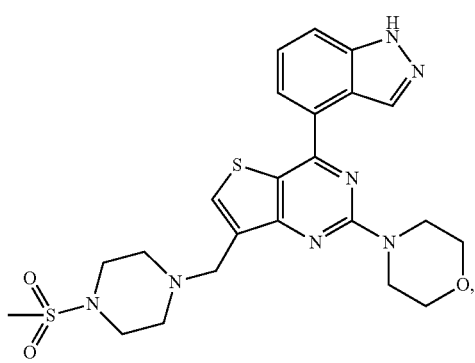 |
| 3 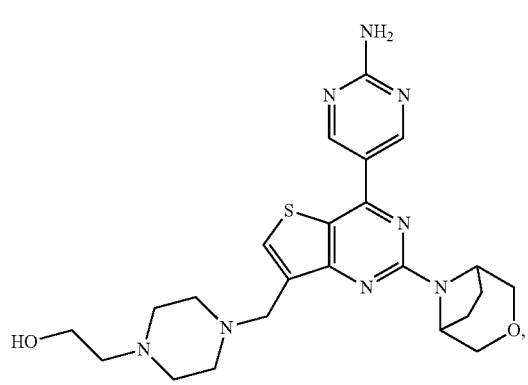 | 7 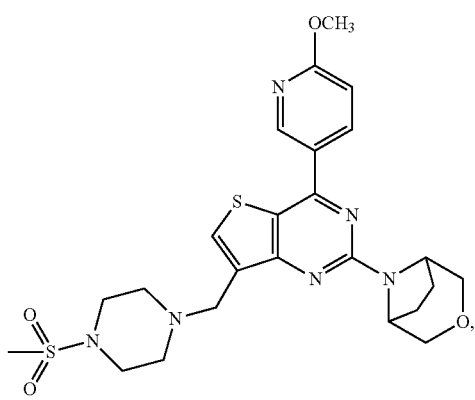 |
| 4 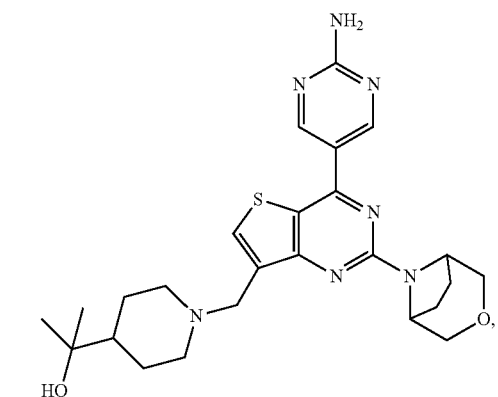 | 8 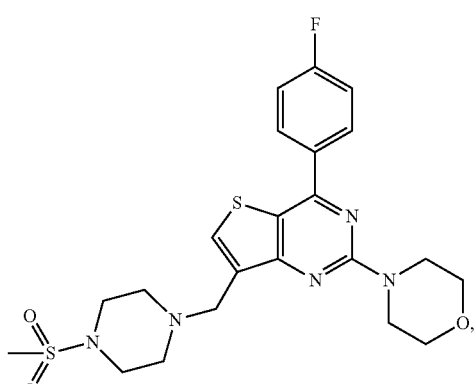 |
| 5 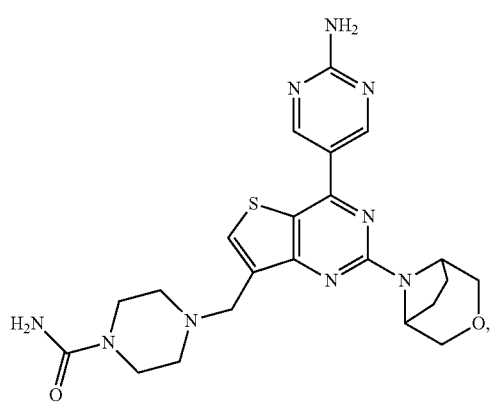 | 9 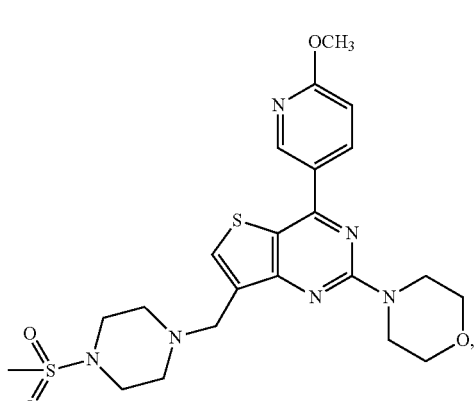 |

93
-continued
10
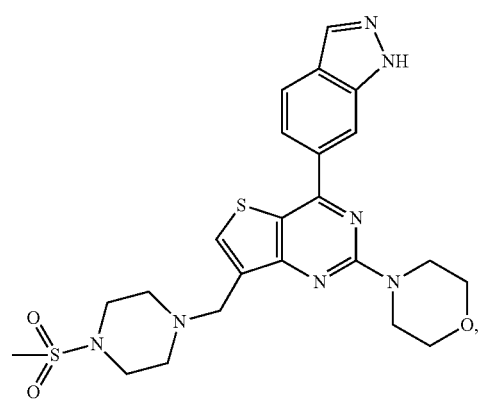
11
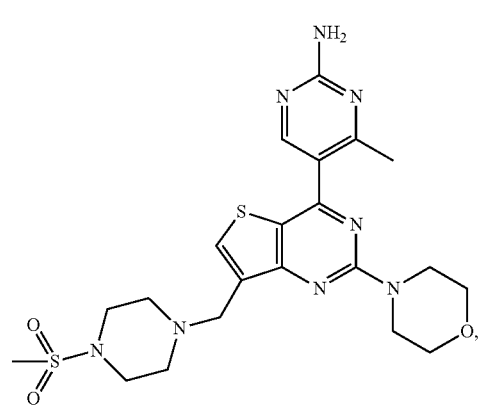
12
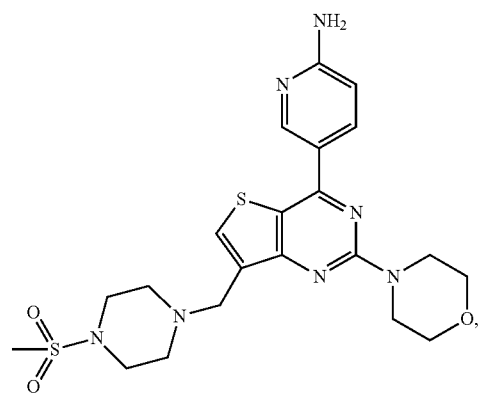
13
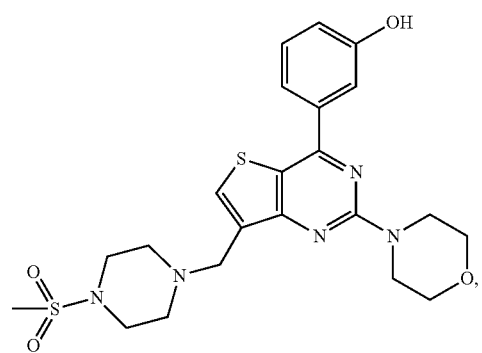
94
-continued
14
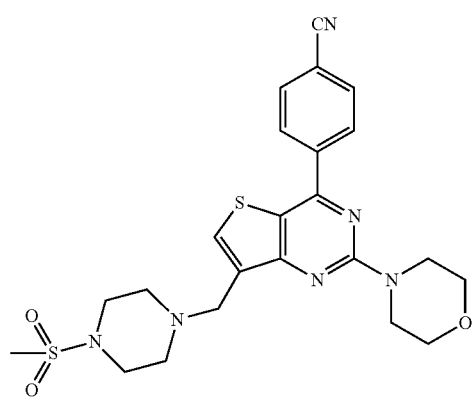
15
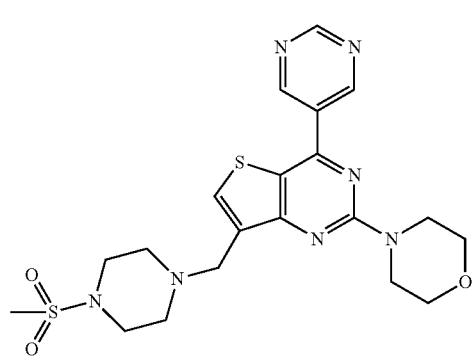
16
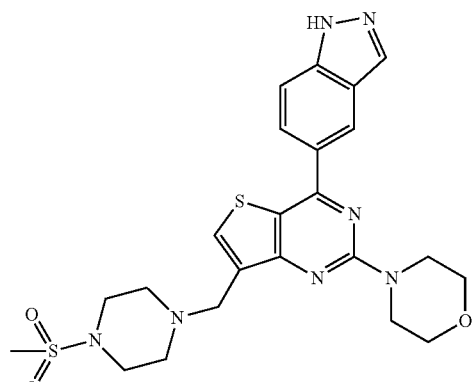
17
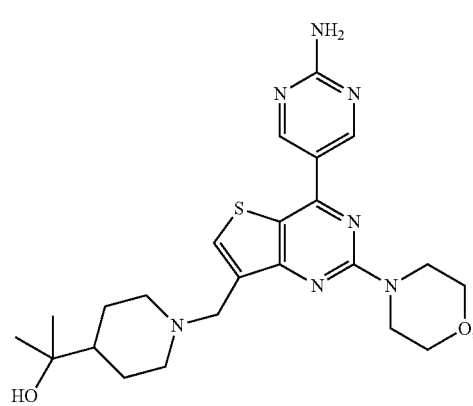

-continued
18
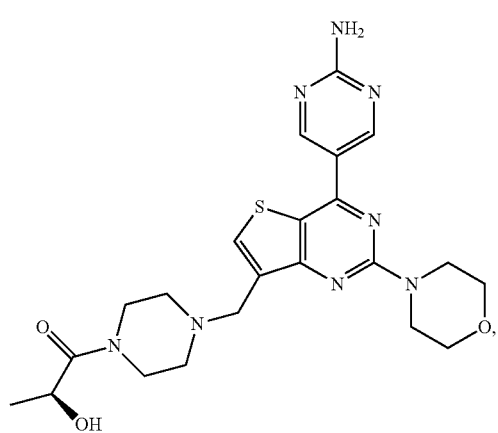
19
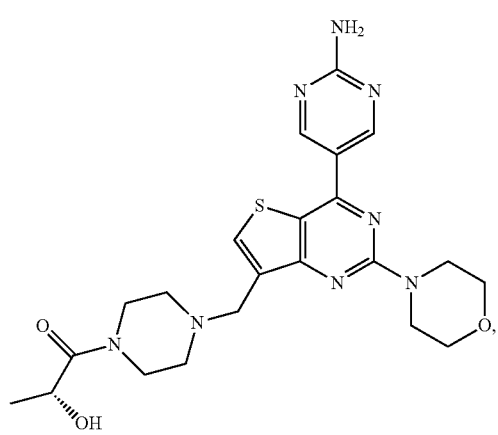
20
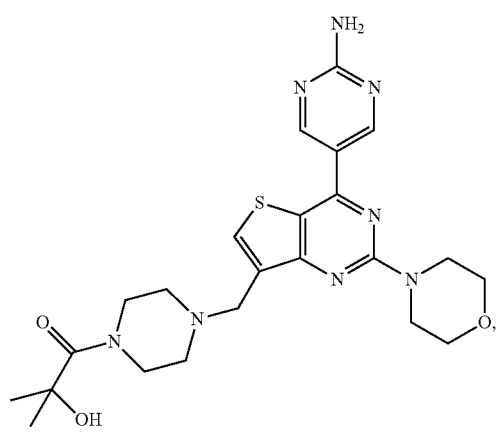
21
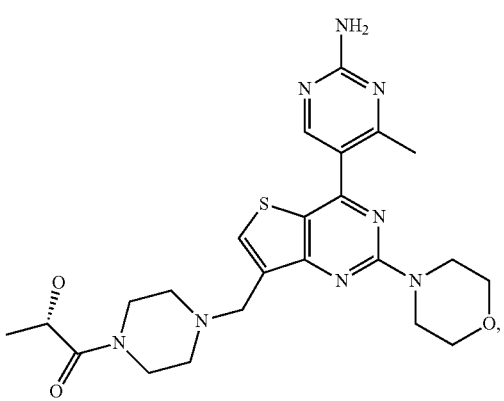
-continued
22
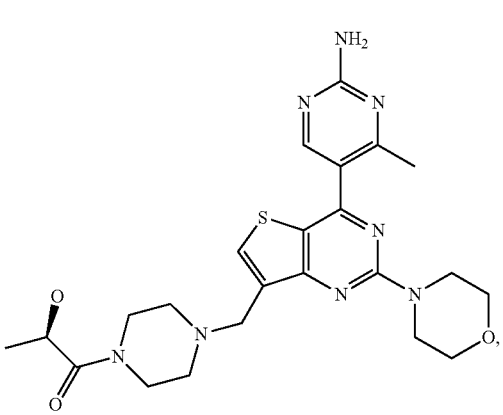
23
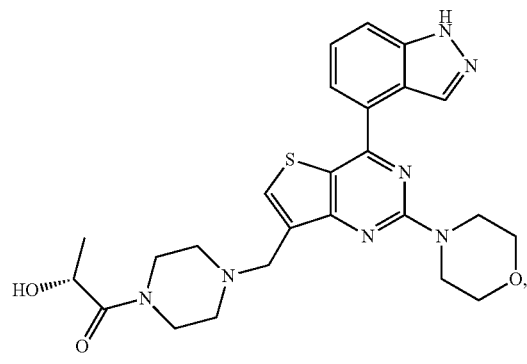
24
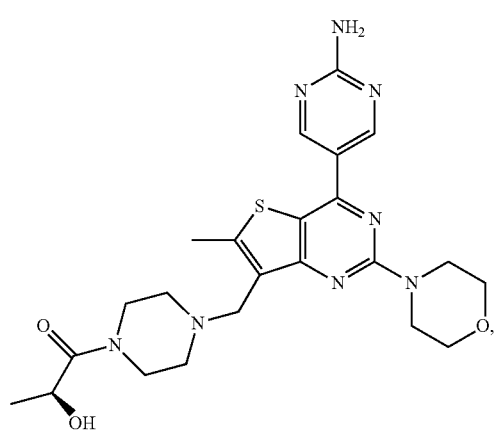
25
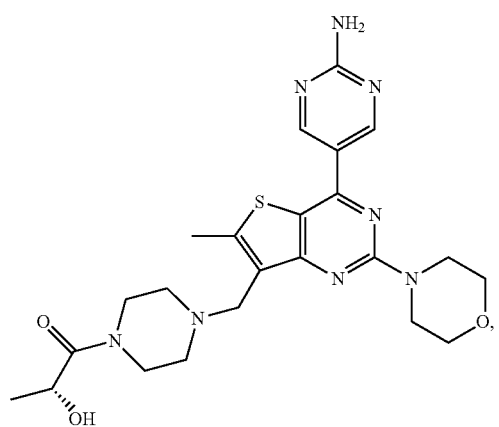

97
-continued
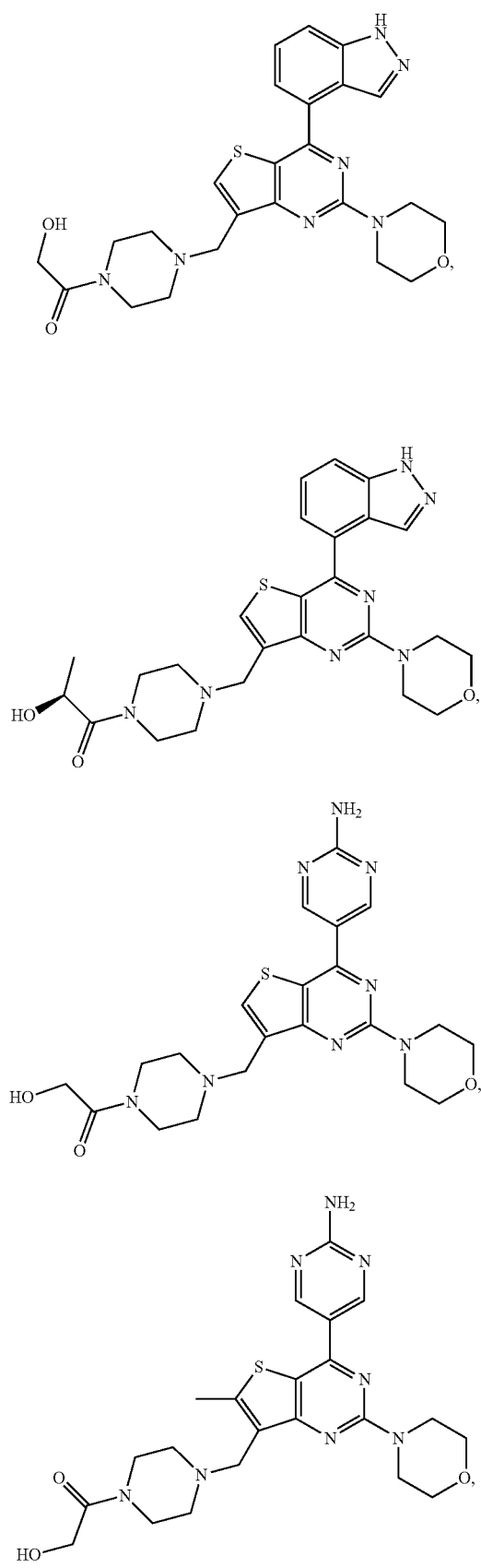
98
-continued
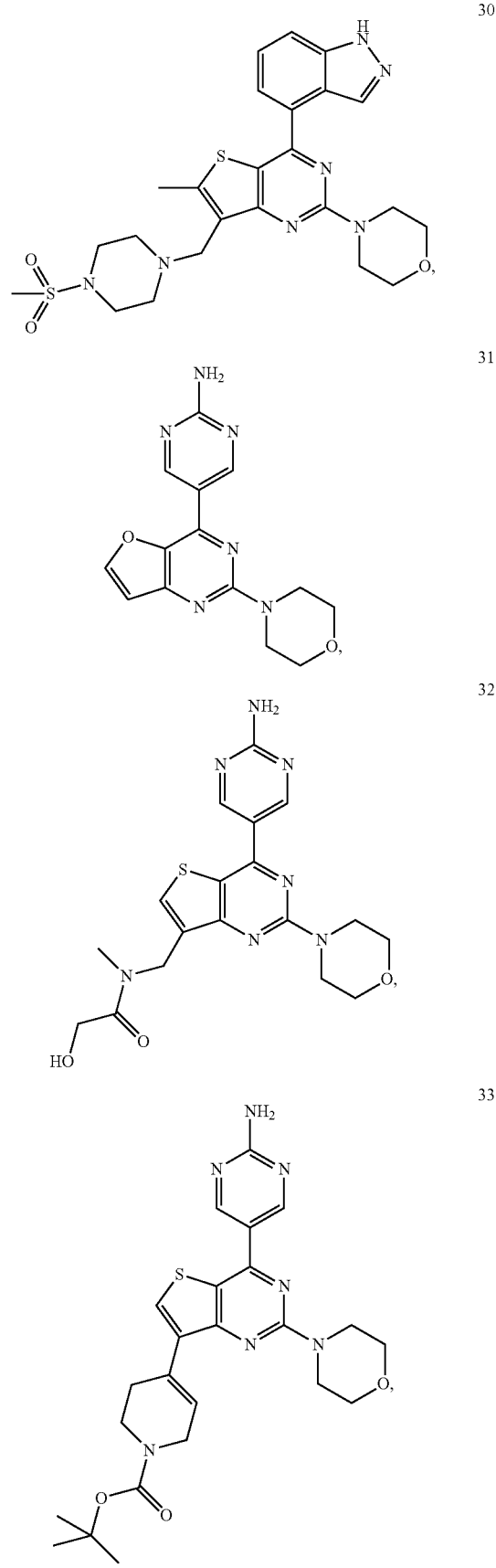

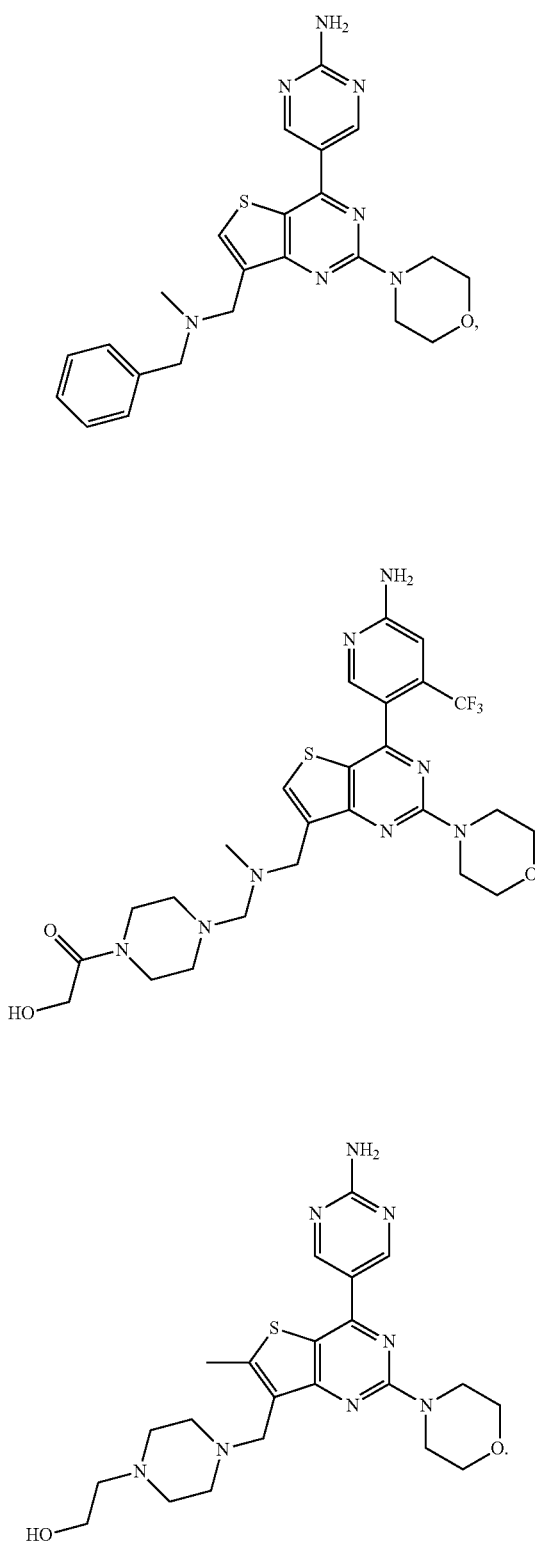

14. A process for preparing the compound I according to claim 1, wherein the process is any one of the following methods:

Method 1: performing the following coupling reaction between a compound I-a and $R^2BF_3K$ or $R^2B(OR^{10})_2$;

wherein, $R^{10}$ is hydrogen, a $C_1$-$C_6$ alkyl, or two $OR^{10}$ groups together with the boron atom to which they are attached form a pinacol borate group as shown below; other groups and letters have the meanings given in claim 1;

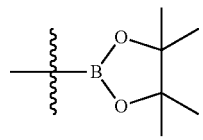

Method 2: further modifying the compound I wherein $R^2$ is the group as shown below, i.e., deprotecting —$CO_2$t-Bu

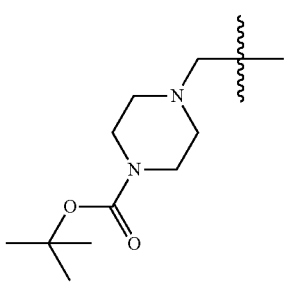 [SMILES: *CN1CCN(C(=O)OC(C)(C)C)CC1]

followed by a N-alkylation, a reductive amination, or a N-acylation reaction, to obtain the compound I, wherein $R^2$ is the group as shown below; other groups have the meanings given in claim 1;

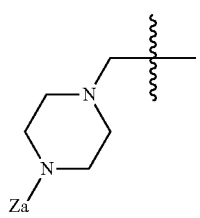

general formula of the compound I in method 2 is shown as below:

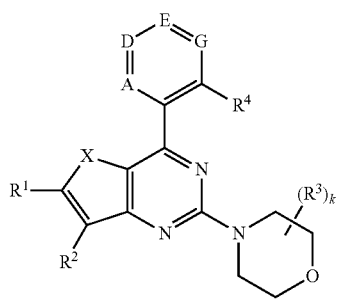

I wherein, Za is —C(=Y)R⁵, —C(=Y)NR⁵R⁶, —S(O)R⁵, —S(O)₂R⁵, or a $C_{1-12}$ alkyl.

15. A method of treating a disease associated with PI3K kinase in a subject in need of a PI3K kinase inhibitor, or an agent used for treating the disease associated with PI3K kinase, comprising administering to the subject a medicament comprising an effective amount of the fused pyrimidine compound represented by formula I, the pharmaceutically acceptable salt, hydrate, and solvate thereof, the optical isomer or the prodrug thereof according to claim 1.

16. The method according to claim 15, wherein the PI3K kinase is Ia subtype of PI3K kinase;

and/or, the disease is cancer, immune disorder, metabolism/endocrine disorder, cardiovascular disease, viral infection, inflammation or neurological disorder, or any combination thereof.

17. A pharmaceutical composition, comprising a therapeutically effective amount of the fused pyrimidine compound represented by formula I, the pharmaceutically acceptable salt, hydrate, and solvate thereof, the optical isomer or the prodrug thereof according to claim 1 and a pharmaceutically acceptable carrier.

18. The method according to claim 16, wherein the cancer is lung cancer, bone cancer, pancreatic cancer, skin cancer, head and neck cancer, melanoma, uterine cancer, ovarian cancer, colorectal cancer, cancer of the anal region, stomach cancer, liver cancer, colon cancer, breast cancer, cervical cancer, vaginal cancer, vulva cancer, Hodgkin's disease, esophageal cancer, small intestine cancer, thyroid cancer, parathyroid cancer, adrenal cancer, soft tissue sarcoma, urethral cancer, penile cancer, prostate cancer, chronic or acute leukemia, childhood solid tumors, lymphocytic lymphoma, bladder cancer, kidney cancer, ureter cancer, pediatric malignancy, primary CNS lymphoma, spinal axis tumors, brain stem glioma, pituitary adenoma, acute myeloid leukemia , chronic myeloid leukemia, or any combination thereof.

* * * * *